(12) United States Patent
Yang et al.

(10) Patent No.: US 12,054,547 B2
(45) Date of Patent: Aug. 6, 2024

(54) ANTI-CTLA4 ANTIBODIES AND USES THEREOF

(71) Applicant: Eucure (Beijing) Biopharma Co., Ltd, Beijing (CN)

(72) Inventors: Yi Yang, Beijing (CN); Yanan Guo, Beijing (CN); Xiaodong Cheng, Beijing (CN); Yunyun Chen, Beijing (CN); Jingshu Xie, Beijing (CN); Chunyan Dong, Beijing (CN); Fang Yang, Beijing (CN); Chengyuan Lu, Beijing (CN); Yuelei Shen, Beijing (CN); Jian Ni, Beijing (CN)

(73) Assignee: Eucure (Beijing) Biopharma Co., Ltd., Beijing (CN)

( * ) Notice: Subject to any disclaimer, the term of this patent is extended or adjusted under 35 U.S.C. 154(b) by 472 days.

(21) Appl. No.: 17/181,454

(22) Filed: Feb. 22, 2021

(65) Prior Publication Data

US 2021/0188981 A1 Jun. 24, 2021

Related U.S. Application Data

(60) Division of application No. 16/815,560, filed on Mar. 11, 2020, now Pat. No. 11,034,764, which is a continuation of application No. PCT/CN2017/102816, filed on Sep. 21, 2017.

(51) Int. Cl.
*C07K 16/28* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *A61K 2039/505* (2013.01); *C07K 2317/24* (2013.01); *C07K 2317/33* (2013.01); *C07K 2317/565* (2013.01); *C07K 2317/622* (2013.01); *C07K 2317/76* (2013.01)

(58) Field of Classification Search
CPC .................................................. C07K 16/2818
USPC ....................................................... 424/135.1
See application file for complete search history.

(56) References Cited

U.S. PATENT DOCUMENTS

| | | | |
|---|---|---|---|
| 4,522,811 | A | 6/1985 | Eppstein et al. |
| 4,603,112 | A | 6/1986 | Paoletti et al. |
| 4,676,980 | A | 6/1987 | Segal et al. |
| 4,769,330 | A | 9/1988 | Paoletti et al. |
| 4,777,127 | A | 10/1988 | Suni et al. |
| 5,017,487 | A | 5/1991 | Stunnenberg et al. |
| 11,034,764 | B2 | 6/2021 | Yang et al. |
| 2007/0071675 | A1 | 3/2007 | Wu et al. |
| 2017/0226211 | A1 | 8/2017 | Wang |
| 2020/0291117 | A1 | 9/2020 | Yang |
| 2023/0041757 | A1* | 2/2023 | Guo ................ C07K 14/52 |

FOREIGN PATENT DOCUMENTS

| | | |
|---|---|---|
| CN | 1802388 | 7/2006 |
| CN | 103547595 | 1/2014 |
| CN | 105296433 | 2/2016 |
| EP | 0345242 | 6/1989 |
| EP | 3176181 | 7/2017 |
| GB | 2200651 | 8/1988 |
| JP | 2009111655 | 5/2009 |
| JP | 2014512809 | 5/2014 |
| JP | 2017523807 | 8/2017 |
| RU | 2346702 | 2/2009 |
| WO | WO 1989/01973 | 3/1989 |
| WO | WO 1991/02805 | 3/1991 |
| WO | WO 2001/77342 | 10/2001 |
| WO | WO 2005/000901 | 1/2005 |
| WO | WO 2012/120125 | 9/2012 |
| WO | WO 2016/196237 | 12/2016 |
| WO | WO 2017/062797 | 4/2017 |
| WO | WO 2021098851 | * 5/2021 |

OTHER PUBLICATIONS

Extended European Search Report in EP Appln. No. 17925693.8, dated Aug. 10, 2021, 11 pages.
Abhinandan et al., "Analysis and improvements to Kabat and structurally correct numbering of antibody variable domains," Molecular immunology, Aug. 1, 2008, 45(14):3832-3839.
Bitter et al., "[33] Expression and secretion vectors for yeast," Methods in enzymology, Jan. 1, 1987, 153:516-544.
Brennan et al., "Preparation of bispecific antibodies by chemical recombination of monoclonal immunoglobulin G1 fragments," Science, Jul. 5, 1985, 229(4708):81-83.
Chothia et al., "Canonical structures for the hypervariable regions of immunoglobulins," Journal of molecular biology, Aug. 20, 1987, 196(4):901-917.
Chothia et al., "Conformations of immunoglobulin hypervariable regions," Nature, Dec. 1989, 342(6252):877-883.
Cohen et al., "Naked DNA points way to vaccines," Science, Mar. 19, 1993, 259(5102):1691-1692.
Colman et al., "Effects of amino acid sequence changes on antibody-antigen interactions," Research in Immunology, Jan. 1, 1994, 145(1):33-36.
Creelan et al., "Update on immune checkpoint inhibitors in lung cancer," Cancer Control, Jan. 2014, 21(1):80-89.
European Search Report in EP Appln. No. 17925693.8, dated Apr. 23, 2021, 13 pages.
Fisher-Hoch et al., "Protection of rhesus monkeys from fatal Lassa fever by vaccination with a recombinant vaccinia virus containing the Lassa virus glycoprotein gene," Proceedings of the National Academy of Sciences, Jan. 1, 1989, 86(1):317-321.
Flexner et al., "Attenuation and immunogenicity in primates of vaccinia virus recombinants expressing human interleukin-2," Vaccine, Feb. 1, 1990, 8(1):17-21.
George et al., "Differential effects of Anti-$\beta_2$-Glycoprotein I Antibodies on endothelial cells and on the manifestations of experimental antiphospholipid syndrome," Amer. heart assoc., 1998, 97:900-906.

(Continued)

*Primary Examiner* — Lynn A Bristol
(74) *Attorney, Agent, or Firm* — Fish & Richardson P.C.

(57) ABSTRACT

This disclosure relates to anti-cytotoxic T-lymphocyte-associated protein 4 (CTLA4 or CTLA-4) antibodies, antigen-binding fragments, and the uses thereof.

18 Claims, 28 Drawing Sheets

Specification includes a Sequence Listing.

(56) References Cited

OTHER PUBLICATIONS

Ghetie et al., "Homodimerization of tumor-reactive monoclonal antibodies markedly increases their ability to induce growth arrest or apoptosis of tumor cells," Proceedings of the National Academy of Sciences, Jul. 8, 1997, 94(14):7509-7514.

Guzman et al., "Efficient and selective adenovirus-mediated gene transfer into vascular neointima," Circulation, Dec. 1993, 88(6):2838-2848.

Guzman et al., "Efficient gene transfer into myocardium by direct injection of adenovirus vectors," Circulation Research, Dec. 1993, 73(6):1202-1207.

Jones et al., "Replacing the complementarity-determining regions in a human antibody with those from a mouse," Nature, May 1986, 321(6069):522-525.

Kass-Eisler et al., "Quantitative determination of adenovirus-mediated gene delivery to rat cardiac myocytes in vitro and in vivo," Proceedings of the National Academy of Sciences, Dec. 15, 1993, 90(24):11498-11502.

Köhler et al., "Continuous cultures of fused cells secreting antibody of predefined specificity," Nature, Aug. 1975, 256(5517):495-497.

Kolls et al., "Prolonged and effective blockade of tumor necrosis factor activity through adenovirus-mediated gene transfer," Proceedings of the National Academy of Sciences, Jan. 4, 1994, 91(1):215-219.

Kozbor et al., "The production of monoclonal antibodies from human lymphocytes," Immunology Today, Mar. 1, 1983, 4(3):72-79.

Martin et al., "Molecular modeling of antibody combining sites," Methods in enzymology, Jan. 1, 1991, 203:121-153.

Martin, "Protein sequence and structure analysis of antibody variable domains," Antibody engineering, Springer Berlin Heidelberg, 2001. 422-439.

Morea et al., "Antibody structure, prediction and redesign," Biophysical chemistry, Oct. 1, 1997, 68(1-3):9-16.

Morea et al., "Conformations of the third hypervariable region in the VH domain of immunoglobulins," Journal of molecular biology, Jan. 16, 1998, 275(2):269-294.

Moss et al., "Vaccinia virus expression vectors," Ann N Y Acad Sci, 1989, 569:86-103.

PCT International Preliminary Report on Patentability Application No. PCT/CN2017/102816, dated Mar. 24, 2020, 9 pages.

PCT International Search Report and Written Opinion in International Application No. PCT/CN2017/102816, dated Jun. 29, 2018, 16 pages.

Ponomarenko et al., "Antibody-protein interactions: benchmark datasets and prediction tools evaluation," BMC structural biology, Dec. 2007, 7(1):1-19.

Riechmann et al., "Reshaping human antibodies for therapy," Nature, Mar. 1988, 332(6162):323-327.

Rosenfeld et al., "Adenovirus-mediated transfer of a recombinant alpha 1-antitrypsin gene to the lung epithelium in vivo," Science, Apr. 19, 1991, 252(5004):431-434.

Rudikoff et al., "Single amino acid substitution altering antigen-binding specificity," Proceedings of the National Academy of Sciences, Mar. 1, 1982, 79(6):1979-1983.

Ulmer et al., "Heterologous protection against influenza by injection of DNA encoding a viral protein, " Science, Mar. 19, 1993, 259(5102):1745-1749.

Vashti et al., "Molecular properties of human IgG subclasses and their implications for designing therapeutic monoclonal antibodies against infectious diseases," Molecular immunology, Oct. 1, 2015, 67(2): 12 pages.

Verhoeyen et al., Reshaping human antibodies: grafting an antilysozyme activity. Science. Mar. 25, 1988;239(4847):1534-1536.

Wolff et al., "Monoclonal antibody homodimers: enhanced antitumor activity in nude mice," Cancer Research, Jun. 1, 1993, 53(11):2560-2565.

Wu et al., "An analysis of the sequences of the variable regions of Bence Jones proteins and myeloma light chains and their implications for antibody complementarity," Journal of Experimental Medicine, Aug. 1, 1970, 132(2):211-250.

Zhao et al., "Enhancing tumor targeting and apoptosis using noncovalent antibody homodimers," Journal of Immunotherapy, Sep. 1, 2002, 25(5):396-404.

Foote et al., "Antibody Framework Residues Affecting the Conformation of the Hypervariable Loops," J. Mol.Biol., 1992, 224(2):487-499.

Winter et al., "Humanized antibodies." Immunology Today, 1993, 14(6):243-246.

Mariuzza et al., "The structural basis of antigen-antibody recognition," Annual review of biophysics and biophysical chemistry, Jun. 1987, 16(1):139-159.

Chen et al., "Enhancement and destruction of antibody function by somatic mutation: unequal occurrence is controlled by V gene combinatorial associations," The EMBO journal, Jun. 1995, 14(12):2784-2794.

Fan et al., "Bispecific antibodies and their applications," Journal of hematology & oncology, Dec. 2015, 8(1):1-14.

Pan et al., "Blocking neuropilin-1 function has an additive effect with anti-VEGF to inhibit tumor growth," Cancer cell, Jan. 1, 2007, 11(1):53-67.

\* cited by examiner

Kabat CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 13A4 or humanized 13A4 | DYEMH | 1 | VIDPETGGTAYNQKFKG | 2 | GTTVVGLDY | 3 | RASGNIHNYLA | 4 | KEKTLTD | 5 | QHFWSTPWT | 6 |
| 4G12 or humanized 4G12 | SYTMS | 7 | TISRGGGYTSYPDSVKG | 8 | EDYGSSYVHWFAY | 9 | RAGENIYSYLA | 10 | NARTLAE | 11 | QHHYGSPRT | 12 |
| 6D2 or humanized 6D2 | DYEMH | 45 | TIDPETGGTAYNQKFKG | 46 | RGKYGNYDYVMDY | 47 | RASGNIHNYLA | 48 | NAKTLAD | 49 | QHFWSTPWT | 50 |
| 7E12 or humanized 7E12 | DYWMN | 51 | QIRNKPYNYETHYSDSVKG | 52 | TFAY | 53 | GTSENIYGGLN | 54 | GATNLAD | 55 | QNVLSTPYT | 56 |

FIG. 23

Chothia CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 13A4 or humanized 13A4 | GYTFT DYEMH | 29 | DPETGG | 30 | GTTVVGLDY | 31 | RASGNIHNYLA | 32 | KEKTLTD | 33 | QHFWSTPWT | 34 |
| 4G12 or humanized 4G12 | GFTFS SYTMS | 35 | SRGGGY | 36 | EDYGSSYVHWFAY | 37 | RAGENIYSYLA | 38 | NARTLAE | 39 | QHHYGSPRT | 40 |
| 6D2 or humanized 6D2 | GYTFT DYEMH | 57 | DPETGG | 58 | RGKYGNYDYVMDY | 59 | RASGNIHNYLA | 60 | NAKTLAD | 61 | QHFWSTPWT | 62 |
| 7E12 or humanized 7E12 | GFTFS DYWMN | 63 | RNKPYNYE | 64 | TFAY | 65 | GTSENIYGGLN | 66 | GATNLAD | 67 | QNVLSTPYT | 68 |

FIG. 24

| Ab | Description | Amino acid sequence | SEQ ID NO: |
|---|---|---|---|
| Humanized 13A4 | HuVHv1: (humanization percentage 86.5%; top hit to human and *Macaca fascicularis*) | QVQLVQSGAEVKKPGASVKVSCKVSGYTFTDYEMHWVRQAPGKGLEWMGVIDPETGG TAYNQKFKGRVTLTADTSTDTAYMELSSLRSEDTAVYYCTRGTTVVGLDYWGQGTTLT VSS | 13 |
| Humanized 13A4 | HuVHv2: (humanization percentage 85.4%; top hit to human and *Macaca fascicularis*) | QVQLVQSGAEVKKPGASVTVSCKVSGYTFTDYEMHWVRQAPGKGLEWMGVIDPETGG TAYNQKFKGRVTLTADTSTDTAYMELSSLRSEDTAVYYCTRGTTVVGLDYWGQGTTLT VSS | 14 |
| Humanized 13A4 | HuVHv3: (humanization percentage 84.4%) | QVQLVQSGAEVKKPGASVTVSCKASGYTFTDYEMHWVRQAPGKGLEWMGVIDPETGG TAYNQKFKGRVTLTADTSTDTAYMELSSLRSEDTAVYYCTRGTTVVGLDYWGQGTTLT VSS | 15 |
| Humanized 13A4 | HuVHv4: (humanization percentage 82.3%) | QVQLVQSGAEVKKPGASVKVSCKASGYTFTDYEMHWVKQAPGKGLEWIGVIDPETGGT AYNQKFKGRVTLTADRSTSTAYMELSSLRSEDTAVYYCTRGTTVVGLDYWGQGTTLTV SS | 16 |
| Humanized 13A4 | HuVHv5: (humanization percentage 81.2%) | QVQLVQSGAEVKKPGASVTVSCKASGYTFTDYEMHWVKQAPGKGLEWIGVIDPETGGT AYNQKFKGRATLTADRSTSTAYMELSSLRSEDTAVYYCTRGTTVVGLDYWGQGTTLTV SS | 17 |
| Humanized 13A4 | HuVLv1: (humanization percentage 85.3%; top hit to human) | DIQMTQSPSSLSASVGDRVTITCRASGNIHNYLAWYQQKPGKAPKLLLYKEKTLTDGVPS RFSGSGSGTQYTLTISSLQPEDFATYYCQHFWSTPWTFGGGTNLEIKR | 18 |
| Humanized 13A4 | HuVLv2: (humanization percentage 83.2%) | DIQMTQSPSSLSASVGDRVTITCRASGNIHNYLAWYQQKPGKAPKLLVYKEKTLTDGVPS RFSGSGSGTQFTLTISSLQPEDFATYYCQHFWSTPWTFGGGTNLEIKR | 19 |
| Humanized 13A4 | HuVLv3: (humanization percentage 82.1%) | DIQMTQSPSSLSASVGDRVTITCRASGNIHNYLAWYQQKPGKSPQLLVYKEKTLTDGVPS RFSGSGSGTQFTLTISSLQPEDFATYYCQHFWSTPWTFGGGTNLEIKR | 20 |
| Humanized 4G12 | huVHv1: (humanization percentage 90.8%; top hit to human) | EVQLVESGGGLVQPGGSLRLSCAASGFTFSSYTMSWVRQAPGKGLEWVATISRGGYTS YPDSVKGRFTISRDNSKNTLYLQMNSLRAEDTAVYYCAREDYGSSYVHWFAYWGQGTL VTVSA | 21 |
| Humanized | huVHv2: (humanization | EVQLVESGGGLVQPGGSLRLSCAASGFTFSSYTMSWVRQAPGKGLEWVATISRGGYTS | 22 |

FIG. 25

| | | | |
|---|---|---|---|
| 4G12 | percentage 89.8%; top hit to human) | YPDSVKGRFTISRDNSKNTLYLQMNSLRAEDTAMYYCAREDYGSSYVHWFAYWGQGTLVTVSA | |
| Humanized 4G12 | 4G12 huVHv3: (humanization percentage 87.8%) | EVQLVESGGGLVQPGGSLRLSCAASGFTFSSYTMSWVRQTPGKRLEWVATISRGGGYTSYPDSVKGRFTISRDNSKNTLYLQMNSLRAEDTAMYYCAREDYGSSYVHWFAYWGQGTLVTVSA | 23 |
| Humanized 4G12 | 4G12 huVHv4: (humanization percentage 85.7%) | EVKLVESGGGLVQPGGSLRLSCAASGFTFSSYTMSWVRQTPEKRLEWVATISRGGGYTSYPDSVKGRFTISRDNSKNTLYLQMNSLRAEDTAMYYCAREDYGSSYVHWFAYWGQGTLVTVSA | 24 |
| Humanized 4G12 | 4G12 huVLv1: (humanization percentage 85.3%; top hit to human) | DIQMTQSPSFLSASVGDRVTITCRAGENIYSYLAWYQQKPGKAPKLLIYNARTLAEGVPSRFSGSGSGTEFTLTISSLQPEDFATYYCQHHYGSPRTFGGGTKLEIKR | 25 |
| Humanized 4G12 | 4G12 huVLv2: (humanization percentage 82.1%, using IGKV1-39*01 as template) | DIQMTQSPSSLSASVGDRVTITCRAGENIYSYLAWYQQKQGKSPKLLVYNARTLAEGVPSRFSGSGSGTDFTLTISSLQPEDFATYYCQHHYGSPRTFGGGTKVEIKR | 26 |
| Humanized 4G12 | 4G12 huVLv3: (humanization percentage 81.1%) | DIQMTQSPSSLSASVGDRVTITCRAGENIYSYLAWYQQKQGKSPKLLVYNARTLAEGVPSRFSGSGSGTQFTLTISSLQPEDFATYYCQHHYGSPRTFGGGTKLEIKR | 27 |
| Humanized 4G12 | 4G12 huVLv4: (humanization percentage 80%, using IGKV1-39*01 as template) | DIQMTQSPSSLSASVGDTVTITCRAGENIYSYLAWYQQKQGKSPQLLVYNARTLAEGVPSRFSGSGSGTDFTLTISSLQPEDFATYYCQHHYGSPRTFGGGTKLEIKR | 28 |

FIG. 25 (continued)

| Protein | Amino acid sequence | SEQ ID NO: |
|---|---|---|
| Human CTLA4 (hCTLA4) | MACLGFQRHKAQLNLATRTWPCTLLFFLLFIPVFCKAMHVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCPDSDFLLWILAAVSSGLFFYSFLLTAVSLSKMLKKRSPLTTGVYVKMPPTEPECEKQFQPYFIPIN | 41 |
| Mouse CTLA4 (mCTLA4) | MACLGLRRYKAQLQLPSRTWPFVALLTLLFIPVFSEAIQVTQPSVVLASSHGVASFPCEYSPSHNTDEVRVTVLRQTNDQMTEVCATTFTEKNTVGFLDYPFCSGTFNESRVNLTIQGLRAVDTGLYLCKVELMYPPPYFVGMGNGTQIYVIDPEPCPDSDFLLWILVAVSLGLFFYSFLVTAVSLSKMLKKRSPLTTGVYVKMPPTEPECEKQFQPYFIPIN | 42 |
| Monkey CTLA4 (mmCTLA4) | MACLGFQRHKARLNLATRTRPYTLLFSLLFIPVFSKAMHVAQPAVVLANSRGIASFVCEYASPGKATEVRVTVLRQADSQVTEVCAATYMMGNELTFLDDSICTGTSSGNQVNLTIQGLRAMDTGLYICKVELMYPPPYMGIGNGTQIYVIDPEPCPDSDFLLWILAAVSSGLFFYSFLLTAVSLSKMLKKRSPLTTGVYVKMPPTEPECEKQFQPYFIPIN | 43 |
| Chimeric CTLA4 (chiCTLA4) (Humanized CTLA4) | MACLGLRRYKAQLQLPSRTWPFVALLTLLFIPVFSEAIQVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCPDSDFLLWILVAVSLGLFFYSFLVTAVSLSKMLKKRSPLTTGVYVKMPPTEPECEKQFQPYFIPIN | 44 |

FIG. 26

CT4-04-13A4 (13A4) Heavy chain variable region (SEQ ID NO: 69)
QVQLQQSGAELVRPGASVTLSCKASGYTFTDYEMHWVKQTPVHGLEWIGVIDPETGGTA
YNQKFKGKATLTADRSSSTAYMELRSLTSEDSAVYYCTRGTTVVGLDYWGQGTTLTVSS

CT4-04-13A4 (13A4) Light chain variable region (SEQ ID NO: 70)
DIQMTQSPASLSASVGESVTITCRASGNIHNYLAWYQQKQGKSPQLLVYKEKTLTDTVPS
RFSGSGSGTQFSLKINSLQPEDFGSYYCQHFWSTPWTFGGGTNLEIK

CT4-03-4G12 (4G12) Heavy chain variable region (SEQ ID NO: 71)
DVKLVESGGGLVKPGGSLKLSCTASGFTFSSYTMSWVRQTPEKRLEWVATISRGGGYTS
YPDSVKGRFTISRDNAKNTLYLQMSSLQSEDTAMYYCARDDYGSSYVHWFAYWGQGTL
VTVSA

CT4-03-4G12 (4G12) Light chain variable region (SEQ ID NO: 72)
DIQMTQSPASLSASVGETVTITCRAGENIYSYLAWYQQKQGKSPQLLVYNARTLAEGVP
SRFSGSGSGTQFSLKINSLQPEDFGSYYCQHHYGSPRTFGGGTKLEIK

CT4-20-6D2 (6D2) Heavy chain variable region (SEQ ID NO: 73)
MEWSWVFLFLLSVIAGVQSQVQLQQSGAELVRPGASVTLSCKASGYTFTDYEMHWVKQTPVHGLEWIGTIDPETGGTAYN
QKFKGKATLTTDKSSSTAYMELRSLTSEDSAVYYCTRRGKYGNYDYVMDYWGQGTSVTSS

CT4-20-6D2 (6D2) Light chain variable region (SEQ ID NO: 74)
MSVLTQVLALLLWLTGARCDIQMTQSPASLSASVGETVTITCRASGNIHNYLAWYQQKQGKSPQLLVFNAKTLADGVPSR
FSGSGSGTQYSLKINSLQPEDFGNYYCQHFWSTPWTFGGGTKLEIK

CT4-20-7E12 (7E12) Heavy chain variable region (SEQ ID NO: 75)
MYLGLSCVFIVFLLKGVQCEVKLDETGGGLVQPGRPMKLSCVASGFTFSDYWMNWVRQSPEKGLEWVAQIRNKPYNYETH
YSDSVKGRFTISRDDSKSSVYLQMNNLRGEDMGIYYCTGTFAYWGQGTLVTVSA

CT4-20-7E12 (7E12) Light chain variable region (SEQ ID NO: 76)
MGVPTQLLLWLTVVVRCDIQMTQSPTSLSASVGETVTITCGTSENIYGGLNWYQRKQGKSPQLLIYGATNLADGMSSRFS
GSGSGRQYSLKISSLHPDDVATYYCQNVLSTPYTFGGGTKLEIK

FIG. 27

SEQUENCE LISTING

```
<160> NUMBER OF SEQ ID NOS: 76

<210> SEQ ID NO 1
<211> LENGTH: 5
<212> TYPE: PRT
<213> ORGANISM: Artificial
<220> FEATURE:
<223> OTHER INFORMATION: CDR sequence

<400> SEQUENCE: 1

Asp Tyr Glu Met His
1               5

<210> SEQ ID NO 2
<211> LENGTH: 17
<212> TYPE: PRT
<213> ORGANISM: Artificial
<220> FEATURE:
<223> OTHER INFORMATION: CDR sequence

<400> SEQUENCE: 2

Val Ile Asp Pro Glu Thr Gly Gly Thr Ala Tyr Asn Gln Lys Phe Lys
1               5                   10                  15
```

Gly

<210> SEQ ID NO 3
<211> LENGTH: 9
<212> TYPE: PRT
<213> ORGANISM: Artificial
<220> FEATURE:
<223> OTHER INFORMATION: CDR sequence

<400> SEQUENCE: 3

Gly Thr Thr Val Val Gly Leu Asp Tyr
1               5

<210> SEQ ID NO 4
<211> LENGTH: 11
<212> TYPE: PRT
<213> ORGANISM: Artificial
<220> FEATURE:
<223> OTHER INFORMATION: CDR sequence

<400> SEQUENCE: 4

Arg Ala Ser Gly Asn Ile His Asn Tyr Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: CDR sequence

<400> SEQUENCE: 5

Lys Glu Lys Thr Leu Thr Asp
1               5

<210> SEQ ID NO 6
<211> LENGTH: 9
<212> TYPE: PRT
<213> ORGANISM: Artificial
<220> FEATURE:
<223> OTHER INFORMATION: CDR sequence

<400> SEQUENCE: 6

Gln His Phe Trp Ser Thr Pro Trp Thr
1               5

<210> SEQ ID NO 7
<211> LENGTH: 5
<212> TYPE: PRT
<213> ORGANISM: Artificial
<220> FEATURE:
<223> OTHER INFORMATION: CDR sequence

<400> SEQUENCE: 7

Ser Tyr Thr Met Ser
1               5

<210> SEQ ID NO 8
<211> LENGTH: 17
<212> TYPE: PRT
<213> ORGANISM: Artificial
<220> FEATURE:
<223> OTHER INFORMATION: CDR sequence

<400> SEQUENCE: 8

Thr Ile Ser Arg Gly Gly Gly Tyr Thr Ser Tyr Pro Asp Ser Val Lys

Gly

<210> SEQ ID NO 9
<211> LENGTH: 13
<212> TYPE: PRT
<213> ORGANISM: Artificial
<220> FEATURE:
<223> OTHER INFORMATION: CDR sequence

<400> SEQUENCE: 9

Glu Asp Tyr Gly Ser Ser Tyr Val His Trp Phe Ala Tyr
1               5                   10

<210> SEQ ID NO 10
<211> LENGTH: 11
<212> TYPE: PRT
<213> ORGANISM: Artificial
<220> FEATURE:
<223> OTHER INFORMATION: CDR sequence

<400> SEQUENCE: 10

Arg Ala Gly Glu Asn Ile Tyr Ser Tyr Leu Ala
1               5                   10

<210> SEQ ID NO 11
<211> LENGTH: 7
<212> TYPE: PRT
<213> ORGANISM: Artificial
<220> FEATURE:
<223> OTHER INFORMATION: CDR sequence

<400> SEQUENCE: 11

Asn Ala Arg Thr Leu Ala Glu
1               5

<210> SEQ ID NO 12
<211> LENGTH: 9
<212> TYPE: PRT
<213> ORGANISM: Artificial
<220> FEATURE:
<223> OTHER INFORMATION: CDR sequence

<400> SEQUENCE: 12

Gln His His Tyr Gly Ser Pro Arg Thr
1               5

<210> SEQ ID NO 13
<211> LENGTH: 118
<212> TYPE: PRT
<213> ORGANISM: Artificial
<220> FEATURE:
<223> OTHER INFORMATION: Humanized heavy chain variable domain (VH)

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Val Ile Asp Pro Glu Thr Gly Gly Thr Ala Tyr Asn Gln Lys Phe
        50                  55                  60

Lys Gly Arg Val Thr Leu Thr Ala Asp Thr Ser Thr Asp Thr Ala Tyr

```
                 65                  70                  75                  80
Met Glu Leu Ser Ser Leu Arg Ser Glu Asp Thr Ala Val Tyr Tyr Cys
                        85                  90                  95

Thr Arg Gly Thr Thr Val Val Gly Leu Asp Tyr Trp Gly Gln Gly Thr
                100                 105                 110

Thr Leu Thr Val Ser Ser
            115

<210> SEQ ID NO 14
<211> LENGTH: 118
<212> TYPE: PRT
<213> ORGANISM: Artificial
<220> FEATURE:
<223> OTHER INFORMATION: Humanized VH

<400> SEQUENCE: 14

Gln Val Gln Leu Val Gln Ser Gly Ala Glu Val Lys Lys Pro Gly Ala
1               5                   10                  15

Ser Val Thr Val Ser Cys Lys Val Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Val Ile Asp Pro Glu Thr Gly Gly Thr Ala Tyr Asn Gln Lys Phe
        50                  55                  60

Lys Gly Arg Val Thr Leu Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                        85                  90                  95

Thr Arg Gly Thr Thr Val Val Gly Leu Asp Tyr Trp Gly Gln Gly Thr
                100                 105                 110

Thr Leu Thr Val Ser Ser
            115

<210> SEQ ID NO 15
<211> LENGTH: 118
<212> TYPE: PRT
<213> ORGANISM: Artificial
<220> FEATURE:
<223> OTHER INFORMATION: Humanized VH

<400> SEQUENCE: 15

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Val Ile Asp Pro Glu Thr Gly Gly Thr Ala Tyr Asn Gln Lys Phe
        50                  55                  60

Lys Gly Arg Val Thr Leu Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                        85                  90                  95

Thr Arg Gly Thr Thr Val Val Gly Leu Asp Tyr Trp Gly Gln Gly Thr
                100                 105                 110

Thr Leu Thr Val Ser Ser
            115
```

```
<210> SEQ ID NO 16
<211> LENGTH: 118
<212> TYPE: PRT
<213> ORGANISM: Artificial
<220> FEATURE:
<223> OTHER INFORMATION: Humanized VH

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Lys Gln Ala Pro Gly Lys Gly Leu Glu Trp Ile
            35                  40                  45

Gly Val Ile Asp Pro Glu Thr Gly Gly Thr Ala Tyr Asn Gln Lys Phe
    50                  55                  60

Lys Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Thr Thr Val Val Gly Leu Asp Tyr Trp Gly Gln Gly Thr
                100                 105                 110

Thr Leu Thr Val Ser Ser
            115

<210> SEQ ID NO 17
<211> LENGTH: 118
<212> TYPE: PRT
<213> ORGANISM: Artificial
<220> FEATURE:
<223> OTHER INFORMATION: Humanized VH

<400> SEQUENCE: 17

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
                20                  25                  30

Glu Met His Trp Val Arg Gln Ala Pro Gly Lys Gly Leu Glu Trp Ile
            35                  40                  45

Gly Val Ile Asp Pro Glu Thr Gly Gly Thr Ala Tyr Asn Gln Lys Phe
    50                  55                  60

Lys Gly Arg Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Thr Thr Val Val Gly Leu Asp Tyr Trp Gly Gln Gly Thr
                100                 105                 110

Thr Leu Thr Val Ser Ser
            115

<210> SEQ ID NO 18
<211> LENGTH: 108
<212> TYPE: PRT
<213> ORGANISM: Artificial
<220> FEATURE:
<223> OTHER INFORMATION: Humanized light chain variable domain (VL)

<400> SEQUENCE: 18

Asp Ile Gln Met Thr Gln Ser Pro Ser Ser Leu Ser Ala Ser Val Gly
```

```
            1               5                  10                  15
Asp Arg Val Thr Ile Thr Cys Arg Ala Ser Gly Asn Ile His Asn Tyr
                20                  25                  30

Leu Ala Trp Tyr Gln Gln Lys Pro Gly Lys Ala Pro Lys Leu Leu Leu
        35                  40                  45

Tyr Lys Glu Lys Thr Leu Thr Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Gln His Phe Trp Ser Thr Pro Trp
                85                  90                  95

Thr Phe Gly Gly Gly Thr Asn Leu Glu Ile Lys Arg
            100                 105

<210> SEQ ID NO 19
<211> LENGTH: 108
<212> TYPE: PRT
<213> ORGANISM: Artificial
<220> FEATURE:
<223> OTHER INFORMATION: Humanized VL

<400> SEQUENCE: 19

Asp Ile Gln Met Thr Gln Ser Pro Ser Ser Leu Ser Ala Ser Val Gly
1               5                  10                  15

Asp Arg Val Thr Ile Thr Cys Arg Ala Ser Gly Asn Ile His Asn Tyr
                20                  25                  30

Leu Ala Trp Tyr Gln Gln Lys Pro Gly Lys Ala Pro Lys Leu Leu Val
        35                  40                  45

Tyr Lys Glu Lys Thr Leu Thr Asp Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His Phe Trp Ser Thr Pro Trp
                85                  90                  95

Thr Phe Gly Gly Gly Thr Asn Leu Glu Ile Lys Arg
            100                 105

<210> SEQ ID NO 20
<211> LENGTH: 108
<212> TYPE: PRT
<213> ORGANISM: Artificial
<220> FEATURE:
<223> OTHER INFORMATION: Humanized VL

<400> SEQUENCE: 20

Asp Ile Gln Met Thr Gln Ser Pro Ser Ser Leu Ser Ala Ser Val Gly
1               5                  10                  15

Asp Arg Val Thr Ile Thr Cys Arg Ala Ser Gly Asn Ile His Asn Tyr
                20                  25                  30

Leu Ala Trp Tyr Gln Gln Lys Pro Gly Lys Ser Pro Gln Leu Leu Val
        35                  40                  45

Tyr Lys Glu Lys Thr Leu Thr Asp Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His Phe Trp Ser Thr Pro Trp
                85                  90                  95
```

```
Thr Phe Gly Gly Gly Thr Asn Leu Glu Ile Lys Arg
            100                 105
```

<210> SEQ ID NO 21
<211> LENGTH: 122
<212> TYPE: PRT
<213> ORGANISM: Artificial
<220> FEATURE:
<223> OTHER INFORMATION: Humanized VH

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Arg Gly Gly Gly Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Tyr Gly Ser Ser Tyr Val His Trp Phe Ala Tyr Trp
            100                 105                 110

Gly Gln Gly Thr Leu Val Thr Val Ser Ala
        115                 120
```

<210> SEQ ID NO 22
<211> LENGTH: 122
<212> TYPE: PRT
<213> ORGANISM: Artificial
<220> FEATURE:
<223> OTHER INFORMATION: Humanized VH

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Arg Gly Gly Gly Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Asp Tyr Gly Ser Ser Tyr Val His Trp Phe Ala Tyr Trp
            100                 105                 110

Gly Gln Gly Thr Leu Val Thr Val Ser Ala
        115                 120
```

<210> SEQ ID NO 23
<211> LENGTH: 122
<212> TYPE: PRT
<213> ORGANISM: Artificial
<220> FEATURE:
<223> OTHER INFORMATION: Humanized VH

```
<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Thr Pro Gly Lys Arg Leu Glu Trp Val
        35                  40                  45

Ala Thr Ile Ser Arg Gly Gly Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Asp Tyr Gly Ser Ser Tyr Val His Trp Phe Ala Tyr Trp
            100                 105                 110

Gly Gln Gly Thr Leu Val Thr Val Ser Ala
            115                 120

<210> SEQ ID NO 24
<211> LENGTH: 122
<212> TYPE: PRT
<213> ORGANISM: Artificial
<220> FEATURE:
<223> OTHER INFORMATION: Humanized VH

<400> SEQUENCE: 24

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Arg Gly Gly Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Asp Tyr Gly Ser Ser Tyr Val His Trp Phe Ala Tyr Trp
            100                 105                 110

Gly Gln Gly Thr Leu Val Thr Val Ser Ala
            115                 120

<210> SEQ ID NO 25
<211> LENGTH: 108
<212> TYPE: PRT
<213> ORGANISM: Artificial
<220> FEATURE:
<223> OTHER INFORMATION: Humanized VL

<400> SEQUENCE: 25

Asp Ile Gln Met Thr Gln Ser Pro Ser Phe Leu Ser Ala Ser Val Gly
1               5                   10                  15

Asp Arg Val Thr Ile Thr Cys Arg Ala Gly Glu Asn Ile Tyr Ser Tyr
            20                  25                  30

Leu Ala Trp Tyr Gln Gln Lys Pro Gly Lys Ala Pro Lys Leu Leu Ile
            35                  40                  45
```

-continued

Tyr Asn Ala Arg Thr Leu Ala Glu Gly Val Pro Ser Arg Phe Ser Gly
          50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln His His Tyr Gly Ser Pro Arg
                  85                  90                  95

Thr Phe Gly Gly Gly Thr Lys Leu Glu Ile Lys Arg
                100                 105

<210> SEQ ID NO 26
<211> LENGTH: 108
<212> TYPE: PRT
<213> ORGANISM: Artificial
<220> FEATURE:
<223> OTHER INFORMATION: Humanized VL

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Arg Ala Gly Glu Asn Ile Tyr Ser Tyr
                 20                  25                  30

Leu Ala Trp Tyr Gln Gln Lys Gln Gly Lys Ser Pro Lys Leu Leu Val
             35                  40                  45

Tyr Asn Ala Arg Thr Leu Ala Glu Gly Val Pro Ser Arg Phe Ser Gly
          50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Ser Pro Arg
                  85                  90                  95

Thr Phe Gly Gly Gly Thr Lys Val Glu Ile Lys Arg
                100                 105

<210> SEQ ID NO 27
<211> LENGTH: 108
<212> TYPE: PRT
<213> ORGANISM: Artificial
<220> FEATURE:
<223> OTHER INFORMATION: Humanized VL

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Gly Glu Asn Ile Tyr Ser Tyr
                 20                  25                  30

Leu Ala Trp Tyr Gln Gln Lys Gln Gly Lys Ser Pro Lys Leu Leu Val
             35                  40                  45

Tyr Asn Ala Arg Thr Leu Ala Glu Gly Val Pro Ser Arg Phe Ser Gly
          50                  55                  60

Ser Gly Ser Gly Thr Gln Phe Thr Leu Thr Ile Ser Ser Leu Gln Pro
 65                  70                  75                  80

Glu Asp Phe Ala Thr Tyr Tyr Cys Gln His His Tyr Gly Ser Pro Arg
                  85                  90                  95

Thr Phe Gly Gly Gly Thr Lys Leu Glu Ile Lys Arg
                100                 105

<210> SEQ ID NO 28
<211> LENGTH: 108
<212> TYPE: PRT
<213> ORGANISM: Artificial

```
<220> FEATURE:
<223> OTHER INFORMATION: Humanized VL

<400> SEQUENCE: 28

Asp Ile Gln Met Thr Gln Ser Pro Ser Ser Leu Ser Ala Ser Val Gly
1               5                   10                  15

Asp Thr Val Thr Ile Thr Cys Arg Ala Gly Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Arg Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ser Pro Arg
                85                  90                  95

Thr Phe Gly Gly Gly Thr Lys Leu Glu Ile Lys Arg
            100                 105

<210> SEQ ID NO 29
<211> LENGTH: 10
<212> TYPE: PRT
<213> ORGANISM: Artificial
<220> FEATURE:
<223> OTHER INFORMATION: CDR sequence

<400> SEQUENCE: 29

Gly Tyr Thr Phe Thr Asp Tyr Glu Met His
1               5                   10

<210> SEQ ID NO 30
<211> LENGTH: 6
<212> TYPE: PRT
<213> ORGANISM: Artificial
<220> FEATURE:
<223> OTHER INFORMATION: CDR sequence

<400> SEQUENCE: 30

Asp Pro Glu Thr Gly Gly
1               5

<210> SEQ ID NO 31
<211> LENGTH: 9
<212> TYPE: PRT
<213> ORGANISM: Artificial
<220> FEATURE:
<223> OTHER INFORMATION: CDR sequence

<400> SEQUENCE: 31

Gly Thr Thr Val Val Gly Leu Asp Tyr
1               5

<210> SEQ ID NO 32
<211> LENGTH: 11
<212> TYPE: PRT
<213> ORGANISM: Artificial
<220> FEATURE:
<223> OTHER INFORMATION: CDR sequence

<400> SEQUENCE: 32

Arg Ala Ser Gly Asn Ile His Asn Tyr Leu Ala
1               5                   10
```

```
<210> SEQ ID NO 33
<211> LENGTH: 7
<212> TYPE: PRT
<213> ORGANISM: Artificial
<220> FEATURE:
<223> OTHER INFORMATION: CDR sequence

<400> SEQUENCE: 33

Lys Glu Lys Thr Leu Thr Asp
1               5

<210> SEQ ID NO 34
<211> LENGTH: 9
<212> TYPE: PRT
<213> ORGANISM: Artificial
<220> FEATURE:
<223> OTHER INFORMATION: CDR sequence

<400> SEQUENCE: 34

Gln His Phe Trp Ser Thr Pro Trp Thr
1               5

<210> SEQ ID NO 35
<211> LENGTH: 10
<212> TYPE: PRT
<213> ORGANISM: Artificial
<220> FEATURE:
<223> OTHER INFORMATION: CDR sequence

<400> SEQUENCE: 35

Gly Phe Thr Phe Ser Ser Tyr Thr Met Ser
1               5                   10

<210> SEQ ID NO 36
<211> LENGTH: 6
<212> TYPE: PRT
<213> ORGANISM: Artificial
<220> FEATURE:
<223> OTHER INFORMATION: CDR sequence

<400> SEQUENCE: 36

Ser Arg Gly Gly Gly Tyr
1               5

<210> SEQ ID NO 37
<211> LENGTH: 13
<212> TYPE: PRT
<213> ORGANISM: Artificial
<220> FEATURE:
<223> OTHER INFORMATION: CDR sequence

<400> SEQUENCE: 37

Glu Asp Tyr Gly Ser Ser Tyr Val His Trp Phe Ala Tyr
1               5                   10

<210> SEQ ID NO 38
<211> LENGTH: 11
<212> TYPE: PRT
<213> ORGANISM: Artificial
<220> FEATURE:
<223> OTHER INFORMATION: CDR sequence

<400> SEQUENCE: 38

Arg Ala Gly Glu Asn Ile Tyr Ser Tyr Leu Ala
1               5                   10

<210> SEQ ID NO 39
```

```
<211> LENGTH: 7
<212> TYPE: PRT
<213> ORGANISM: Artificial
<220> FEATURE:
<223> OTHER INFORMATION: CDR sequence

<400> SEQUENCE: 39

Asn Ala Arg Thr Leu Ala Glu
1               5

<210> SEQ ID NO 40
<211> LENGTH: 9
<212> TYPE: PRT
<213> ORGANISM: Artificial
<220> FEATURE:
<223> OTHER INFORMATION: CDR sequence

<400> SEQUENCE: 40

Gln His His Tyr Gly Ser Pro Arg Thr
1               5

<210> SEQ ID NO 41
<211> LENGTH: 223
<212> TYPE: PRT
<213> ORGANISM: Homo sapiens
<220> FEATURE:
<223> OTHER INFORMATION: CTLA4

<400> SEQUENCE: 41

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 42
<211> LENGTH: 223
```

```
<212> TYPE: PRT
<213> ORGANISM: Mus musculus
<220> FEATURE:
<223> OTHER INFORMATION: CTLA4

<400> SEQUENCE: 42
```

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

```
<210> SEQ ID NO 43
<211> LENGTH: 223
<212> TYPE: PRT
<213> ORGANISM: Macaca Fascicularis
<220> FEATURE:
<223> OTHER INFORMATION: CTLA4

<400> SEQUENCE: 43
```

Met Ala Cys Leu Gly Phe Gln Arg His Lys Ala Arg Leu Asn Leu Ala
1               5                   10                  15

Thr Arg Thr Arg Pro Tyr Thr Leu Leu Phe Ser Leu Leu Phe Ile Pro
            20                  25                  30

Val Phe Ser Lys Ala Met His Val Ala Gln Pro Ala Val Val Leu Ala
        35                  40                  45

Asn Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

```
Asn Leu Thr Ile Gln Gly Leu Arg Ala Met Asp Thr Gly Leu Tyr Ile
            115                 120                 125

Cys Lys Val Glu Leu Met Tyr Pro Pro Tyr Tyr Met Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
        210                 215                 220
```

<210> SEQ ID NO 44
<211> LENGTH: 223
<212> TYPE: PRT
<213> ORGANISM: Artificial
<220> FEATURE:
<223> OTHER INFORMATION: Chimeric CTLA4

<400> SEQUENCE: 44

```
Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
        210                 215                 220
```

<210> SEQ ID NO 45
<211> LENGTH: 5
<212> TYPE: PRT
<213> ORGANISM: Artificial

<220> FEATURE:
<223> OTHER INFORMATION: CDR sequence

<400> SEQUENCE: 45

Asp Tyr Glu Met His
1               5

<210> SEQ ID NO 46
<211> LENGTH: 17
<212> TYPE: PRT
<213> ORGANISM: Artificial
<220> FEATURE:
<223> OTHER INFORMATION: CDR sequence

<400> SEQUENCE: 46

Thr Ile Asp Pro Glu Thr Gly Gly Thr Ala Tyr Asn Gln Lys Phe Lys
1               5                   10                  15

Gly

<210> SEQ ID NO 47
<211> LENGTH: 13
<212> TYPE: PRT
<213> ORGANISM: Artificial
<220> FEATURE:
<223> OTHER INFORMATION: CDR sequence

<400> SEQUENCE: 47

Arg Gly Lys Tyr Gly Asn Tyr Asp Tyr Val Met Asp Tyr
1               5                   10

<210> SEQ ID NO 48
<211> LENGTH: 11
<212> TYPE: PRT
<213> ORGANISM: Artificial
<220> FEATURE:
<223> OTHER INFORMATION: CDR sequence

<400> SEQUENCE: 48

Arg Ala Ser Gly Asn Ile His Asn Tyr Leu Ala
1               5                   10

<210> SEQ ID NO 49
<211> LENGTH: 7
<212> TYPE: PRT
<213> ORGANISM: Artificial
<220> FEATURE:
<223> OTHER INFORMATION: CDR sequence

<400> SEQUENCE: 49

Asn Ala Lys Thr Leu Ala Asp
1               5

<210> SEQ ID NO 50
<211> LENGTH: 9
<212> TYPE: PRT
<213> ORGANISM: Artificial
<220> FEATURE:
<223> OTHER INFORMATION: CDR sequence

<400> SEQUENCE: 50

Gln His Phe Trp Ser Thr Pro Trp Thr
1               5

<210> SEQ ID NO 51
<211> LENGTH: 5
<212> TYPE: PRT

```
<213> ORGANISM: Artificial
<220> FEATURE:
<223> OTHER INFORMATION: CDR sequence

<400> SEQUENCE: 51

Asp Tyr Trp Met Asn
1               5

<210> SEQ ID NO 52
<211> LENGTH: 19
<212> TYPE: PRT
<213> ORGANISM: Artificial
<220> FEATURE:
<223> OTHER INFORMATION: CDR sequence

<400> SEQUENCE: 52

Gln Ile Arg Asn Lys Pro Tyr Asn Tyr Glu Thr His Tyr Ser Asp Ser
1               5                   10                  15

Val Lys Gly

<210> SEQ ID NO 53
<211> LENGTH: 4
<212> TYPE: PRT
<213> ORGANISM: Artificial
<220> FEATURE:
<223> OTHER INFORMATION: CDR sequence

<400> SEQUENCE: 53

Thr Phe Ala Tyr
1

<210> SEQ ID NO 54
<211> LENGTH: 11
<212> TYPE: PRT
<213> ORGANISM: Artificial
<220> FEATURE:
<223> OTHER INFORMATION: CDR sequence

<400> SEQUENCE: 54

Gly Thr Ser Glu Asn Ile Tyr Gly Gly Leu Asn
1               5                   10

<210> SEQ ID NO 55
<211> LENGTH: 7
<212> TYPE: PRT
<213> ORGANISM: Artificial
<220> FEATURE:
<223> OTHER INFORMATION: CDR sequence

<400> SEQUENCE: 55

Gly Ala Thr Asn Leu Ala Asp
1               5

<210> SEQ ID NO 56
<211> LENGTH: 9
<212> TYPE: PRT
<213> ORGANISM: Artificial
<220> FEATURE:
<223> OTHER INFORMATION: CDR sequence

<400> SEQUENCE: 56

Gln Asn Val Leu Ser Thr Pro Tyr Thr
1               5

<210> SEQ ID NO 57
<211> LENGTH: 10
```

```
<212> TYPE: PRT
<213> ORGANISM: Artificial
<220> FEATURE:
<223> OTHER INFORMATION: CDR sequence

<400> SEQUENCE: 57

Gly Tyr Thr Phe Thr Asp Tyr Glu Met His
1               5                   10

<210> SEQ ID NO 58
<211> LENGTH: 6
<212> TYPE: PRT
<213> ORGANISM: Artificial
<220> FEATURE:
<223> OTHER INFORMATION: CDR sequence

<400> SEQUENCE: 58

Asp Pro Glu Thr Gly Gly
1               5

<210> SEQ ID NO 59
<211> LENGTH: 13
<212> TYPE: PRT
<213> ORGANISM: Artificial
<220> FEATURE:
<223> OTHER INFORMATION: CDR sequence

<400> SEQUENCE: 59

Arg Gly Lys Tyr Gly Asn Tyr Asp Tyr Val Met Asp Tyr
1               5                   10

<210> SEQ ID NO 60
<211> LENGTH: 11
<212> TYPE: PRT
<213> ORGANISM: Artificial
<220> FEATURE:
<223> OTHER INFORMATION: CDR sequence

<400> SEQUENCE: 60

Arg Ala Ser Gly Asn Ile His Asn Tyr Leu Ala
1               5                   10

<210> SEQ ID NO 61
<211> LENGTH: 7
<212> TYPE: PRT
<213> ORGANISM: Artificial
<220> FEATURE:
<223> OTHER INFORMATION: CDR sequence

<400> SEQUENCE: 61

Asn Ala Lys Thr Leu Ala Asp
1               5

<210> SEQ ID NO 62
<211> LENGTH: 9
<212> TYPE: PRT
<213> ORGANISM: Artificial
<220> FEATURE:
<223> OTHER INFORMATION: CDR sequence

<400> SEQUENCE: 62

Gln His Phe Trp Ser Thr Pro Trp Thr
1               5

<210> SEQ ID NO 63
<211> LENGTH: 10
<212> TYPE: PRT
```

```
<213> ORGANISM: Artificial
<220> FEATURE:
<223> OTHER INFORMATION: CDR sequence

<400> SEQUENCE: 63

Gly Phe Thr Phe Ser Asp Tyr Trp Met Asn
1               5                   10

<210> SEQ ID NO 64
<211> LENGTH: 8
<212> TYPE: PRT
<213> ORGANISM: Artificial
<220> FEATURE:
<223> OTHER INFORMATION: CDR sequence

<400> SEQUENCE: 64

Arg Asn Lys Pro Tyr Asn Tyr Glu
1               5

<210> SEQ ID NO 65
<211> LENGTH: 4
<212> TYPE: PRT
<213> ORGANISM: Artificial
<220> FEATURE:
<223> OTHER INFORMATION: CDR sequence

<400> SEQUENCE: 65

Thr Phe Ala Tyr
1

<210> SEQ ID NO 66
<211> LENGTH: 11
<212> TYPE: PRT
<213> ORGANISM: Artificial
<220> FEATURE:
<223> OTHER INFORMATION: CDR sequence

<400> SEQUENCE: 66

Gly Thr Ser Glu Asn Ile Tyr Gly Gly Leu Asn
1               5                   10

<210> SEQ ID NO 67
<211> LENGTH: 7
<212> TYPE: PRT
<213> ORGANISM: Artificial
<220> FEATURE:
<223> OTHER INFORMATION: CDR sequence

<400> SEQUENCE: 67

Gly Ala Thr Asn Leu Ala Asp
1               5

<210> SEQ ID NO 68
<211> LENGTH: 9
<212> TYPE: PRT
<213> ORGANISM: Artificial
<220> FEATURE:
<223> OTHER INFORMATION: CDR sequence

<400> SEQUENCE: 68

Gln Asn Val Leu Ser Thr Pro Tyr Thr
1               5

<210> SEQ ID NO 69
<211> LENGTH: 118
<212> TYPE: PRT
<213> ORGANISM: Mus musculus
```

<220> FEATURE:
<223> OTHER INFORMATION: VH

<400> SEQUENCE: 69

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Val Ile Asp Pro Glu Thr Gly Gly Thr Ala Tyr Asn Gln Lys Phe
    50                  55                  60

Lys Gly Lys Ala Thr Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Gly Thr Thr Val Val Gly Leu Asp Tyr Trp Gly Gln Gly Thr
            100                 105                 110

Thr Leu Thr Val Ser Ser
        115

<210> SEQ ID NO 70
<211> LENGTH: 107
<212> TYPE: PRT
<213> ORGANISM: Mus musculus
<220> FEATURE:
<223> OTHER INFORMATION: VL

<400> SEQUENCE: 70

Asp Ile Gln Met Thr Gln Ser Pro Ala Ser Leu Ser Ala Ser Val Gly
1               5                   10                  15

Glu Ser Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Lys Glu Lys Thr Leu Thr Asp Thr Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Asn Leu Glu Ile Lys
            100                 105

<210> SEQ ID NO 71
<211> LENGTH: 122
<212> TYPE: PRT
<213> ORGANISM: Mus musculus
<220> FEATURE:
<223> OTHER INFORMATION: VH

<400> SEQUENCE: 71

Asp Val Lys Leu Val Glu Ser Gly Gly Gly Leu Val Lys Pro Gly Gly
1               5                   10                  15

Ser Leu Lys Leu Ser Cys Thr Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Arg Gly Gly Gly Tyr Thr Ser Tyr Pro Asp Ser Val
    50              55                  60

Lys Gly Arg Phe Thr Ile Ser Arg Asp Asn Ala Lys Asn Thr Leu Tyr
65              70                  75                  80

Leu Gln Met Ser Ser Leu Gln Ser Glu Asp Thr Ala Met Tyr Tyr Cys
                85                  90                  95

Ala Arg Asp Asp Tyr Gly Ser Ser Tyr Val His Trp Phe Ala Tyr Trp
            100                 105                 110

Gly Gln Gly Thr Leu Val Thr Val Ser Ala
            115                 120

<210> SEQ ID NO 72
<211> LENGTH: 107
<212> TYPE: PRT
<213> ORGANISM: Mus musculus
<220> FEATURE:
<223> OTHER INFORMATION: VL

<400> SEQUENCE: 72

Asp Ile Gln Met Thr Gln Ser Pro Ala Ser Leu Ser Ala Ser Val Gly
1               5                   10                  15

Glu Thr Val Thr Ile Thr Cys Arg Ala Gly Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Arg Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65              70                  75                  80

Glu Asp Phe Gly Ser Tyr Tyr Cys Gln His His Tyr Gly Ser Pro Arg
                85                  90                  95

Thr Phe Gly Gly Gly Thr Lys Leu Glu Ile Lys
            100                 105

<210> SEQ ID NO 73
<211> LENGTH: 141
<212> TYPE: PRT
<213> ORGANISM: Mus musculus
<220> FEATURE:
<223> OTHER INFORMATION: VH

<400> SEQUENCE: 73

Met Glu Trp Ser Trp Val Phe Leu Phe Leu Leu Ser Val Ile Ala Gly
1               5                   10                  15

Val Gln Ser Gln Val Gln Leu Gln Gln Ser Gly Ala Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Thr Ile Asp Pro Glu Thr Gly Gly Thr Ala Tyr Asn
65              70                  75                  80

Gln Lys Phe Lys Gly Lys Ala Thr Leu Thr Thr Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Thr Arg Arg Gly Lys Tyr Gly Asn Tyr Asp Tyr Val Met
        115                 120                 125

Asp Tyr Trp Gly Gln Gly Thr Ser Val Thr Val Ser Ser
    130                 135                 140

<210> SEQ ID NO 74
<211> LENGTH: 127
<212> TYPE: PRT
<213> ORGANISM: Mus musculus
<220> FEATURE:
<223> OTHER INFORMATION: VL

<400> SEQUENCE: 74

Met Ser Val Leu Thr Gln Val Leu Ala Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
                35                  40                  45

Ile His Asn Tyr Leu Ala Trp Tyr Gln Gln Lys Gln Gly Lys Ser Pro
    50                  55                  60

Gln Leu Leu Val Phe Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Asn Tyr Tyr Cys Gln His Phe Trp
            100                 105                 110

Ser Thr Pro Trp Thr Phe Gly Gly Gly Thr Lys Leu Glu Ile Lys
        115                 120                 125

<210> SEQ ID NO 75
<211> LENGTH: 134
<212> TYPE: PRT
<213> ORGANISM: Mus musculus
<220> FEATURE:
<223> OTHER INFORMATION: VH

<400> SEQUENCE: 75

Met Tyr Leu Gly Leu Ser Cys Val Phe Ile Val Phe Leu Leu Lys Gly
1               5                   10                  15

Val Gln Cys Glu Val Lys Leu Asp Glu Thr Gly Gly Gly Leu Val Gln
            20                  25                  30

Pro Gly Arg Pro Met Lys Leu Ser Cys Val Ala Ser Gly Phe Thr Phe
        35                  40                  45

Ser Asp Tyr Trp Met Asn Trp Val Arg Gln Ser Pro Glu Lys Gly Leu
    50                  55                  60

Glu Trp Val Ala Gln Ile Arg Asn Lys Pro Tyr Asn Tyr Glu Thr His
65                  70                  75                  80

Tyr Ser Asp Ser Val Lys Gly Arg Phe Thr Ile Ser Arg Asp Asp Ser
                85                  90                  95

Lys Ser Ser Val Tyr Leu Gln Met Asn Asn Leu Arg Gly Glu Asp Met
            100                 105                 110

Gly Ile Tyr Tyr Cys Thr Gly Thr Phe Ala Tyr Trp Gly Gln Gly Thr
        115                 120                 125

Leu Val Thr Val Ser Ala
        130

<210> SEQ ID NO 76
<211> LENGTH: 126
<212> TYPE: PRT

```
<213> ORGANISM: Mus musculus
<220> FEATURE:
<223> OTHER INFORMATION: VL

<400> SEQUENCE: 76

Met Gly Val Pro Thr Gln Leu Leu Leu Trp Leu Thr Val Val Val
1               5                   10                  15

Val Arg Cys Asp Ile Gln Met Thr Gln Ser Pro Thr Ser Leu Ser Ala
            20                  25                  30

Ser Val Gly Glu Thr Val Thr Ile Thr Cys Gly Thr Ser Glu Asn Ile
        35                  40                  45

Tyr Gly Gly Leu Asn Trp Tyr Gln Arg Lys Gln Gly Lys Ser Pro Gln
    50                  55                  60

Leu Leu Ile Tyr Gly Ala Thr Asn Leu Ala Asp Gly Met Ser Ser Arg
65                  70                  75                  80

Phe Ser Gly Ser Gly Ser Gly Arg Gln Tyr Ser Leu Lys Ile Ser Ser
                85                  90                  95

Leu His Pro Asp Asp Val Ala Thr Tyr Tyr Cys Gln Asn Val Leu Ser
            100                 105                 110

Thr Pro Tyr Thr Phe Gly Gly Gly Thr Lys Leu Glu Ile Lys
            115                 120                 125
```

ANTI-CTLA4 ANTIBODIES AND USES THEREOF

CLAIM OF PRIORITY

This application is a divisional application of and claims priority to U.S. application Ser. No. 16/815,560, filed on Mar. 11, 2020, which is a continuation application of and claims priority to International Application No. PCT/CN2017/102816, filed on Sep. 21, 2017. The entire contents of the foregoing are incorporated herein by reference.

TECHNICAL FIELD

This disclosure relates to cytotoxic T-lymphocyte-associated protein 4 (CTLA4 or CTLA-4) antibodies and uses thereof.

BACKGROUND

Cancer is currently one of the diseases that have the highest human mortality. According to the World Health Organization statistical data, in 2012, the number of global cancer incidence and death cases reached 14 million and 8.2 million, respectively. In China, the newly diagnosed cancer cases are 3.07 million, and the death toll is 2.2 million.

Recent clinical and commercial success of anticancer antibodies has created great interest in antibody-based therapeutics. There is a need to develop anti-cancer antibodies for use in various antibody-based therapeutics to treat cancers.

SUMMARY

This disclosure relates to anti-CTLA4 antibodies, antigen-binding fragment thereof, and the uses thereof.

In one aspect, the disclosure relates to an antibody or antigen-binding fragment thereof that binds to cytotoxic T-lymphocyte-associated protein 4 (CTLA4) comprising: a heavy chain variable region (VH) comprising complementarity determining regions (CDRs) 1, 2, and 3, wherein the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and a light chain variable region (VL) comprising CDRs 1, 2, and 3, wherein the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence, wherein the selected VH CDRs 1, 2, and 3 amino acid sequences and the selected VL CDRs, 1, 2, and 3 amino acid sequences are one of the following:
  (1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively;
  (2) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively;
  (3) the selected VH CDRs 1, 2, 3 amino acid sequences are set forth in SEQ ID NOs: 45, 46, 47, respectively, and the selected VL CDRs 1, 2, 3 amino acid sequences are set forth in SEQ ID NOs: 48, 49, 50, respectively;
  (4) the selected VH CDRs 1, 2, 3 amino acid sequences are set forth in SEQ ID NOs: 51, 52, 53, respectively, and the selected VL CDRs 1, 2, 3 amino acid sequences are set forth in SEQ ID NOs: 54, 55, 56, respectively.

In some embodiments, the VH comprises CDRs 1, 2, 3 with the amino acid sequences set forth in SEQ ID NOs: 1, 2, and 3 respectively, and the VL comprises CDRs 1, 2, 3 with the amino acid sequences set forth in SEQ ID NOs: 4, 5, and 6, respectively.

In some embodiments, the VH comprises CDRs 1, 2, 3 with the amino acid sequences set forth in SEQ ID NOs: 7, 8, and 9 respectively, and the VL comprises CDRs 1, 2, 3 with the amino acid sequences set forth in SEQ ID NOs: 10, 11, and 12, respectively.

In some embodiments, the antibody or antigen-binding fragment specifically binds to human CTLA4. In some embodiments, the antibody or antigen-binding fragment is a humanized antibody or antigen-binding fragment thereof. In some embodiments, the antibody or antigen-binding fragment is a single-chain variable fragment (scFV).

In one aspect, the disclosure relates to a nucleic acid comprising a polynucleotide encoding a polypeptide comprising:
  (1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 1, 2, and 3, respectively, and wherein the VH, when paired with a light chain variable region (VL) comprising the amino acid sequence set forth in SEQ ID NO: 18, 19, 20, or 70, binds to CTLA4;
  (2) an immunoglobulin light chain or a fragment thereof comprising a VL comprising CDRs 1, 2, and 3 comprising the amino acid sequences set forth in SEQ ID NOs: 4, 5, and 6, respectively, and wherein the VL, when paired with a VH comprising the amino acid sequence set forth in SEQ ID NO: 13, 14, 15, 16, 17, or 69, binds to CTLA4;
  (3) an immunoglobulin heavy chain or a fragment thereof comprising a heavy chain variable region (VH) comprising CDRs 1, 2, and 3 comprising the amino acid sequences set forth in SEQ ID NOs: 7, 8, and 9, respectively, and wherein the VH, when paired with a light chain variable region (VL) comprising the amino acid sequence set forth in SEQ ID NO: 25, 26, 27, 28, or 72, binds to CTLA4; or
  (4) an immunoglobulin light chain or a fragment thereof comprising a VL comprising CDRs 1, 2, and 3 comprising the amino acid sequences set forth in SEQ ID NOs: 10, 11, and 12, respectively, and wherein the VL, when paired with a VH comprising the amino acid sequence set forth in SEQ ID NO: 21, 22, 23, 24, or 71, binds to CTLA4;
  (5) an immunoglobulin heavy chain or a fragment thereof comprising a heavy chain variable region (VH) comprising CDRs 1, 2, and 3 comprising the amino acid sequences set forth in SEQ ID NOs: 45, 46, and 47, respectively, and wherein the VH, when paired with a light chain variable region (VL) comprising the amino acid sequence set forth in SEQ ID NO: 74, binds to CTLA4;

(6) an immunoglobulin light chain or a fragment thereof comprising a VL comprising CDRs 1, 2, and 3 comprising the amino acid sequences set forth in SEQ ID NOs: 48, 49, and 50, respectively, and wherein the VL, when paired with a VH comprising the amino acid sequence set forth in SEQ ID NO: 73, binds to CTLA4;

(7) an immunoglobulin heavy chain or a fragment thereof comprising a heavy chain variable region (VH) comprising CDRs 1, 2, and 3 comprising the amino acid sequences set forth in SEQ ID NOs: 51, 52, and 53, respectively, and wherein the VH, when paired with a light chain variable region (VL) comprising the amino acid sequence set forth in SEQ ID NO: 76, binds to CTLA4;

(8) an immunoglobulin light chain or a fragment thereof comprising a VL comprising CDRs 1, 2, and 3 comprising the amino acid sequences set forth in SEQ ID NOs: 54, 55, and 56, respectively, and wherein the VL, when paired with a VH comprising the amino acid sequence set forth in SEQ ID NO: 75, binds to CTLA4.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 1, 2, and 3, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 4, 5, and 6, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 7, 8, and 9, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 10, 11, and 12, respectively.

In some embodiments, the VH when paired with a VL specifically binds to human CTLA4. In some embodiments, the VL when paired with a VH specifically binds to human CTLA4.

In some embodiments, the immunoglobulin heavy chain or the fragment thereof is a humanized immunoglobulin heavy chain or a fragment thereof, and the immunoglobulin light chain or the fragment thereof is a humanized immunoglobulin light chain or a fragment thereof.

In some embodiments, the nucleic acid encodes a single-chain variable fragment (scFv). In some embodiments, the nucleic acid is cDNA.

In another aspect, the disclosure also provides a vector comprising one or more of the nucleic acids as described herein. In some embodiments, the vector encodes the VL region and the VH region that together bind to a CTLA4.

In one aspect, the disclosure relates to a pair of vectors, wherein each vector comprises one of the nucleic acids as described herein, wherein together the pair of vectors encodes the VL region and the VH region that together bind to CTLA4.

In one aspect, the disclosure provides a cell comprising the vector as described herein, or the pair of vectors as described herein. In some embodiments, the cell is a CHO cell.

In another aspect, the disclosure relates to a cell comprising one or more of the nucleic acids as described herein.

In one aspect, the disclosure provides a cell comprising two of the nucleic acids as described herein. In some embodiments, the two nucleic acids together encode the VL region and the VH region that together bind to CTLA4.

In one aspect, the disclosure also provides a method of producing an antibody or an antigen-binding fragment thereof. The method includes the steps of culturing the cell as described herein under conditions sufficient for the cell to produce the antibody or the antigen-binding fragment; and collecting the antibody or the antigen-binding fragment produced by the cell.

In one aspect, the disclosure relates to an antibody or antigen-binding fragment thereof that binds to CTLA4 comprising a heavy chain variable region (VH) comprising an amino acid sequence that is at least 90% identical to a selected VH sequence, and a light chain variable region (VL) comprising an amino acid sequence that is at least 90% identical to a selected VL sequence, wherein the selected VH sequence and the selected VL sequence are one of the following:

(1) the selected VH sequence is SEQ ID NO: 13, 14, 15, 16, 17, or 69, and the selected VL sequence is SEQ ID NO: 18, 19, 20, or 70;

(2) the selected VH sequence is SEQ ID NO: 21, 22, 23, 24, or 71, and the selected VL sequence is SEQ ID NO: 25, 26, 27, 28, or 72;

(3) the selected VH sequence is SEQ ID NO: 73, and the selected VL sequence is SEQ ID NO: 74;

(4) the selected VH sequence is SEQ ID NO: 75, and the selected VL sequence is SEQ ID NO: 76.

In some embodiments, the VH comprises the sequence of SEQ ID NO: 13 and the VL comprises the sequence of SEQ ID NO: 19. In some embodiments, the VH comprises the sequence of SEQ ID NO: 14 and the VL comprises the sequence of SEQ ID NO: 19.

In some embodiments, the VH comprises the sequence of SEQ ID NO: 21 and the VL comprises the sequence of SEQ ID NO: 25. In some embodiments, the VH comprises the sequence of SEQ ID NO: 22 and the VL comprises the sequence of SEQ ID NO: 25.

In some embodiments, the antibody or antigen-binding fragment specifically binds to human CTLA4. In some embodiments, the antibody or antigen-binding fragment is a humanized antibody or antigen-binding fragment thereof. In some embodiments, the antibody or antigen-binding fragment is a single-chain variable fragment (scFV).

In one aspect, the disclosure also provides an antibody-drug conjugate comprising the antibody or antigen-binding fragment thereof covalently or non-covalently bound to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

In one aspect, the disclosure provides a method of treating a subject having cancer. The method includes the steps of administering a therapeutically effective amount of a composition comprising the antibody or antigen-binding fragment as described herein, or the antibody-drug conjugate as described herein, to the subject.

In some embodiments, the cancer is melanoma. In some embodiments, the cancer is unresectable melanoma or metastatic melanoma.

In some embodiments, the cancer is non-small cell lung carcinoma (NSCLC), small cell lung cancer (SCLC), bladder cancer, or metastatic hormone-refractory prostate cancer.

In one aspect, the disclosure also provides a method of decreasing the rate of tumor growth. The method includes the steps of contacting a tumor cell with an effective amount of a composition comprising an antibody or antigen-binding fragment thereof as described herein.

In another aspect, the disclosure relates to a method of killing a tumor cell, the method includes the steps of contacting a tumor cell with an effective amount of a composition comprising the antibody or antigen-binding fragment thereof as described herein, or the antibody-drug conjugate as described herein.

In one aspect, the disclosure provides a pharmaceutical composition comprising the antibody or antigen-binding fragment thereof as described herein, and a pharmaceutically acceptable carrier.

In another aspect, the disclosure relates to a pharmaceutical composition comprising the antibody drug conjugate as described herein, and a pharmaceutically acceptable carrier.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, and cancer of the small intestine. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

As used herein, the term "antibody" refers to any antigen-binding molecule that contains at least one (e.g., one, two, three, four, five, or six) complementary determining region (CDR) (e.g., any of the three CDRs from an immunoglobulin light chain or any of the three CDRs from an immunoglobulin heavy chain) and is capable of specifically binding to an epitope. Non-limiting examples of antibodies include: monoclonal antibodies, polyclonal antibodies, multi-specific antibodies (e.g., bi-specific antibodies), single-chain antibodies, chimeric antibodies, human antibodies, and humanized antibodies. In some embodiments, an antibody can contain an Fc region of a human antibody. The term antibody also includes derivatives, e.g., bi-specific antibodies, single-chain antibodies, diabodies, linear antibodies, and multi-specific antibodies formed from antibody fragments.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain). Non-limiting examples of antibody fragments include, e.g., Fab, Fab', F(ab')$_2$, and Fv fragments.

As used herein, the term "human antibody" refers to an antibody that is encoded by an endogenous nucleic acid (e.g., rearranged human immunoglobulin heavy or light chain locus) present in a human. In some embodiments, a human antibody is collected from a human or produced in a human cell culture (e.g., human hybridoma cells). In some embodiments, a human antibody is produced in a non-human cell (e.g., a mouse or hamster cell line). In some embodiments, a human antibody is produced in a bacterial or yeast cell. In some embodiments, a human antibody is produced in a transgenic non-human animal (e.g., a bovine) containing an unrearranged or rearranged human immunoglobulin locus (e.g., heavy or light chain human immunoglobulin locus).

As used herein, the term "chimeric antibody" refers to an antibody that contains a sequence present in at least two different antibodies (e.g., antibodies from two different mammalian species such as a human and a mouse antibody). A non-limiting example of a chimeric antibody is an antibody containing the variable domain sequences (e.g., all or part of a light chain and/or heavy chain variable domain sequence) of a non-human (e.g., mouse) antibody and the constant domains of a human antibody. Additional examples of chimeric antibodies are described herein and are known in the art.

As used herein, the term "humanized antibody" refers to a non-human antibody which contains minimal sequence derived from a non-human (e.g., mouse) immunoglobulin and contains sequences derived from a human immunoglobulin. In non-limiting examples, humanized antibodies are human antibodies (recipient antibody) in which hypervariable (CDR) region residues of the recipient antibody are replaced by hypervariable (CDR) region residues from a non-human antibody (e.g., a donor antibody), e.g., a mouse, rat, or rabbit antibody, having the desired specificity, affinity, and capacity. In some embodiments, the Fv framework residues of the human immunoglobulin are replaced by corresponding non-human (e.g., mouse) immunoglobulin residues. In some embodiments, humanized antibodies may contain residues which are not found in the recipient antibody or in the donor antibody. These modifications can be made to further refine antibody performance. In some embodiments, the humanized antibody contains substantially all of at least one, and typically two, variable domains, in which all or substantially all of the hypervariable loops (CDRs) correspond to those of a non-human (e.g., mouse) immunoglobulin and all or substantially all of the framework regions are those of a human immunoglobulin. The humanized antibody can also contain at least a portion of an immunoglobulin constant region (Fc), typically, that of a human immunoglobulin. Humanized antibodies can be produced using molecular biology methods known in the art. Non-limiting examples of methods for generating humanized antibodies are described herein.

As used herein, the term "single-chain antibody" refers to a single polypeptide that contains at least two immunoglobulin variable domains (e.g., a variable domain of a mammalian immunoglobulin heavy chain or light chain) that is capable of specifically binding to an antigen. Non-limiting examples of single-chain antibodies are described herein.

As used herein, the term "multimeric antibody" refers to an antibody that contains four or more (e.g., six, eight, or ten) immunoglobulin variable domains. In some embodiments, the multimeric antibody is able to crosslink one target molecule (e.g., CTLA4) to at least one second target molecule (e.g., PD1) on the surface of a mammalian cell (e.g., a human T-cell).

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, when referring to an antibody, the phrases "specifically binding" and "specifically binds" mean that the antibody interacts with its target molecule (e.g., CTLA4) preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody. For example, an antibody that specifically binds to a CTLA4 molecule may be referred to as a CTLA4-specific antibody or an anti-CTLA4 antibody.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 23 lists CDR sequences of anti-CTLA4 antibodies 13A4, 4G12, 6D2, 7E12 and humanized antibodies thereof as defined by Kabat numbering.

FIG. 24 lists CDR sequences of anti-CTLA4 antibodies 13A4, 4G12, 6D2, 7E12 and humanized antibodies thereof as defined by Chothia numbering.

FIG. 25 lists amino acid sequences of heavy chain variable regions and light chain variable regions of humanized anti-CTLA4 antibodies.

FIG. 26 lists amino acid sequences of human CTLA4, mouse CTLA4, monkey CTLA4, and chimeric CTLA4.

FIG. 27 shows the amino acid sequence of the heavy chain and light chain variable regions of several mouse anti-hCTLA4 antibodies.

DETAILED DESCRIPTION

Figure 1:
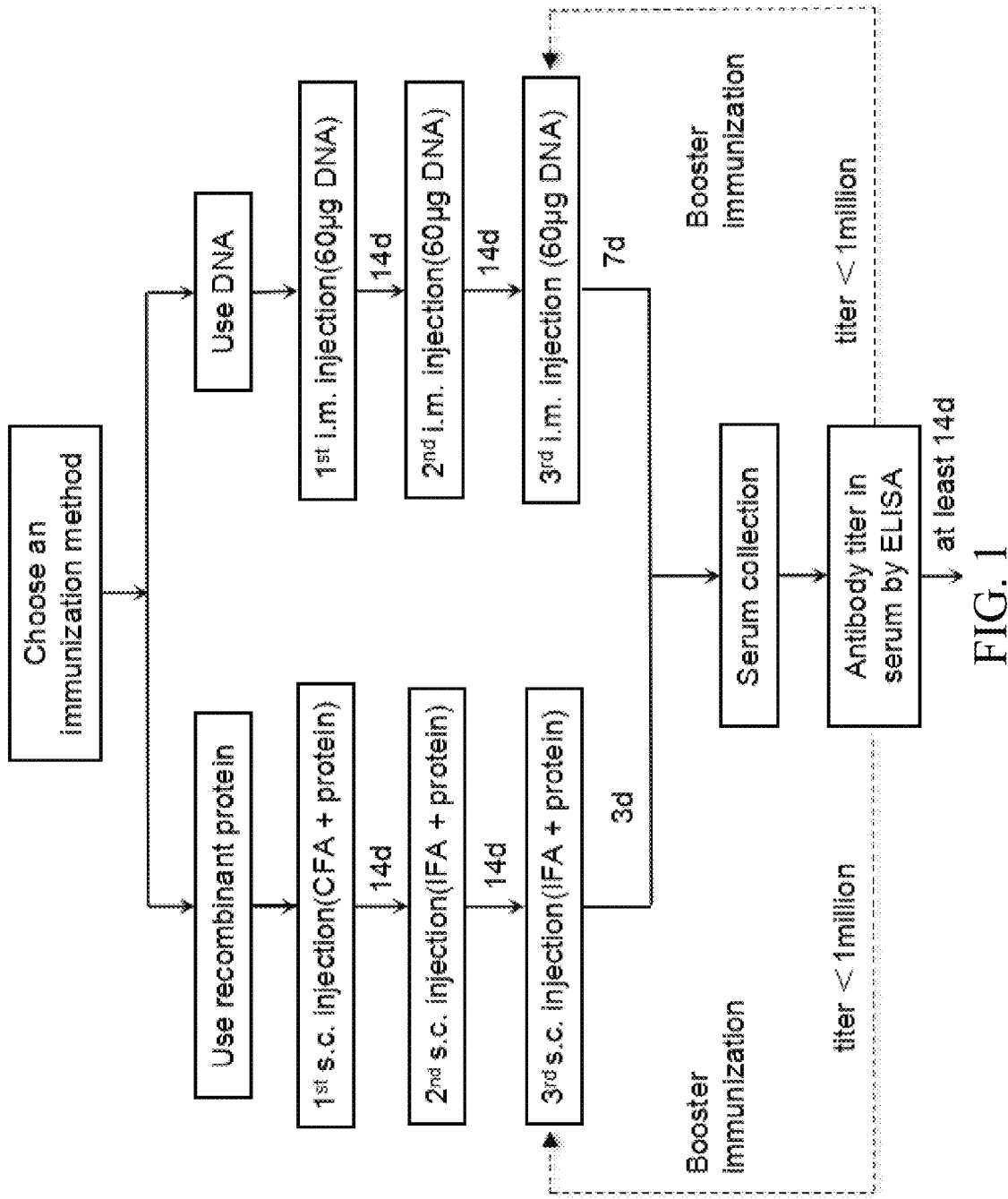
FIG. 1 is a flow chart showing the first part of an exemplary protocol of making anti-CTLA4 antibodies.

The present disclosure provides examples of antibodies, antigen-binding fragment thereof, that bind to cytotoxic T-lymphocyte-associated protein 4 (CTLA-4, CTLA4, also known as CD152).

CTLA4 is a member of the immunoglobulin superfamily that is expressed by activated T cells and transmits an inhibitory signal to T cells. It is an immune checkpoint and acts as an "off" switch when bound to CD80 or CD86, downregulating immune responses.

This disclosure also provides sequences of humanized anti-CTLA4 antibodies and methods of making and using the antibodies.

CTLA4 and Cancer

The immune system can differentiate between normal cells in the body and those it sees as "foreign," which allows the immune system to attack the foreign cells while leaving the normal cells alone. This mechanism sometimes involves proteins called immune checkpoints. Immune checkpoints are molecules in the immune system that either turn up a signal (co-stimulatory molecules) or turn down a signal.

Checkpoint inhibitors can prevent the immune system from attacking normal tissue and thereby preventing autoimmune diseases. Many tumor cells also express checkpoint inhibitors. These tumor cells escape immune surveillance by co-opting certain immune-checkpoint pathways, particularly in T cells that are specific for tumor antigens (Creelan, Benjamin C. "Update on immune checkpoint inhibitors in lung cancer." Cancer Control 21.1 (2014): 80-89). Because many immune checkpoints are initiated by ligand-receptor interactions, they can be readily blocked by antibodies against the ligands and/or their receptors.

The immune checkpoint pathway involves an elaborate series of cellular interactions that prevents excessive effector activity by T cells under normal conditions. One part of this pathway is a cell surface receptor, called cytotoxic T-lymphocyte antigen-4 (CTLA4, CD152). CTLA4 is a member of the immunoglobulin superfamily that is expressed exclusively on T-cells. CTLA4 acts to inhibit T-cell activation and is reported to inhibit helper T-cell activity and enhance regulatory T-cell immunosuppressive activity. Thus, CTLA-4 acts as an "off" switch, and turns down the immune response. Once a cytotoxic T cell becomes active, it expresses CTLA-4 on its cell surface, which then competes with the costimulatory molecule CD28 for their mutually shared ligands, B7-1 (CD80) or B7-2 (CD86) on the APC. This "yin-yang" balance holds cytotoxic activity in check, while allowing T-cell function to proceed in a self-limited manner (Creelan, Benjamin C. "Update on immune checkpoint inhibitors in lung cancer." Cancer Control 21.1 (2014): 80-89).

Many cancer cells can stimulate abnormal expression of CTLA-4 in T cells, and these CTLA-4 aberrant T cells exhibit an anergic phenotype. Thus, cancer cells may coopt the CTLA-4 pathway to evade patrolling T cells. The introduction of monoclonal antibodies that inhibit CTLA-4 can achieve consistent and durable antitumor responses in several cancers, such as melanoma. These anti-CTLA4 antibodies (e.g., tremelimumab and ipilimumab (Yervoy®)) bind to CTLA4, blocking the inhibitory signal, which allows the cytotoxic T-lymphocyte to destroy the cancer cells. Therefore, anti-CTLA4 antibodies can be used to treat cancers.

The present disclosure provides several anti-CTLA4 antibodies, antigen-binding fragments thereof, and methods of using these anti-CTLA4 antibodies and antigen-binding fragments to treat cancers.

Antibodies and Antigen Binding Fragments

The present disclosure provides anti-CTLA4 antibodies and antigen-binding fragments thereof. In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or sub-isotype including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain. The heavy chains, which each contain one variable domain (or variable region, $V_H$) and multiple constant domains (or constant regions), bind to one another via disulfide bonding within their constant domains to form the "stem" of the antibody. The light chains, which each contain one variable domain (or variable region, $V_L$) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); each of which is incorporated herein by reference in its entirety.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, Gestur, Gillian Dekkers, and Theo Rispens. "IgG subclasses and allotypes: from structure to effector functions." Frontiers in immunology 5 (2014); Irani, Vashti, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain. In some embodiments, the chimeric antigen receptor also comprises intracellular signaling domains from various costimulatory protein receptors (e.g., CD28, 41BB, ICOS). In some embodiments, the chimeric antigen receptor comprises multiple signaling domains, e.g., CD3z-CD28-41BB or CD3z-CD28-OX40, to augment potency. Thus, in one aspect, the disclosure further provides cells (e.g., T cells) that express the chimeric antigen receptors as described herein.

In some embodiments, the scFV has one heavy chain variable domain, and one light chain variable domain.

Anti-CTLA4 Antibodies and Antigen-Binding Fragments

The disclosure provides antibodies and antigen-binding fragments thereof that specifically bind to CTLA4. The antibodies and antigen-binding fragments described herein are capable of binding to CTLA4 and can inhibit CTLA4 inhibitory pathway thus increase immune response. The disclosure provides mouse anti-CTLA4 antibodies CT4-04-13A4 ("13A4"), CT4-03-4G12 ("4G12"), CT4-20-6D2 ("6D2"), and CT4-20-7E12 ("7E12"), and the humanized antibodies thereof.

The CDR sequences for 13A4, and 13A4 derived antibodies (e.g., humanized antibodies) include CDRs of the heavy chain variable domain, SEQ ID NOs: 1-3, and CDRs of the light chain variable domain, SEQ ID NOs: 4-6 as defined by Kabat numbering. The CDRs can also be defined by Chothia system. Under the Chothia numbering, the CDR sequences of the heavy chain variable domain are set forth in SEQ ID NOs: 29-31, and CDR sequences of the light chain variable domain are set forth in SEQ ID NOs: 32-34.

Similarly, the CDR sequences for 4G12, and 4G12 derived antibodies include CDRs of the heavy chain variable domain, SEQ ID NOs: 7-9, and CDRs of the light chain variable domain, SEQ ID NOs: 10-12, as defined by Kabat numbering. Under Chothia numbering, the CDR sequences of the heavy chain variable domain are set forth in SEQ ID NOs: 35-37, and CDRs of the light chain variable domain are set forth in SEQ ID NOs: 38-40.

The CDR sequences for 6D2, and 6D2 derived antibodies include CDRs of the heavy chain variable domain, SEQ ID NOs: 45-47, and CDRs of the light chain variable domain, SEQ ID NOs: 48-50, as defined by Kabat numbering. Under Chothia numbering, the CDR sequences of the heavy chain variable domain are set forth in SEQ ID NOs: 57-59, and CDRs of the light chain variable domain are set forth in SEQ ID NOs: 60-62.

The CDR sequences for 7E12, and 7E12 derived antibodies include CDRs of the heavy chain variable domain, SEQ ID NOs: 51-53, and CDRs of the light chain variable domain, SEQ ID NOs: 54-56, as defined by Kabat numbering. Under Chothia numbering, the CDR sequences of the heavy chain variable domain are set forth in SEQ ID NOs: 63-65, and CDRs of the light chain variable domain are set forth in SEQ ID NOs: 66-68.

The amino acid sequence for heavy chain variable region and light variable region of humanized antibodies are also provided. As there are different ways to humanize the mouse antibody (e.g., sequence can be substituted by different amino acids), the heavy chain and the light chain of an antibody can have more than one versions of humanized sequences. The amino acid sequences for the heavy chain variable region of humanized 13A4 antibody are set forth in SEQ ID NO: 13-17. The amino acid sequences for the light chain variable region of humanized 13A4 antibody are set forth in SEQ ID NO: 18-20. Any of these heavy chain variable region sequences (SEQ ID NO: 13-17) can be paired with any of these light chain variable region sequences (SEQ ID NO: 18-20).

Similarly, the amino acid sequences for the heavy chain variable region of humanized 4G12 antibody are set forth in SEQ ID NO: 21-24. The amino acid sequences for the light chain variable region of humanized 4G12 antibody are set forth in SEQ ID NO: 25-28. Any of these heavy chain variable region sequences (SEQ ID NO: 21-24) can be paired with any of these light chain variable region sequences (SEQ ID NO: 25-28).

As shown in FIG. 25, humanization percentage means the percentage identity of the heavy chain or light chain variable region sequence as compared to human antibody sequences in International Immunogenetics Information System (IMGT) database. The top hit means that the heavy chain or light chain variable region sequence is closer to a particular species than to other species. For example, top hit to human means that the sequence is closer to human than to other species. Top hit to human and *Macaca fascicularis* means that the sequence has the same percentage identity to the human sequence and the *Macaca fascicularis* sequence, and these percentages identities are highest as compared to the sequences of other species. In some embodiments, humanization percentage is greater than 80%, 81%, 82%, 83%, 84%, 85%, 86%, 87%, 88%, 89%, 90%, 91%, 92%, 93%, 94%, or 95%. A detailed description regarding how to determine humanization percentage and how to determine top hits is known in the art, and is described, e.g., in Jones, Tim D., et al. "The INNs and outs of antibody nonproprietary names." MAbs. Vol. 8. No. 1. Taylor & Francis, 2016, which is incorporated herein by reference in its entirety.

Furthermore, in some embodiments, the antibodies or antigen-binding fragments thereof described herein can also contain one, two, or three heavy chain variable region CDRs selected from the group of SEQ ID NOs: 1-3, SEQ ID NOs: 7-9, SEQ ID NOs: 29-31, SEQ ID NOs: 35-37, SEQ ID NOs: 45-47, SEQ ID NOs: 51-53, SEQ ID NOs: 57-59, and SEQ ID NOs: 63-65; and/or one, two, or three light chain variable region CDRs selected from the group of SEQ ID NOs: 4-6, SEQ ID NOs 10-12, SEQ ID NOs: 32-34, SEQ ID NOs 38-40, SEQ ID NOs 48-50, SEQ ID NOs 54-56, SEQ ID NOs 60-62, and SEQ ID NOs 66-68.

In some embodiments, the antibodies can have a heavy chain variable region (VH) comprising complementarity determining regions (CDRs) 1, 2, 3, wherein the CDR1 region comprises or consists of an amino acid sequence that is at least 80%, 85%, 90%, or 95% identical to a selected VH CDR1 amino acid sequence, the CDR2 region comprises or consists of an amino acid sequence that is at least 80%, 85%, 90%, or 95% identical to a selected VH CDR2 amino acid sequence, and the CDR3 region comprises or consists of an amino acid sequence that is at least 80%, 85%, 90%, or 95% identical to a selected VH CDR3 amino acid sequence, and a light chain variable region (VL) comprising CDRs 1, 2, 3, wherein the CDR1 region comprises or consists of an amino acid sequence that is at least 80%, 85%, 90%, or 95% identical to a selected VL CDR1 amino acid sequence, the CDR2 region comprises or consists of an amino acid sequence that is at least 80%, 85%, 90%, or 95% identical to a selected VL CDR2 amino acid sequence, and the CDR3 region comprises or consists of an amino acid sequence that is at least 80%, 85%, 90%, or 95% identical to a selected VL CDR3 amino acid sequence. The selected VH CDRs 1, 2, 3 amino acid sequences and the selected VL CDRs, 1, 2, 3 amino acid sequences are shown in FIG. 23 (Kabat CDR) and FIG. 24 (Chothia CDR).

In some embodiments, the antibody or an antigen-binding fragment described herein can contain a heavy chain variable domain containing one, two, or three of the CDRs of SEQ ID NO: 1 with zero, one or two amino acid insertions, deletions, or substitutions; SEQ ID NO: 2 with zero, one or two amino acid insertions, deletions, or substitutions; SEQ ID NO: 3 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 7 with zero, one or two amino acid insertions, deletions, or substitutions; SEQ ID NO: 8 with zero, one or two amino acid insertions, deletions, or substitutions; SEQ ID NO: 9 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 29 with zero, one or two amino acid insertions, deletions, or substitutions; SEQ ID NO: 30 with zero, one or two amino acid insertions, deletions, or substitutions; SEQ ID NO: 31 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 35 with zero, one or two amino acid insertions, deletions, or substitutions; SEQ ID NO: 36 with zero, one or two amino acid insertions, deletions, or substitutions; SEQ ID NO: 37 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 45 with zero, one or two amino acid insertions, deletions, or substitutions; SEQ ID NO: 46 with zero, one or two amino acid insertions, deletions, or substitutions; SEQ ID NO: 47 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 51 with zero, one or two amino acid insertions, deletions, or substitutions; SEQ ID NO: 52 with zero, one or two amino acid insertions, deletions, or substitutions; SEQ ID NO: 53 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 57 with zero, one or two amino acid insertions, deletions, or substitutions; SEQ ID NO: 58 with zero, one or two amino acid insertions, deletions, or substitutions; SEQ ID NO: 59 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 63 with zero, one or two amino acid insertions, deletions, or substitutions; SEQ ID NO: 64 with zero, one or two amino acid insertions, deletions, or substitutions; SEQ ID NO: 65 with zero, one or two amino acid insertions, deletions, or substitutions.

In some embodiments, the antibody or an antigen-binding fragment described herein can contain a light chain variable domain containing one, two, or three of the CDRs of SEQ ID NO: 4 with zero, one or two amino acid insertions, deletions, or substitutions; SEQ ID NO: 5 with zero, one or two amino acid insertions, deletions, or substitutions; SEQ ID NO: 6 with zero, one or two amino acid insertions, deletions, or substitutions.

In some embodiments, the antibody or an antigen-binding fragment described herein can contain a light chain variable domain containing one, two, or three of the CDRs of SEQ ID NO: 10 with zero, one or two amino acid insertions, deletions, or substitutions; SEQ ID NO: 11 with zero, one or two amino acid insertions, deletions, or substitutions; SEQ ID NO: 12 with zero, one or two amino acid insertions, deletions, or substitutions.

In some embodiments, the antibody or an antigen-binding fragment described herein can contain a light chain variable domain containing one, two, or three of the CDRs of SEQ ID NO: 32 with zero, one or two amino acid insertions, deletions, or substitutions; SEQ ID NO: 33 with zero, one or two amino acid insertions, deletions, or substitutions; SEQ ID NO: 34 with zero, one or two amino acid insertions, deletions, or substitutions.

In some embodiments, the antibody or an antigen-binding fragment described herein can contain a light chain variable domain containing one, two, or three of the CDRs of SEQ ID NO: 38 with zero, one or two amino acid insertions, deletions, or substitutions; SEQ ID NO: 39 with zero, one or two amino acid insertions, deletions, or substitutions; SEQ ID NO: 40 with zero, one or two amino acid insertions, deletions, or substitutions.

In some embodiments, the antibody or an antigen-binding fragment described herein can contain a light chain variable domain containing one, two, or three of the CDRs of SEQ ID NO: 48 with zero, one or two amino acid insertions, deletions, or substitutions; SEQ ID NO: 49 with zero, one or two amino acid insertions, deletions, or substitutions; SEQ ID NO: 50 with zero, one or two amino acid insertions, deletions, or substitutions.

In some embodiments, the antibody or an antigen-binding fragment described herein can contain a light chain variable domain containing one, two, or three of the CDRs of SEQ ID NO: 54 with zero, one or two amino acid insertions, deletions, or substitutions; SEQ ID NO: 55 with zero, one or two amino acid insertions, deletions, or substitutions; SEQ ID NO: 56 with zero, one or two amino acid insertions, deletions, or substitutions.

In some embodiments, the antibody or an antigen-binding fragment described herein can contain a light chain variable domain containing one, two, or three of the CDRs of SEQ ID NO: 60 with zero, one or two amino acid insertions, deletions, or substitutions; SEQ ID NO: 61 with zero, one or two amino acid insertions, deletions, or substitutions; SEQ ID NO: 62 with zero, one or two amino acid insertions, deletions, or substitutions.

In some embodiments, the antibody or an antigen-binding fragment described herein can contain a light chain variable domain containing one, two, or three of the CDRs of SEQ ID NO: 66 with zero, one or two amino acid insertions, deletions, or substitutions; SEQ ID NO: 67 with zero, one or two amino acid insertions, deletions, or substitutions; SEQ ID NO: 68 with zero, one or two amino acid insertions, deletions, or substitutions.

The insertions, deletions, and substitutions can be within the CDR sequence, or at one or both terminal ends of the CDR sequence.

The disclosure also provides antibodies or antigen-binding fragments thereof that binds to CTLA4. The antibodies or antigen-binding fragments thereof contain a heavy chain variable region (VH) comprising or consisting of an amino acid sequence that is at least 80%, 85%, 90%, or 95% identical to a selected VH sequence, and a light chain variable region (VL) comprising or consisting of an amino acid sequence that is at least 80%, 85%, 90%, or 95% identical to a selected VL sequence. In some embodiments, the selected VH sequence is SEQ ID NO: 13, 14, 15, 16, 17, or 69, and the selected VL sequence is SEQ ID NO: 18, 19, 20, or 70. In some embodiments, the selected VH sequence is SEQ ID NO: 21, 22, 23, 24, or 71, and the selected VL sequence is SEQ ID NO: 25, 26, 27, 28, or 72. In some embodiments, the selected VH sequence is SEQ ID NO: 73, and the selected VL sequence is SEQ ID NO: 74. In some embodiments, the selected VH sequence is SEQ ID NO: 75, and the selected VL sequence is SEQ ID NO: 76.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The disclosure also provides nucleic acid comprising a polynucleotide encoding a polypeptide comprising an immunoglobulin heavy chain or an immunoglobulin heavy chain. The immunoglobulin heavy chain or immunoglobulin light chain comprises CDRs as shown in FIG. 23 or FIG. 24, or have sequences as shown in FIG. 25 or FIG. 27. When the polypeptides are paired with corresponding polypeptide (e.g., a corresponding heavy chain variable region or a corresponding light chain variable region), the paired polypeptides bind to CTLA4.

The anti-CTLA4 antibodies and antigen-binding fragments can also be antibody variants (including derivatives and conjugates) of antibodies or antibody fragments and multi-specific (e.g., bi-specific) antibodies or antibody fragments. Additional antibodies provided herein are polyclonal, monoclonal, multi-specific (multimeric, e.g., bi-specific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., IgG1, IgG2, IgG3, IgG4, IgA1, and IgA2), or subclass. In some embodiments, the antibody or antigen-binding fragment thereof is an IgG antibody or antigen-binding fragment thereof.

Fragments of antibodies are suitable for use in the methods provided so long as they retain the desired affinity and specificity of the full-length antibody. Thus, a fragment of an antibody that binds to CTLA-4 will retain an ability to bind to CTLA-4. An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the VH and VL domains (or regions) of antibody, wherein these domains are present in a single polypeptide chain. Generally, the Fv polypeptide further comprises a polypeptide linker between the VH and VL domains, which enables the scFv to form the desired structure for antigen binding.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites, which fragments comprise a VH connected to a VL in the same polypeptide chain (VH and VL). By using a linker that is too short to allow pairing between the two domains on the same chain, the domains are forced to pair with the complementary domains of another chain and create two antigen-binding sites.

Linear antibodies comprise a pair of tandem Fd segments (VH-CH1-VH-CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life.

Multimerization of antibodies may be accomplished through natural aggregation of antibodies or through chemical or recombinant linking techniques known in the art. For example, some percentage of purified antibody preparations (e.g., purified $IgG_1$ molecules) spontaneously form protein aggregates containing antibody homodimers and other higher-order antibody multimers.

Alternatively, antibody homodimers may be formed through chemical linkage techniques known in the art. For example, heterobifunctional crosslinking agents including, but not limited to SMCC (succinimidyl 4-(maleimidomethyl)cyclohexane-1-carboxylate) and SATA (N-succinimidyl S-acethylthio-acetate) can be used to form antibody multimers. An exemplary protocol for the formation of antibody homodimers is described in Ghetie et al. (*Proc. Natl. Acad. Sci. U.S.A.* 94: 7509-7514, 1997). Antibody homodimers can be converted to Fab'$_2$ homodimers through digestion with pepsin. Another way to form antibody homodimers is through the use of the autophilic T15 peptide described in Zhao et al. (*J. Immunol.* 25:396-404, 2002).

In some embodiments, the multi-specific antibody is a bi-specific antibody. Bi-specific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

Bi-specific antibodies include cross-linked or "heteroconjugate" antibodies. For example, one of the antibodies in the heteroconjugate can be coupled to avidin and the other to biotin. Heteroconjugate antibodies can also be made using any convenient cross-linking methods. Suitable cross-linking agents and cross-linking techniques are well known in the art and are disclosed in U.S. Pat. No. 4,676,980, which is incorporated herein by reference in its entirety.

Methods for generating bi-specific antibodies from antibody fragments are also known in the art. For example, bi-specific antibodies can be prepared using chemical linkage. Brennan et al. (*Science* 229:81, 1985) describes a procedure where intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' TNB derivatives is then reconverted to the Fab' thiol by reduction with mercaptoethylamine, and is mixed with an equimolar amount of another Fab' TNB derivative to form the bi-specific antibody.

Any of the antibodies or antigen-binding fragments described herein may be conjugated to a stabilizing molecule (e.g., a molecule that increases the half-life of the antibody or antigen-binding fragment thereof in a subject or in solution). Non-limiting examples of stabilizing molecules include: a polymer (e.g., a polyethylene glycol) or a protein (e.g., serum albumin, such as human serum albumin). The conjugation of a stabilizing molecule can increase the half-life or extend the biological activity of an antibody or an antigen-binding fragment in vitro (e.g., in tissue culture or when stored as a pharmaceutical composition) or in vivo (e.g., in a human).

Antibody Characteristics

The antibodies or antigen-binding fragments thereof described herein can block the binding between CTAL4 and CD80, and/or the binding between CTLA4 and CD86. By blocking the binding between CTAL4 and CD80, and/or the binding between CTLA4 and CD86, anti-CTLA4 antibodies disrupts the CTLA4 inhibitory pathway and upregulates the immune response.

In some implementations, the antibody (or antigen-binding fragments thereof) specifically binds to CTLA4 (e.g., human CTLA4, monkey CLTA4, mouse CTLA4, and/or chimeric CTLA4) with a dissociation constant (Kd) of less than $1\times10^{-6}$ M, less than $1\times10^{-7}$ M, less than $1\times10^{-8}$ M, less than 1×10$^{-9}$ M, or less than 1×10$^{-10}$ M. In some embodiments, the Kd is less than 20 nM, 15 nM, 10 nM, 9 nM, 8 nM, 7 nM, 6 nM, 5 nM, 4 nM, 3 nM, 2 nM, or 1 nM.

In some embodiments, Kd is greater than 1×10$^{-7}$ M, greater than 1×10$^{-8}$ M, greater than 1×10$^{-9}$ M, greater than 1×10$^{-10}$ M, greater than 1×10$^{-11}$ M, or greater than 1×10$^{-12}$ M.

General techniques for measuring the affinity of an antibody for an antigen include, e.g., ELISA, RIA, and surface plasmon resonance (SPR). In some embodiments, the antibody binds to human CTLA4 (SEQ ID NO: 41), monkey CTLA4 (e.g., rhesus macaque CTLA4, SEQ ID NO: 43), chimeric CTLA4 (SEQ ID NO: 44), and/or mouse CTLA4 (SEQ ID NO: 42). In some embodiments, the antibody does not bind to human CTLA4 (SEQ ID NO: 41), monkey CTLA4 (e.g., rhesus macaque CTLA4, SEQ ID NO: 43), chimeric CTLA4 (SEQ ID NO: 44), and/or mouse CTLA4 (SEQ ID NO: 42).

In some embodiments, the antibody has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the antibody has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$TGI\ (\%) = [1 - (Ti - T0)/(Vi - V0)] \times 100$$

Ti is the average tumor volume in the treatment group on day i. T0 is the average tumor volume in the treatment group on day zero. Vi is the average tumor volume in the control group on day i. V0 is the average tumor volume in the control group on day zero.

Methods of Making Anti-CTLA4 Antibodies

An isolated fragment of human CTLA4 can be used as an immunogen to generate antibodies using standard techniques for polyclonal and monoclonal antibody preparation. Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence of CTLA4 and encompasses an epitope of the protein such that an antibody raised against the peptide forms a specific immune complex with the protein. As described above, the full length sequence of human CTLA4 is known in the art (SEQ ID NO: 41).

An immunogen typically is used to prepare antibodies by immunizing a suitable subject (e.g., human or transgenic animal expressing at least one human immunoglobulin locus). An appropriate immunogenic preparation can contain, for example, a recombinantly-expressed or a chemically-synthesized polypeptide (e.g., a fragment of human CTLA4). The preparation can further include an adjuvant, such as Freund's complete or incomplete adjuvant, or a similar immunostimulatory agent.

Polyclonal antibodies can be prepared as described above by immunizing a suitable subject with a CTLA4 polypeptide, or an antigenic peptide thereof (e.g., part of CTLA4) as an immunogen. The antibody titer in the immunized subject can be monitored over time by standard techniques, such as with an enzyme-linked immunosorbent assay (ELISA) using the immobilized CTLA4 polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, NY). Hybridoma cells producing a monoclonal antibody are detected by screening the hybridoma culture supernatants for antibodies that bind the polypeptide or epitope of interest, e.g., using a standard ELISA assay.

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein, e.g., CTLA4. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

A humanized antibody, typically has a human framework (FR) grafted with non-human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed by e.g., substituting rodent CDRs or CDR sequences for the corresponding sequences of a human antibody. These methods are described in e.g., Jones et al., Nature, 321:522-525 (1986); Riechmann et al., Nature, 332:323-327 (1988); Verhoeyen et al., Science, 239:1534-1536 (1988); each of which is incorporated by reference herein in its entirety. Accordingly, "humanized" antibodies are chimeric antibodies wherein substantially less than an intact human V domain has been substituted by the corresponding sequence from a non-human species. In practice, humanized antibodies are typically mouse antibodies in which some CDR residues and some FR residues are substituted by residues from analogous sites in human antibodies.

The choice of human VH and VL domains to be used in making the humanized antibodies is very important for reducing immunogenicity. According to the so-called "best-fit" method, the sequence of the V domain of a mouse antibody is screened against the entire library of known human-domain sequences. The human sequence which is closest to that of the mouse is then accepted as the human FR for the humanized antibody (Sims et al., J. Immunol., 151:2296 (1993); Chothia et al., J. Mol. Biol., 196:901 (1987)).

It is further important that antibodies be humanized with retention of high specificity and affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Ordinarily, amino acid sequence variants of the human, humanized, or chimeric anti-CTLA4 antibody will contain an amino acid sequence having at least 75%, 80%, 85%, 90%, 95%, 96%, 97%, 98%, or 99% percent identity with a sequence present in the light or heavy chain of the original antibody.

Identity or homology with respect to an original sequence is usually the percentage of amino acid residues present within the candidate sequence that are identical with a sequence present within the human, humanized, or chimeric anti-CTLA4 antibody or fragment, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

Additional modifications to the anti-CTLA4 antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. (*Cancer Res.* 53:2560-2565, 1993). Alternatively, an antibody can be engineered which has dual Fc regions (see, for example, Stevenson et al., *Anti-Cancer Drug Design* 3:219-230, 1989).

In some embodiments, a covalent modification can be made to the anti-CTLA4 antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

Recombinant Vectors

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant antibody polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some implementations, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher- Hoch et al., 1989, Proc. Natl. Acad. Sci. USA 86:317-321; Flexner et al., 1989, Ann. N.Y. Acad Sci. 569:86-103; Flexner et al., 1990, Vaccine, 8:17-21; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner-Biotechniques, 6:616-627, 1988; Rosenfeld et al., 1991, Science, 252:431-434; Kolls et al., 1994, Proc. Natl. Acad. Sci. USA, 91:215-219; Kass-Eisler et al., 1993, Proc. Natl. Acad. Sci. USA, 90:11498-11502; Guzman et al., 1993, Circulation, 88:2838-2848; and Guzman et al., 1993, Cir. Res., 73:1202-1207. Techniques for incorporating DNA into such expression systems are well known to those of ordinary skill in the art. The DNA may also be "naked," as described, for example, in Ulmer et al., 1993, Science, 259:1745-1749, and Cohen, 1993, Science, 259:1691-1692. The uptake of naked DNA may be increased by coating the DNA onto biodegradable beads that are efficiently transported into the cells.

For expression, the DNA insert comprising an antibody-encoding or polypeptide-encoding polynucleotide disclosed herein can be operatively linked to an appropriate promoter (e.g., a heterologous promoter), such as the phage lambda PL promoter, the *E. coli* lac, trp and tac promoters, the SV40 early and late promoters and promoters of retroviral LTRs, to name a few. Other suitable promoters are known to the skilled artisan. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces,* and *Salmonella typhimurium* cells; fungal cells, such as yeast cells; insect cells such as *Drosophila* S2 and *Spodoptera* Sf9 cells; animal cells such as CHO, COS, Bowes melanoma, and HK 293 cells; and plant cells. Appropriate culture mediums and conditions for the host cells described herein are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWL-NEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast *Saccharomyces cerevisiae*, a number of vectors containing constitutive or inducible promoters such as alpha factor, alcohol oxidase, and PGH may be used. For reviews, see Ausubel et al. (1989) CURRENT PROTOCOLS IN MOLECULAR BIOLOGY, John Wiley & Sons, New York, N.Y, and Grant et al., *Methods Enzymol.,* 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY (1986).

Transcription of DNA encoding an antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., antibody) can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

Methods of Treatment

The antibodies or antibody or antigen-binding fragments thereof of the present disclosure can be used for various therapeutic purposes. In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of an antibody or antigen-binding fragment thereof disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer.

In some embodiments, the compositions and methods disclosed herein can be used for treatment of patients at risk for a cancer. Patients with cancer can be identified with various methods known in the art.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the antibody, antigen binding fragment, antibody-encoding polynucleotide, vector comprising the polynucleotide, and/or compositions thereof is to be administered, a severity of symptoms and a route of administration, and thus administration can be determined on an individual basis.

An effective amount can be administered in one or more administrations. By way of example, an effective amount of an antibody or an antigen binding fragment is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of an antibody or antigen binding fragment may vary, depending on, inter alia, patient history as well as other factors such as the type (and/or dosage) of antibody used.

Effective amounts and schedules for administering the antibodies, antibody-encoding polynucleotides, and/or compositions disclosed herein may be determined empirically, and making such determinations is within the skill in the art. Those skilled in the art will understand that the dosage that must be administered will vary depending on, for example, the mammal that will receive the antibodies, antibody-encoding polynucleotides, and/or compositions disclosed herein, the route of administration, the particular type of antibodies, antibody-encoding polynucleotides, antigen binding fragments, and/or compositions disclosed herein used and other drugs being administered to the mammal. Guidance in selecting appropriate doses for antibody or antigen binding fragment can be found in the literature on therapeutic uses of antibodies and antigen binding fragments, e.g., Handbook of Monoclonal Antibodies, Ferrone et al., eds., Noges Publications, Park Ridge, N.J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of an antibody is 0.01 mg/kg to 100 mg/kg. In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.1 mg/kg, 0.05 mg/kg, or 0.01 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg.

In any of the methods described herein, the at least one antibody, antigen-binding fragment thereof, or pharmaceutical composition (e.g., any of the antibodies, antigen-binding fragments, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different antibodies and/or antigen-binding fragments are administered in the same composition (e.g., a liquid composition). In some embodiments, at least one antibody or antigen-binding fragment and at least one additional therapeutic agent are administered in the same composition (e.g., a liquid composition). In some embodiments, the at least one antibody or antigen-binding fragment and the at least one additional therapeutic agent are administered in two different compositions (e.g., a liquid composition containing at least one antibody or antigen-binding fragment and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to, or after administering the at least one antibody, antigen-binding antibody fragment, or pharmaceutical composition (e.g., any of the antibodies, antigen-binding antibody fragments, or pharmaceutical compositions described herein). In some embodiments, the one or more additional therapeutic agents and the at least one antibody, antigen-binding antibody fragment, or pharmaceutical composition (e.g., any of the antibodies, antigen-binding antibody fragments, or pharmaceutical compositions described herein) are administered to the subject such that there is an overlap in the bioactive period of the one or more additional therapeutic agents and the at least one antibody or antigen-binding fragment (e.g., any of the antibodies or antigen-binding fragments described herein) in the subject.

In some embodiments, the subject can be administered the at least one antibody, antigen-binding antibody fragment, or pharmaceutical composition (e.g., any of the antibodies, antigen-binding antibody fragments, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years). A skilled medical professional may determine the length of the treatment period using any of the methods described herein for diagnosing or following the effectiveness of treatment (e.g., the observation of at least one symptom of cancer). As described herein, a skilled medical professional can also change the identity and number (e.g., increase or decrease) of antibodies or antigen-binding antibody fragments (and/or one or more additional therapeutic agents) administered to the subject and can also adjust (e.g., increase or decrease) the dosage or frequency of administration of at least one antibody or antigen-binding antibody fragment (and/or one or more additional therapeutic agents) to the subject based on an assessment of the effectiveness of the treatment (e.g., using any of the methods described herein and known in the art).

Pharmaceutical Compositions and Routes of Administration

Also provided herein are pharmaceutical compositions that contain at least one (e.g., one, two, three, or four) of the antibodies or antigen-binding fragments described herein. Two or more (e.g., two, three, or four) of any of the antibodies or antigen-binding fragments described herein can be present in a pharmaceutical composition in any combination. The pharmaceutical compositions may be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfate, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the antibody or antigen-binding fragment thereof can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the antibodies or antigen-binding fragments described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) antibodies or antigen-binding fragments thereof (e.g., any of the antibodies or antibody fragments described herein) will be an amount that treats the disease in a subject (e.g., kills cancer cells) in a subject (e.g., a human subject identified as having cancer), or a subject identified as being at risk of developing the disease (e.g., a subject who has previously developed cancer but now has been cured), decreases the severity, frequency, and/or duration of one or more symptoms of a disease in a subject (e.g., a human). The effectiveness and dosing of any of the antibodies or antigen-binding fragments described herein can be determined by a health care professional or veterinary professional using methods known in the art, as well as by the observation of one or more symptoms of disease in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the antibodies or antigen-binding fragments described herein per kilogram of the subject's weight (e.g., about 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; or about 1 µg/kg to about 50 µg/kg). While these doses cover a broad range, one of ordinary skill in the art will understand that therapeutic agents, including antibodies and antigen-binding fragments thereof, vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the antibody or antibody fragment in vivo.

The pharmaceutical compositions can be included in a container, pack, or dispenser together with instructions for administration.

EXAMPLES

The invention is further described in the following examples, which do not limit the scope of the invention described in the claims.

Example 1. Generating Mouse Anti-hCTLA4 Antibodies

Figure 2:
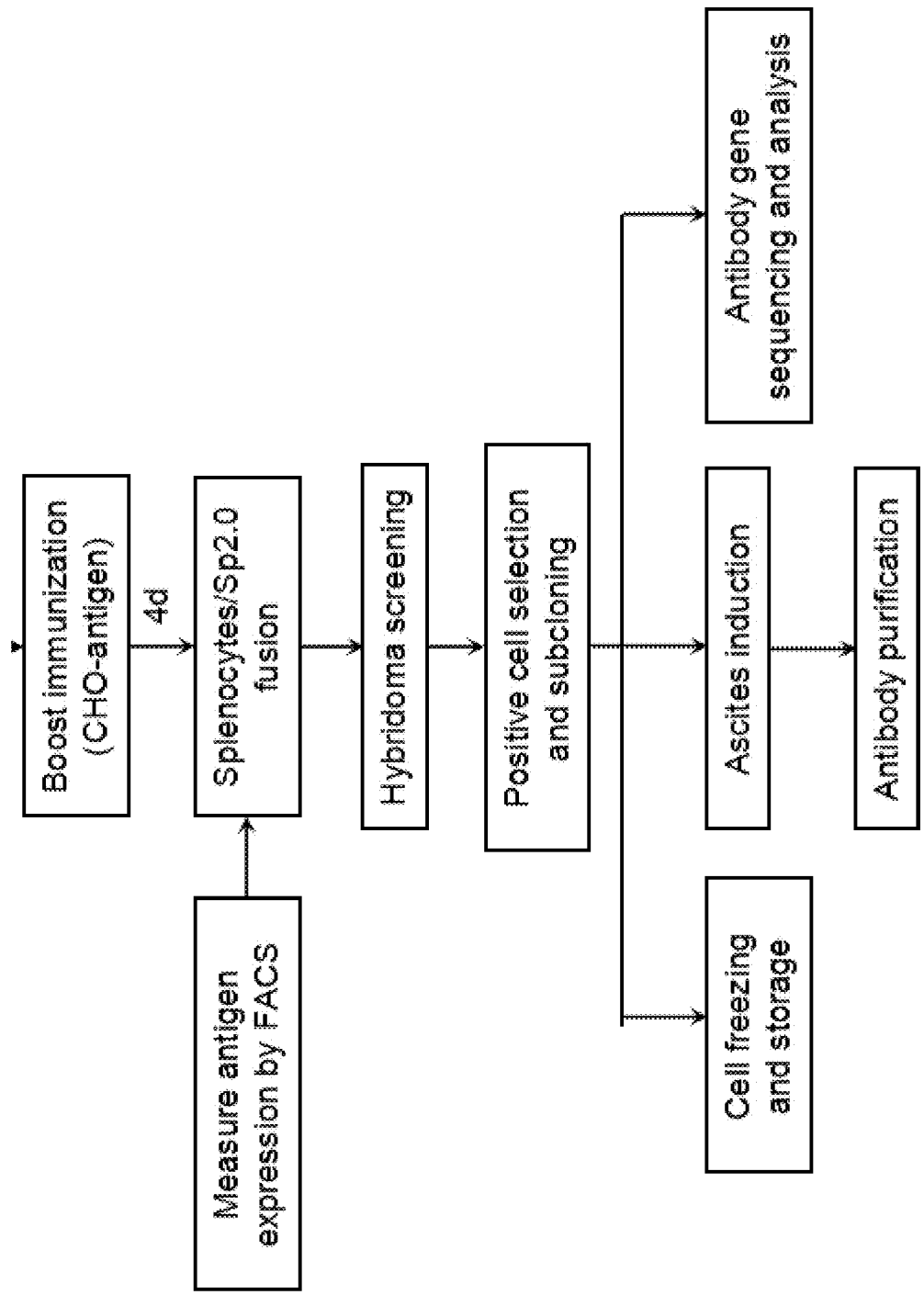
FIG. 2 is a flow chart showing the second part of an exemplary protocol of making anti-CTLA4 antibodies.

To generate mouse antibodies against human CTLA4 (hCTLA4; SEQ ID NO: 41), 6-8 weeks old female BALB/c mice were immunized with human CTLA4. Anti-hCTLA4 antibodies were collected by the methods as described below (FIG. 1 and FIG. 2).

Immunization of Mice 6-8 weeks old female BALB/c mice were immunized with his-tagged human CTLA4 proteins at 20 ug/mouse at a concentration of 100 ug/ml. The his-tagged human CTLA4 proteins were emulsified with adjuvant and injected at four positions on the back of the mice. For the first subcutaneous (s.c.) injection, the diluted antigen was emulsified with Complete Freund's Adjuvant (CFA) in equal volume. In the following subcutaneous injections, the protein was emulsified with Incomplete Freund's Adjuvant (IFA) in equal volume. Three days after the third injection or the booster immunization, blood (serum) was collected and analyzed for antibody titer using ELISA.

In another experiment, 6-8 weeks old female BALB/c mice were immunized by injecting the expression plasmid encoding human CTLA4 into the mice. The plasmids encoding the antigen were injected into the tibialis anterior muscle (intramuscular injection; i.m. injection) of the mice by using gene guns at the concentration of 1000 ug/ul at 60 ug per mouse. At least four injections were performed with at least 14 days between each injection. Blood (serum) was collected seven days after the last immunization and the serum was tested for antibody titer by ELISA.

Procedures to enhance immunization were also performed at least fourteen days after the previous immunization (either by injecting the plasmid or by injecting the proteins). CHO cells that express CTLA4 antigen on the surface were intravenously injected into the mice through tail veins. Spleen was then collected four days after the injection.

Fusion of SP2/0 Cells and Spleen Cells

Spleen tissues were grinded. Spleen cells were first selected by CD3c Microbeads and Anti-Mouse IgM Microbeads, and then fused with SP2/0 cells. The cells were then plated in 96-well plates with hypoxanthine-aminopterin-thymidine (HAT) medium.

Primary Screening of Hybridoma

Primary screening of the hybridoma supernatant in the 96-well plates was performed using Fluorescence-Activated Cell Sorting (FACS) pursuant to standard procedures. Chinese hamster ovary (CHO) cells were added to 96-well plates ($2\times10^4$ cells per well) before the screening. 50 ul of supernatant was used. The antibodies that were used in experiments were
(1) Fluorescein (FITC)-conjugated AffiniPure F(ab)$_2$ Fragment Goat Anti-Mouse IgG, Fcγ Fragment Specific, and
(2) Alexa Fluor® 647-conjugated AffiniPure F(ab)2 Fragment Goat Anti-Human IgG, Fcγ Fragment Specific.

Sub-Cloning

Sub-cloning was performed using ClonePix® 2 Mammalian Colony Picker. In short, the positive wells identified during the primary screening were transferred to semisolid medium, and IgG positive clones were identified and tested. FITC anti-mouse IgG Fc antibody was used.

Ascites Fluid Antibodies $1\times10^6$ positive hybridoma cells were injected intraperitoneally to B-NDG® mice (Beijing Biocytogen, Beijing, China). Monoclonal antibodies were produced by growing hybridoma cells within the peritoneal cavity of the mouse. The hybridoma cells multiplied and produced ascites fluid in the abdomens of the mice. The fluid contained a high concentration of antibody which can be harvested for later use.

Purification of Antibodies

Antibodies in ascites fluid were purified using GE AKTA protein chromatography (GE Healthcare, Chicago, Illinois, United States). CT4-04-13A4 ("13A4"), CT4-03-4G12 ("4G12"), CT4-20-6D2 ("6D2"), and CT4-20-7E12 ("7E12") were among the mice antibodies produced by the methods described above. The amino acid sequences of the heavy chain and light chain variable regions of these antibodies are provided in FIG. 27

Example 2. Humanization of the Mice Antibodies

The starting point for humanization was the mouse antibodies (e.g., 13A4 and 4G12). The amino acid sequences for the heavy chain variable region and the light chain variable region of these mouse antibodies were determined. Five humanized heavy chain variable region variants (SEQ ID NOs: 13-17) and three humanized light chain variable region variants (SEQ ID NOs: 18-20) for 13A4 were constructed containing different permutations of substitutions (FIG. 25). The heavy chain and light chain CDR1, CDR2, and CDR3 amino acid sequences for humanized 13A4 were shown in SEQ ID NO: 1-6 (Kabat numbering) or SEQ ID NO: 29-34 (Chothia numbering).

Four humanized heavy chain variable region variants (SEQ ID NOs: 21-24) and four humanized light chain variable region variants (SEQ ID NOs: 25-28) for 4G12 were constructed containing different permutations of substitutions (FIG. 25). The heavy chain and light chain CDR1, CDR2, and CDR3 amino acid sequences for humanized 4G12 were shown in SEQ ID NO: 7-12 (Kabat numbering) or SEQ ID NO: 35-40 (Chothia numbering).

These humanized antibodies were generated with standard procedures and facilitated with the use of BioLuminate® 1.0 (Schrodinger, Shanghai, China).

Example 3. In Vitro Testing of the Mouse Anti-hCTLA4 Antibodies: Blocking the CTLA4 Binding of CD80 and CD86

Blocking assays were performed to determine whether anti-CTLA4 antibodies can block the binding between CTLA4 and CD80, and the binding between CTLA4 and CD86.

Anti-CTLA4 antibodies were collected from mouse ascites fluid, and were purified by chromatography. 25 ul CHO cells transiently transfected with human CTLA4 were added to each well in a plate. The purified antibodies were titrated to final concentrations of 50, 5, 0.5, 0.05, 0.005 ug/ml. The titrated antibodies were added to each well at 25 ul per well at 4° C. and incubated for 30 minutes.

Biotin-hCD80 or Biotin-hCD86 was titrated to 0.4 ug/ml. 50 ul of the ligand solution was added to each well, making the final concentration of Biotin-hCD80 or Biotin-hCD86 0.2 ug/ml. The cells with Biotin-hCD80 or Biotin-hCD86 were incubated at 4° C. for 15 minutes.

After being washed with phosphate-buffered saline (PBS), 50 ul of anti-mouse IgG Fc antibody fluorescein isothiocyanate conjugate (IgG Fc-FITC) and streptavidin-Phycoerythrin (streptavidin-PE) were added at 1:100 dilution into each well at 4° C. and incubated for 15 minutes, followed by PBS wash. The signals for FITC and PE were determined by flow cytometry.

Figure 3:
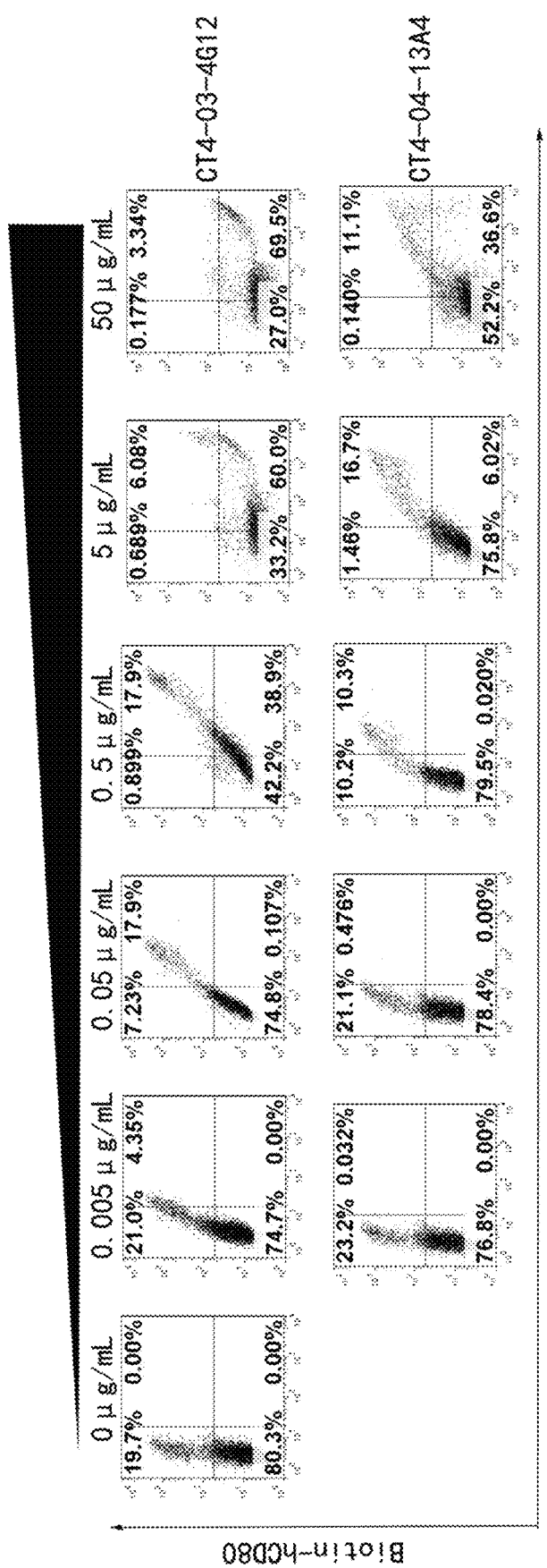
FIG. 3 is a set of flow cytometry graphs showing the anti-CTLA4 antibodies block the binding between CTLA4 and CD80.

As shown in FIG. 3, when the concentration of the mouse anti-hCTLA4 antibody (CT4-04-13A4 and CT4-03-4G12) increased, the signal for PE decreased, suggesting that the binding between human CTLA4 and Biotin-hCD80 was blocked by CT4-04-13A4 and CT4-03-4G12 antibodies.

Figure 4:
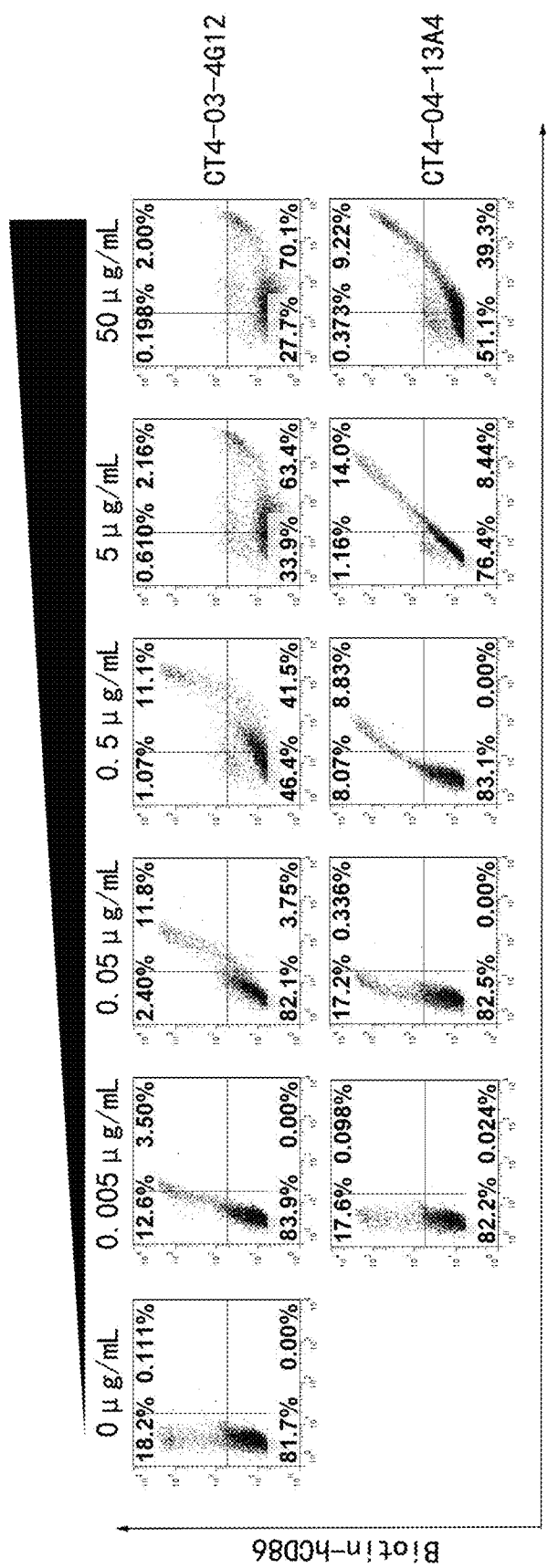
FIG. 4 is a set of flow cytometry graphs showing the anti-CTLA4 antibodies block the binding between CTLA4 and CD86.

Similarly, in FIG. 4, when the concentration of the anti-hCTLA4 antibody (CT4-04-13A4 and CT4-03-4G12) increased, the signal for PE decreased, suggesting that the binding between human CTLA4 and Biotin-hCD86 was blocked by CT4-04-13A4 and CT4-03-4G12 antibodies.

Example 4. Cross-Reactivity of Chimeric Anti-hCTLA Antibodies Against Monkey, Mouse, and Human-Mouse Chimeric CTLA4

CHO cells were transfected with rhesus macaque CTLA4 (rmCTLA4, SEQ ID NO: 43), mouse CTLA4 (mCTLA4, SEQ ID NO: 42), and chimeric (mouse and human) CTLA4 (chiCTLA4, SEQ ID NO: 44).

25 ul CHO cells were added to each well. 25 ul purified chimeric anti-hCTLA antibodies (1 ug/ml) (CT4-03-4G12-mHvKv-IgG1 and CT4-04-13A4-mHvKv-IgG1) were added to each well and were incubated at 4° C. for 30 minutes. CT4-03-4G12-mHvKv-IgG1 and CT4-04-13A4- mHvKv-IgG1 are chimeric anti-hCTLA antibodies. CT4-03-4G12-mHvKv-IgG1 has heavy chain variable domain and light chain variable domain from the mouse antibody 4G12, and human IgG1 antibody constant domains (CL, CH1, CH2, CH3). Similarly, CT4-04-13A4-mHvKv-IgG1 has heavy chain variable domain and light chain variable domain from the mouse antibody 13A4, and human IgG1 antibody constant domains (CL, CH1, CH2, CH3).

After being washed with PBS (1200 rmp, 5 min) twice, 50 ul of anti-human IgG Fc antibody fluorescein isothiocyanate conjugate (IgG Fc-FITC) was added at 1:100 dilution into each well and was incubated at 4° C. for 30 minutes, followed by PBS wash. The signals for FITC were determined by flow cytometry.

Figure 5:
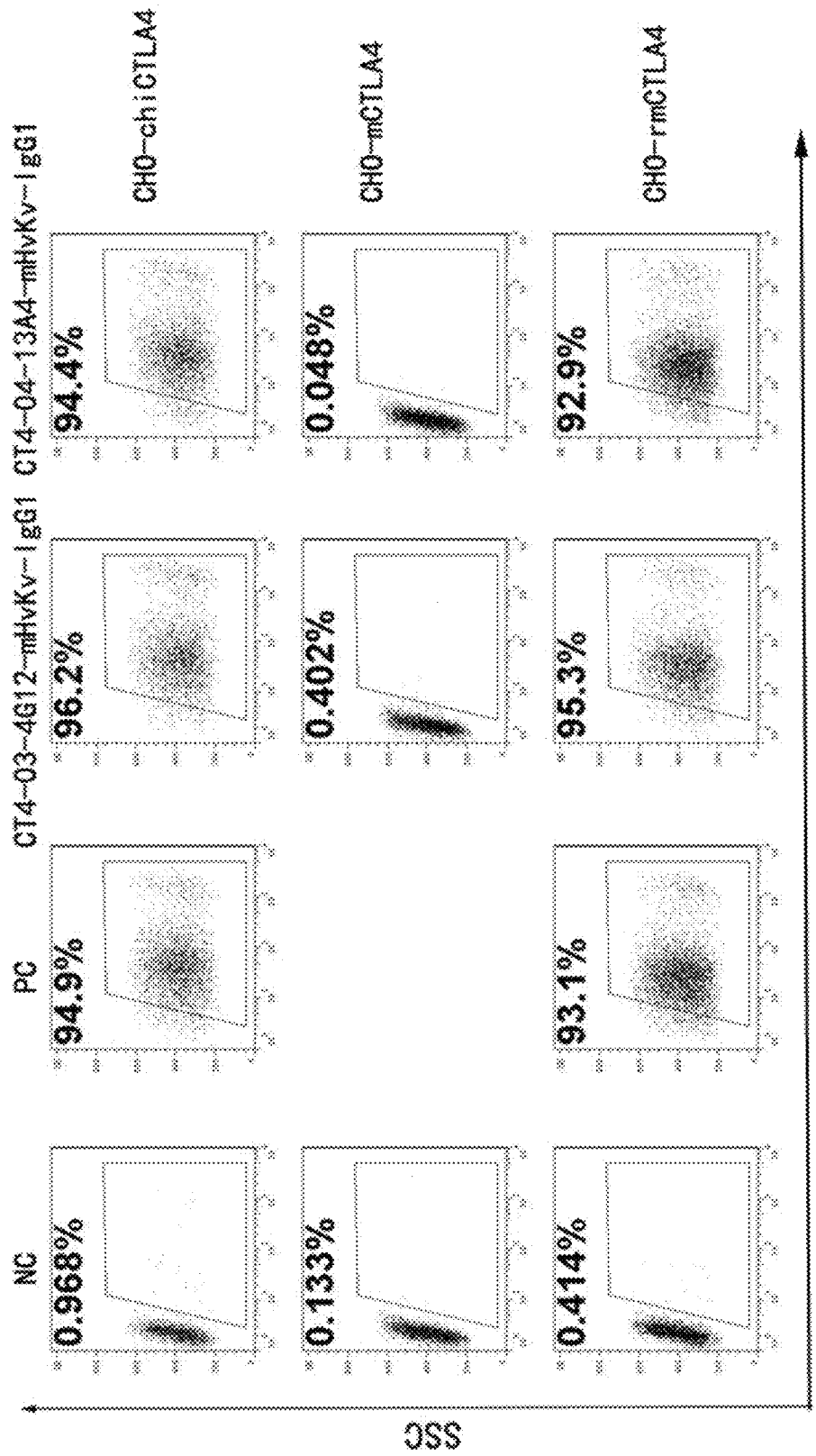
FIG. 5 is a set of graphs showing flow cytometry results of anti-CTLA4 antibodies' cross-reactivity against monkey (rmCTLA4), mouse (mCTLA4), and human-mouse chimeric CTLA4 (chiCTLA4).

As shown in FIG. 5, CT4-04-13A4-mHvKv-IgG1 did not cross react with mouse CTLA4, and had strong cross reactivity with rmCTLA4 and chimeric CTLA4. Similarly, CT4-03-4G12-mHvKv-IgG1 did not cross react with mouse CTLA4, and had strong cross reactivity with rmCTLA4 and chimeric CTLA4. In FIG. 5, NC stands for negative control, and PC stands for positive control.

Example 5. In Vivo Testing of Mouse Anti-hCTLA4 Antibodies

In order to test the anti-hCTLA4 antibodies in vivo and to predict the effects of these antibodies in human body, a CTLA-4 humanized mouse model was generated. The CTLA4 humanized mouse model was engineered to express a chimeric CTLA4 protein (SEQ ID NO: 44) wherein a part of the extracellular region of the mouse CTLA4 protein was replaced by the human CTLA4 extracellular region. The amino acid residues from position 41-143 of SEQ ID NO: 44 are derived from human CTLA4. The humanized mouse model (B-hCTLA-4 humanized mice) can provide a new tool for testing new therapeutic treatments in a clinical setting by significantly decreasing the difference between clinical outcome in human and in ordinary mice expressing mouse CTLA4.

The anti-hCTLA4 antibodies were tested to demonstrate their effect on tumor growth in vivo in a model of colon carcinoma. MC-38 cancer tumor cells (colon adenocarcinoma cell) were injected subcutaneously in B-hCTLA-4 humanized mice. When the tumors in the mice reached a volume of 150±50 mm$^3$, the mice were randomly placed into different groups based on the volume of the tumor. The mice were then injected intravenously with PBS and anti-hCTLA4 antibodies. The antibody was given every three days for a total of 15 days (6 injections in total). The injected volume was calculated based on the weight of the mouse at 10 ul/g. The length of the long axis and short axis of the tumor was measured twice every week, and the volume of the tumor was calculated as 0.5×(long axis)×(short axis)$^2$. The weight of the mice was also measured before the injection, when the mice were placed into different groups (before the first antibody injection), twice a week during the antibody injection period, and before euthanization.

The tumor growth inhibition percentage (TGI %) was calculated using the following formula: TGI (%)=[1−(Ti−T0)/(Vi−V0)]×100. Ti is the average tumor volume in the treatment group on day i. T0 is the average tumor volume in the treatment group on day zero. Vi is the average tumor volume in the control group on day i. V0 is the average tumor volume in the control group on day zero.

T-test was performed for statistical analysis. A TGI % higher than 60% indicates significant suppression of tumor growth. P<0.05 is a threshold to indicate significant difference.

In Vivo Results for Mouse Anti-hCTLA4 Antibodies 13A4 and 4G12

Figure 6:
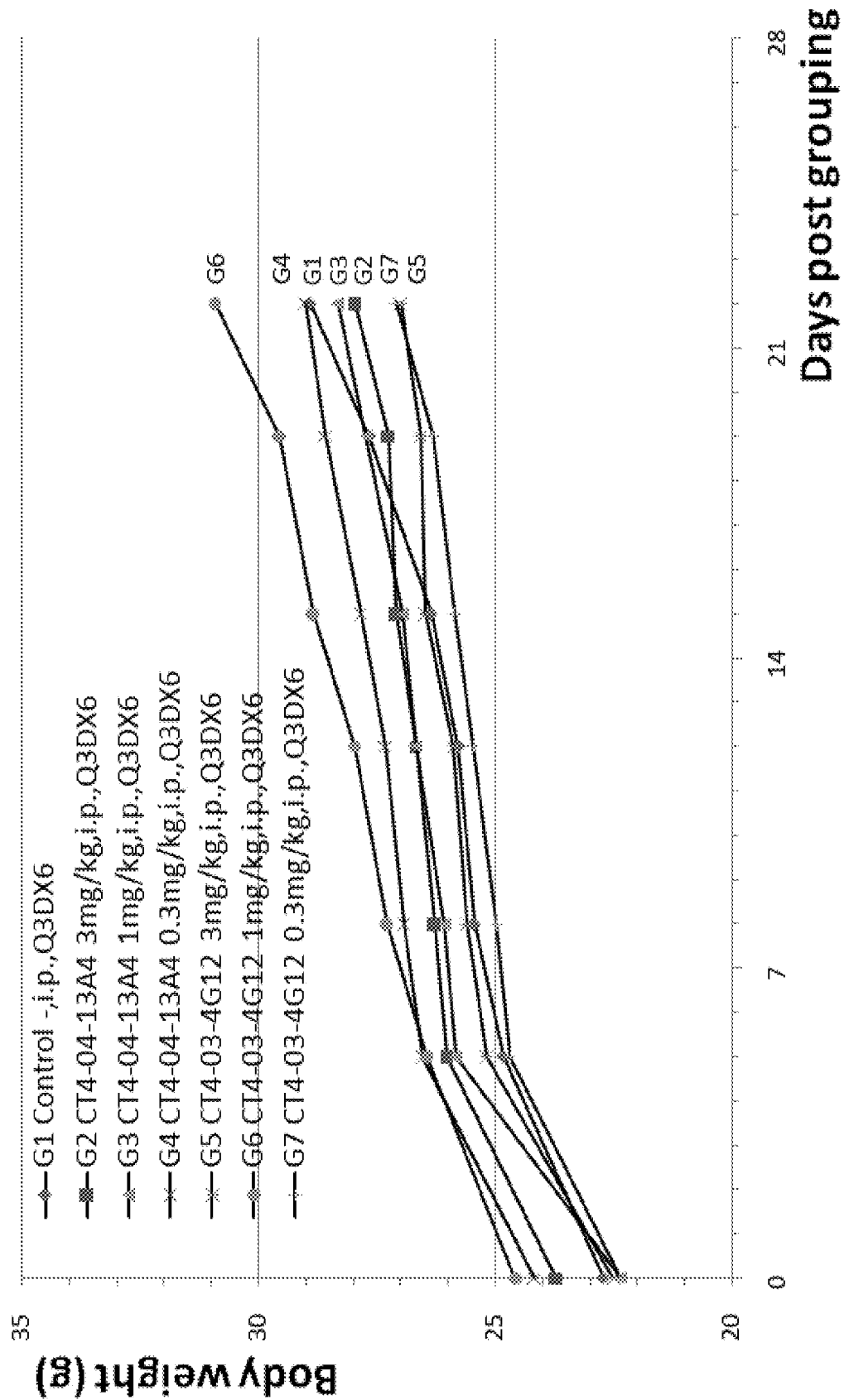
FIG. 6 is a graph showing body weight over time of B-hCTLA-4 humanized mice with MC-38 tumor treated with anti-CTLA4 antibodies 13A4 and 4G12.
Figure 7:
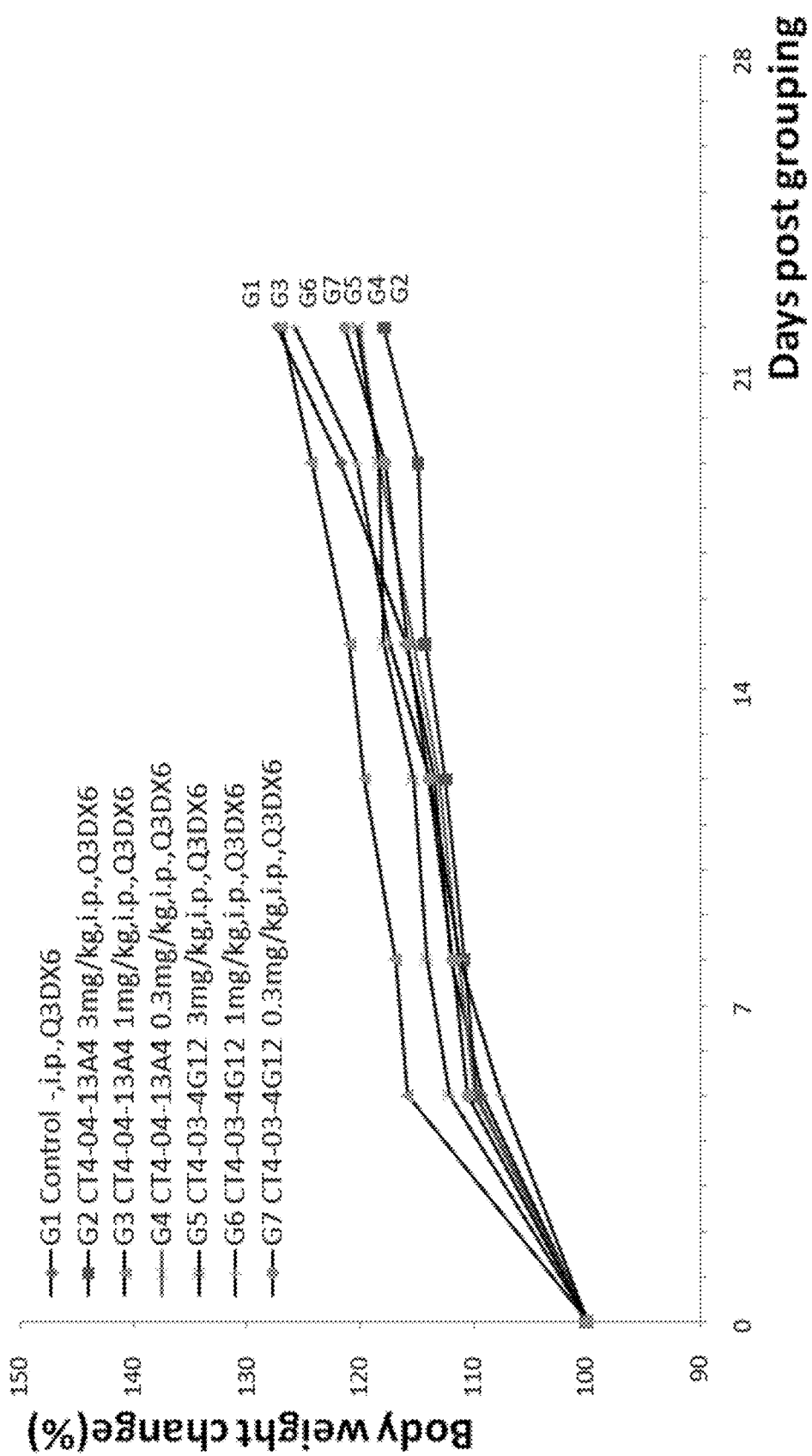
FIG. 7 is a graph showing percentage change of body weight over time of B-hCTLA-4 humanized mice with MC-38 tumor treated with anti-CTLA4 antibodies 13A4 and 4G12.

The weight of the mice was monitored during the entire treatment period. The weight of mice in different groups all increased (FIG. 6, and FIG. 7). No significant difference in weight was observed between the control group and the anti-hCTLA4 treatment groups. The results showed that anti-hCTLA4 antibodies were well tolerated and not toxic to the mice.

Figure 8:
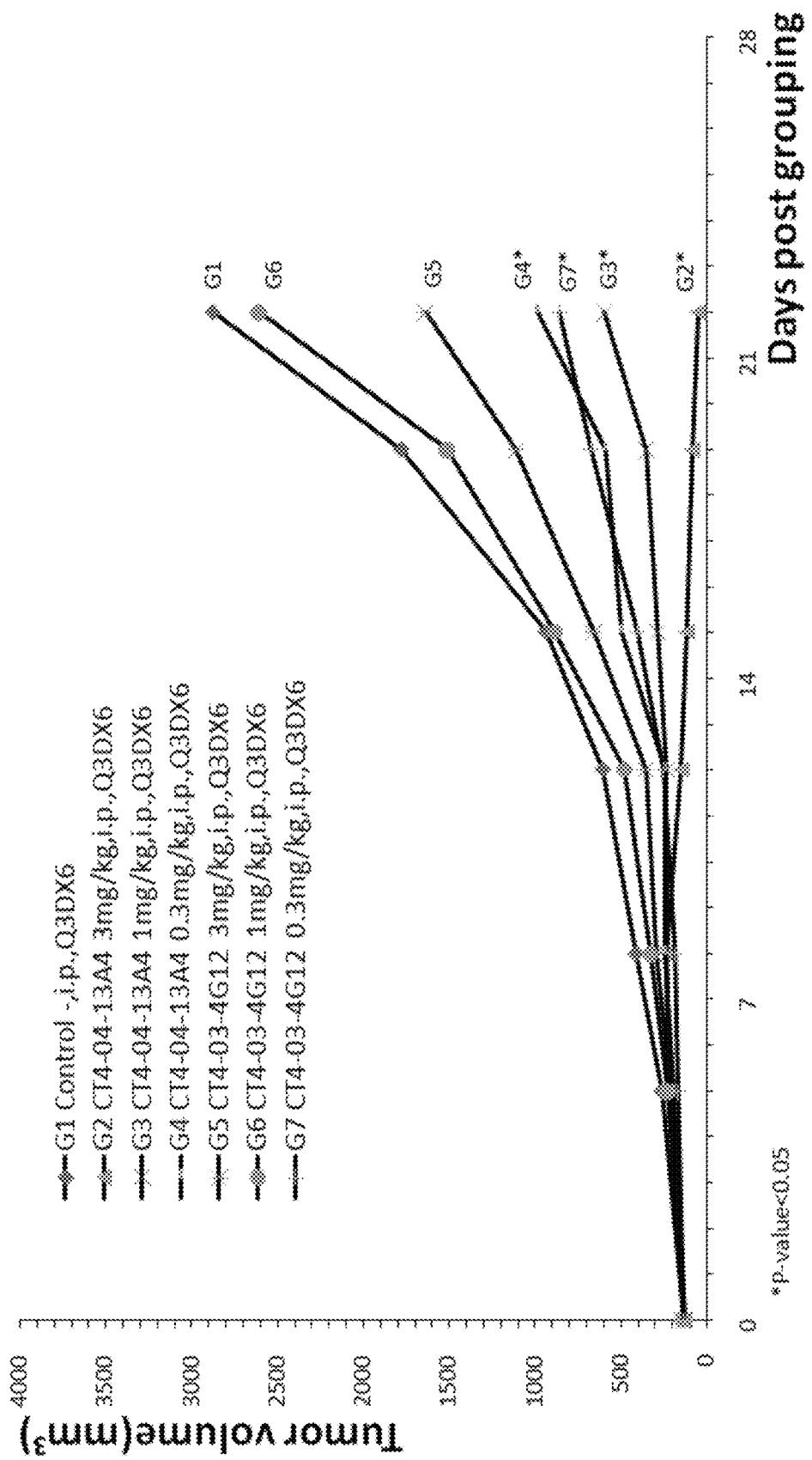
FIG. 8 is a graph showing tumor size over time in B-hCTLA-4 humanized mice with MC-38 tumor treated with anti-CTLA4 antibodies 13A4 and 4G12.

The tumor size, however, showed significant difference in groups treated with antibodies 13A4 and 4G12 (FIG. 8). As shown in FIG. 8, 13A4 and 4G12 inhibited the tumor growth in a concentration dependent manner. Interestingly, 4G12 at the dose of 0.3 mg/kg had better results as compared to 4G12 at the dose of 1 mg/kg, suggesting a relatively low dose (e.g., less than 0.5 mg/kg, or from 0.1 mg/kg to 0.5 mg/kg) of 4G12 can achieve the best results.

The TGI % at day 22 for each treatment group was also calculated as shown in the table below.

TABLE 1

| Group | Antibodies | TGI % |
|---|---|---|
| G2 | 13A4 (3 mg/kg) | 103.00% |
| G3 | 13A4 (1 mg/kg) | 82.90% |
| G4 | 13A4 (0.3 mg/kg) | 69.00% |
| G5 | 4G12 (3 mg/kg) | 45.20% |
| G6 | 4G12 (1 mg/kg) | 10.10% |
| G7 | 4G12 (0.3 mg/kg) | 73.60% |

In Vivo Results for 13A4 and Yervoy®

Figure 9:
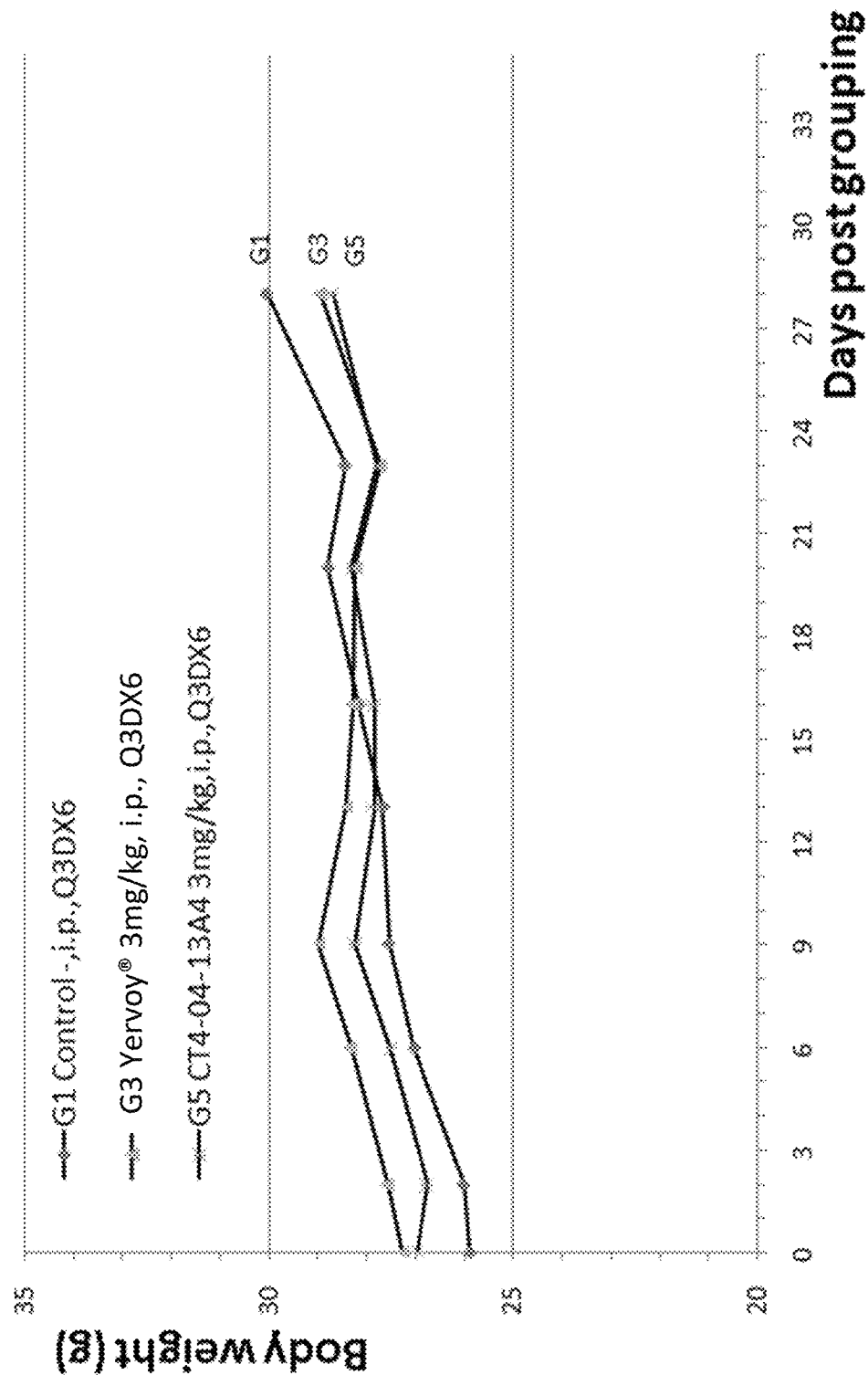
FIG. 9 is a graph showing body weight over time of B-hCTLA-4 humanized mice with MC-38 tumor treated with Yervoy®, and 13A4.
Figure 10:
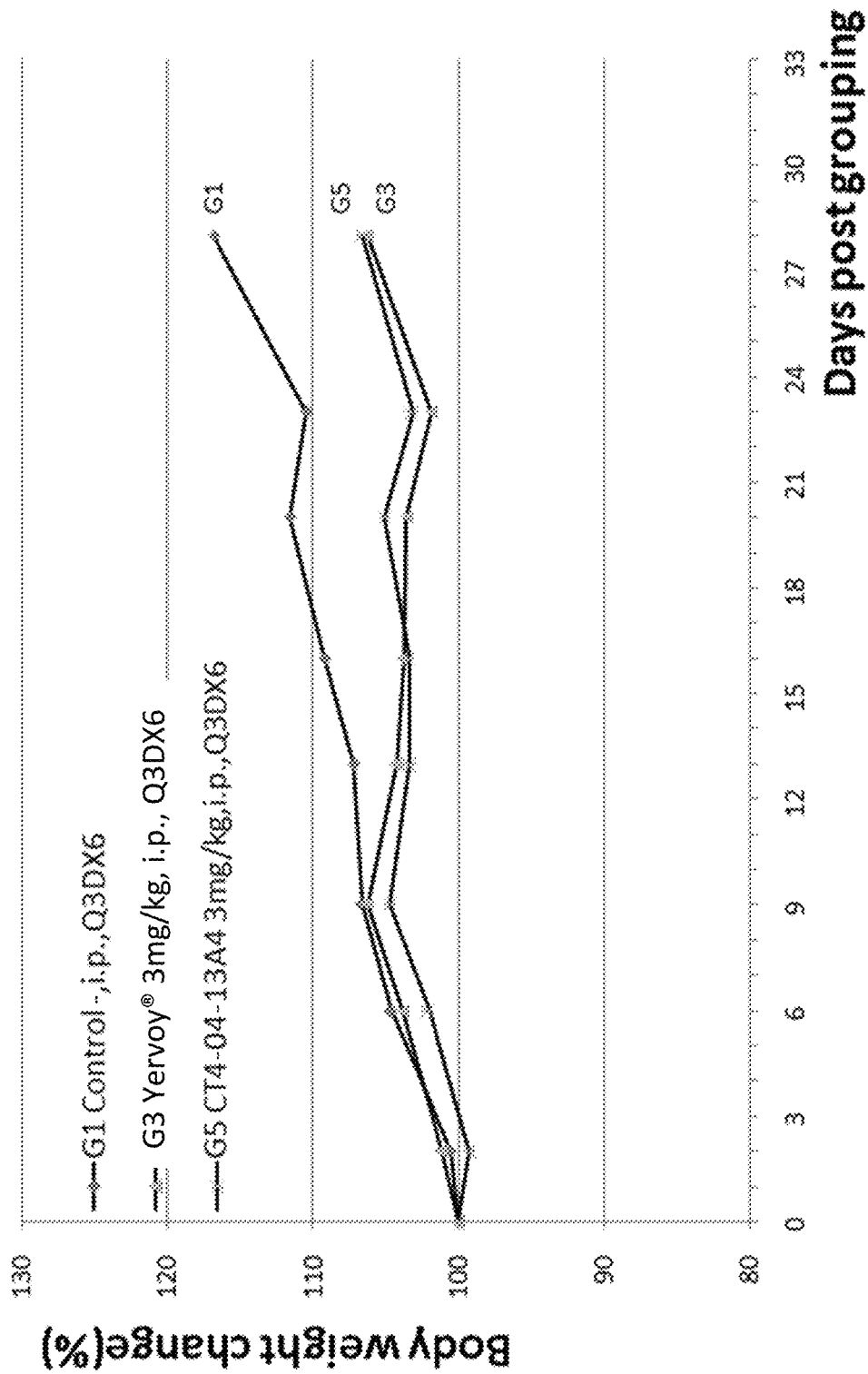
FIG. 10 is a graph showing percentage change of body weight over time of B-hCTLA-4 humanized mice with MC-38 tumor treated with Yervoy®, and 13A4.

To compare the efficacy of the CTLA4 antibodies, Yervoy® was used in the same experiments with 13A4. The weight of the mice in different groups all increased during the treatment period (FIG. 9, and FIG. 10). No toxic effect was observed.

Figure 11:
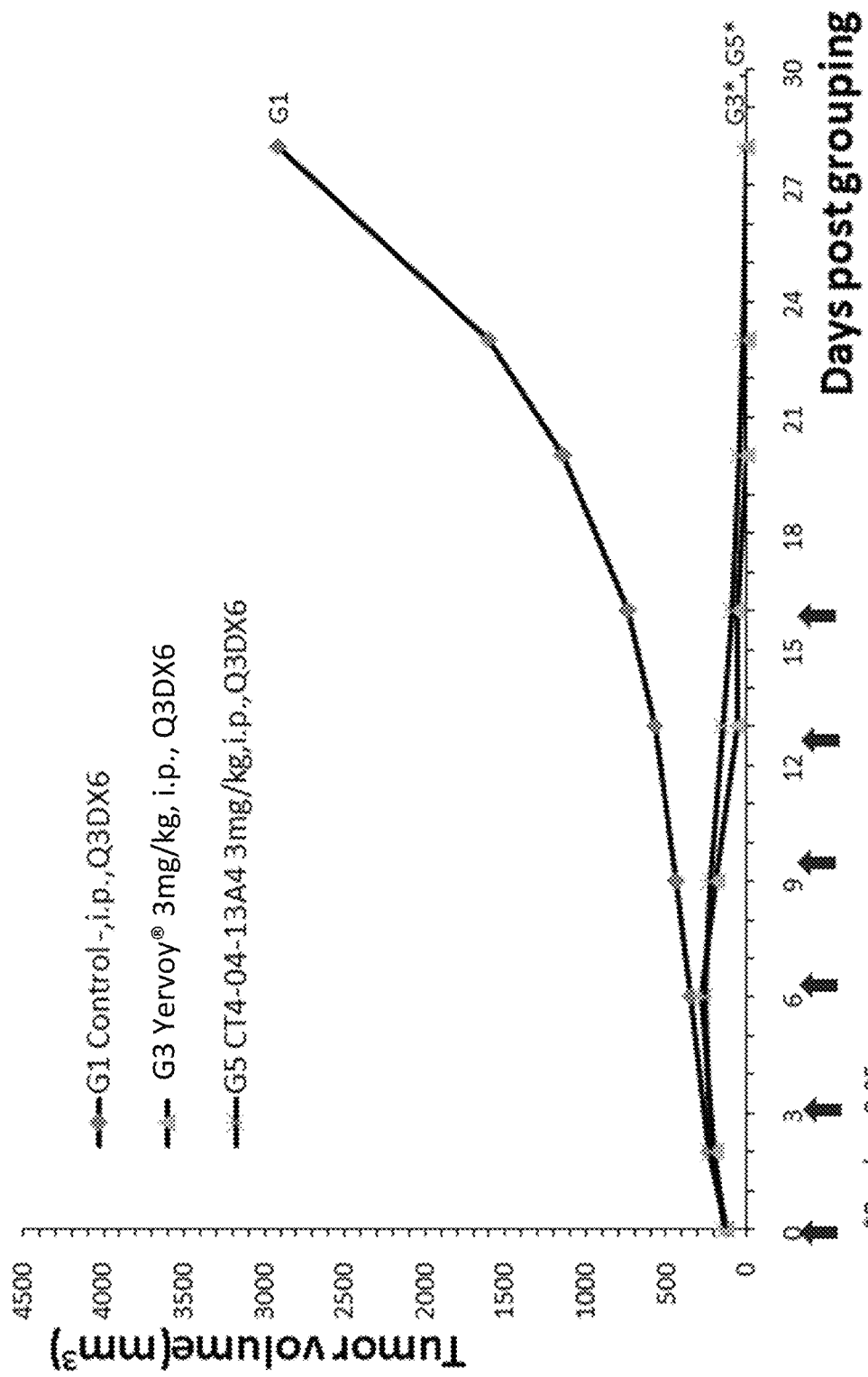
FIG. 11 is a graph showing tumor size over time in B-hCTLA-4 humanized mice with MC-38 tumor treated with Yervoy®, and 13A4.

13A4 and Yervoy® treatment all resulted in significant decrease of tumor size (FIG. 11). Notably, 13A4 treatment resulted in at least comparable effects as compared to Yervoy®. The TGI % at day 28 for both treatment groups was shown below.

TABLE 2

| Group | Antibodies | TGI % |
|---|---|---|
| G3 | Yervoy ® | 104.60% |
| G5 | 13A4 | 104.70% |

Example 6. In Vivo Results for Humanized Anti-hCTLA4 Antibodies

The humanized antibodies were generated by the methods as described in Example 2. To confirm the therapeutic effects of the humanized antibodies, six humanized anti-hCTLA4 antibodies (4G12-H1K1-IgG1; 4G12-H2K1-IgG1; 13A4-H1K2-IgG1; 13A4-H2K2-IgG1; 13A4-H1K2-IgG4; 13A4-H1K2-IgG1-N297A) were tested in B-hCTLA-4 humanized mice to demonstrate their effects on tumor growth in vivo (FIGS. 12-17). Furthermore, to reduce glycan heterogeneity, the Fc region of the humanized antibody 13A4-H1K2-IgG1 was further engineered to replace the Asparagine at position 297 with Alanine (FIG. 17). The light chain and heavy chain variable regions of the antibodies are shown in the table below.

TABLE 3

| Humanized antibodies | Heavy Chain Variable Region | Light Chain Variable Region | Type |
|---|---|---|---|
| 4G12-H1K1-IgG1 | SEQ ID NO: 21 | SEQ ID NO: 25 | IgG1 |
| 4G12-H2K1-IgG1 | SEQ ID NO: 22 | SEQ ID NO: 25 | IgG1 |
| 13A4-H1K2-IgG1 | SEQ ID NO: 13 | SEQ ID NO: 19 | IgG1 |
| 13A4-H2K2-IgG1 | SEQ ID NO: 14 | SEQ ID NO: 19 | IgG1 |
| 13A4-H1K2-IgG4 | SEQ ID NO: 13 | SEQ ID NO: 19 | IgG4 |
| 13A4-H1K2-IgG1-N297A | SEQ ID NO: 13 | SEQ ID NO: 19 | IgG1 with N297A mutation at Fc region. |

Similar procedures as described in Example 5 were used. MC-38 cancer tumor cells (colon adenocarcinoma cell) were injected subcutaneously in B-hCTLA-4 humanized mice. When the tumors in the mice reached a volume of 150±50 mm$^3$, the mice were randomly placed into different groups based on the volume of the tumor. The mice were then injected intravenously with PBS and anti-CTLA4 antibodies. The antibody was given twice a week (day 1, 4 of each week) for 3 weeks (6 injections in total). The dosage was calculated based on the weight of the mouse at 10 mg/kg. The length of the long axis and short axis of the tumor was measured twice every week, and the volume of the tumor was calculated as 0.5×(long axis)×(short axis)$^2$. The weight of the mice was also measured before the injection, and at the time when the mice were placed into different groups (before the first antibody injection). The weight was also measured twice a week during the antibody injection period, and at the time point right before euthanization.

The tumor growth inhibition percentage (TGI %) was calculated using the following formula: TGI (%)=[1−(Ti−T0)/(Vi−V0)]×100. Ti is the average tumor volume in the treatment group on day i. T0 is the average tumor volume in the treatment group on day zero. Vi is the average tumor volume in the control group on day i. V0 is the average tumor volume in the control group on day zero.

T-test was performed for statistical analysis. A TGI % higher than 60% indicates significant suppression of tumor growth. P<0.05 is deemed to indicate significant difference.

In Vivo Results for 4G12-H1K1-IgG1 and 4G12-H2K1-IgG1

The mice were divided into 4 groups: 1) In G1, human IgG was used as the control; 2) In G4, Yervoy® was administered to the mice for comparison purpose; 3) In G10, 4G12-H1K1-IgG1 was administered to the mice; and 4) In G11, 4G12-H2K1-IgG1 was administered to the mice.

Figure 12:
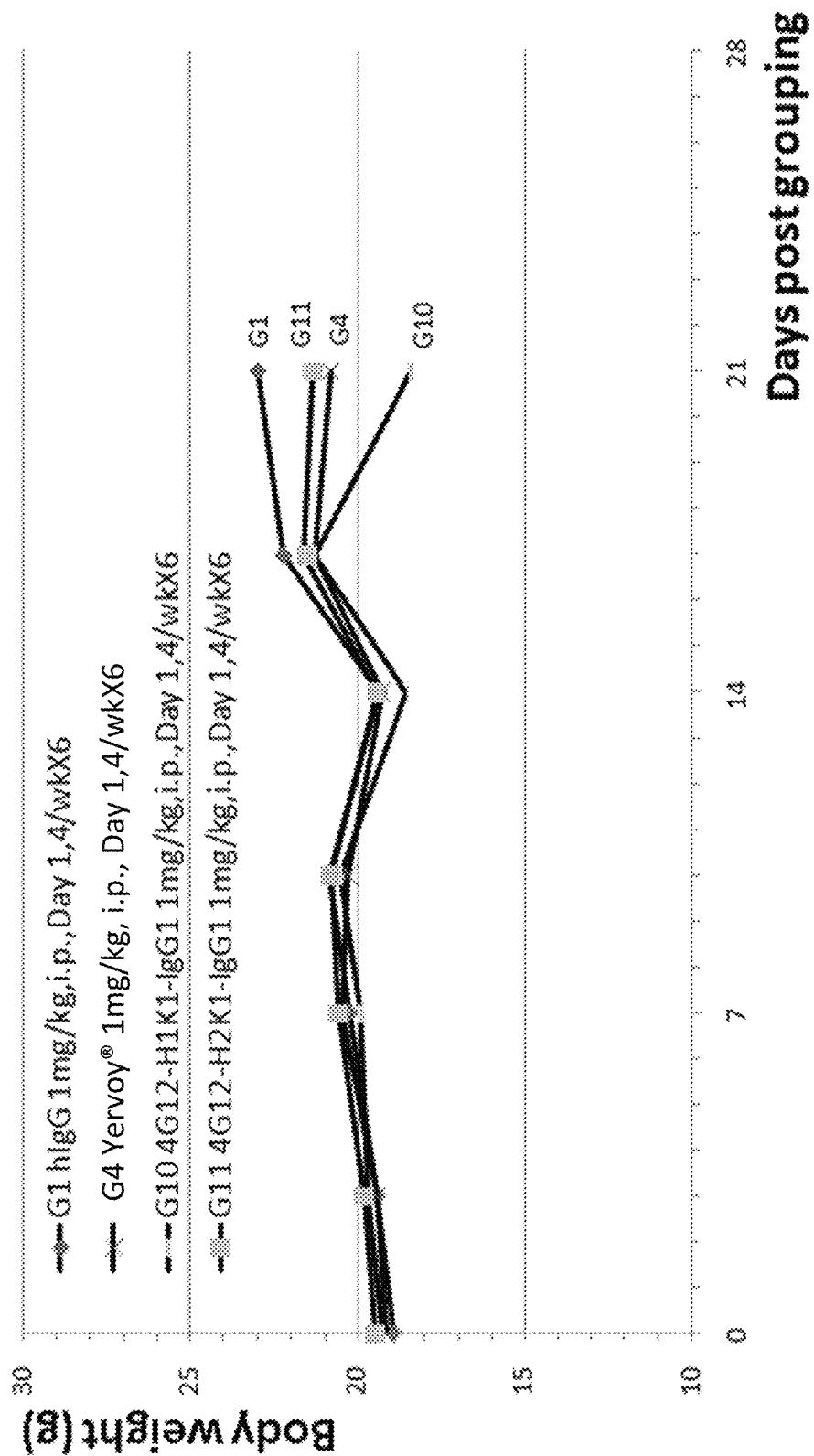
FIG. 12 is a graph showing body weight over time of B-hCTLA-4 humanized mice with MC-38 tumor treated with Yervoy®, humanized anti-hCTLA4 antibodies 4G12-H1K1-IgG1 and 4G12-H2K1-IgG1.
Figure 13:
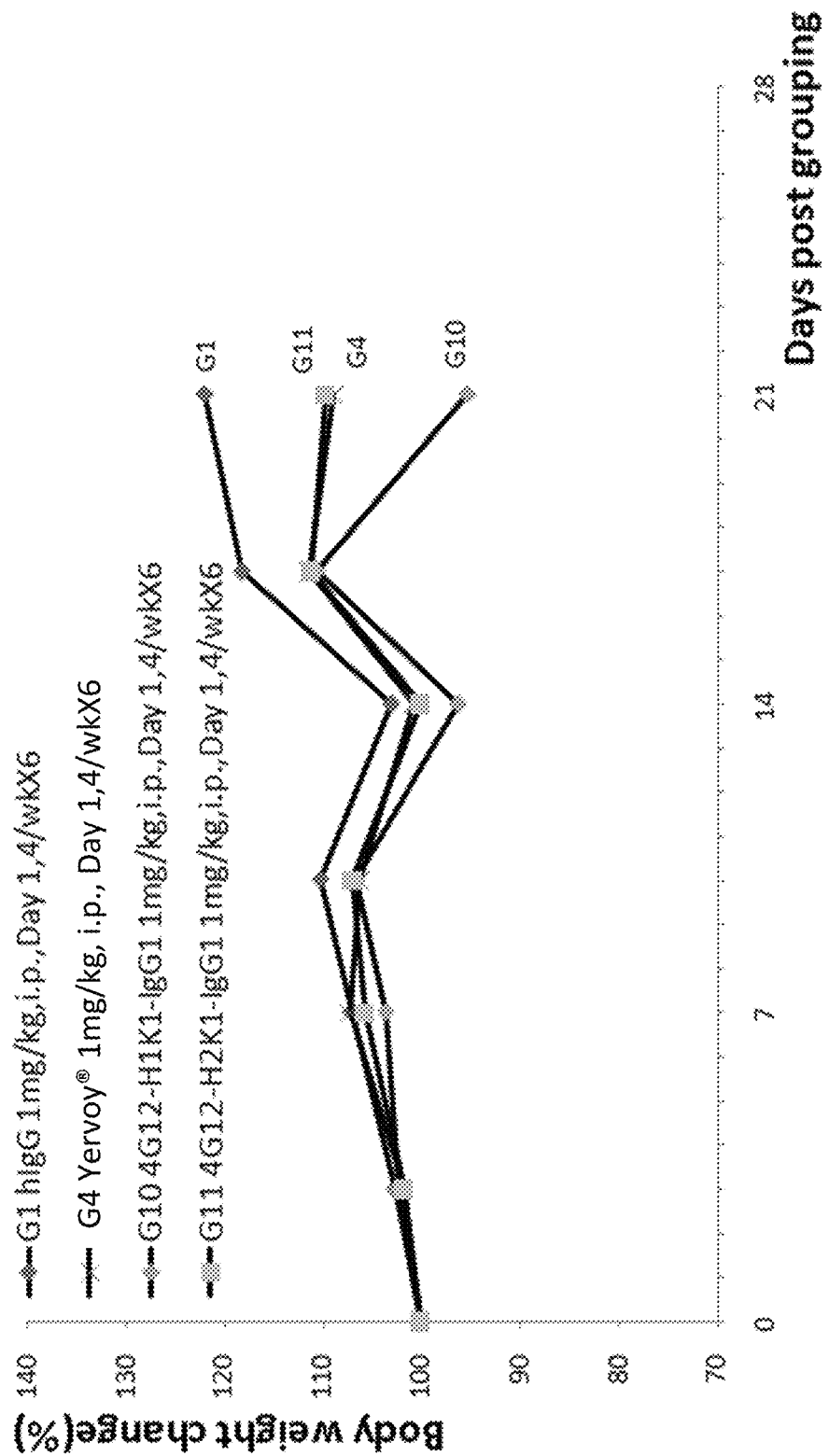
FIG. 13 is a graph showing percentage change of body weight over time of B-hCTLA-4 humanized mice with MC-38 tumor treated with Yervoy®, humanized anti-hCTLA4 antibodies 4G12-H1K1-IgG1 and 4G12-H2K1-IgG1.

The weight of the mice in the four groups was monitored during the entire treatment period (FIG. 12 and FIG. 13). The mice in each group were generally healthy, and the results showed that anti-CTLA4 antibodies were well tolerated and were not toxic to the mice.

Figure 14:
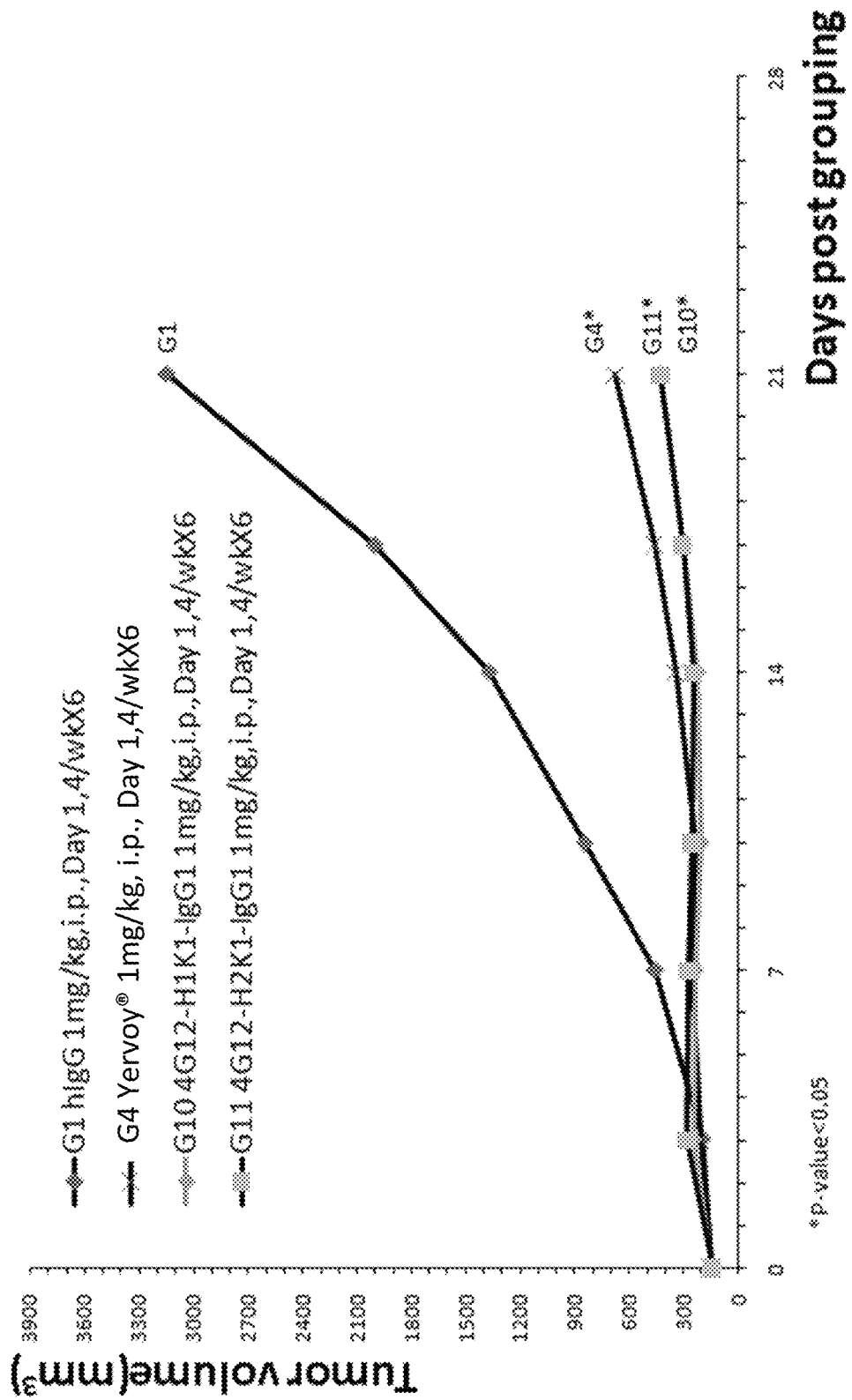
FIG. 14 is a graph showing tumor size over time in B-hCTLA-4 humanized mice with MC-38 tumor treated with Yervoy®, humanized anti-hCTLA4 antibodies 4G12-H1K1-IgG1 and 4G12-H2K1-IgG1.

The tumor size, however, were significantly smaller in groups treated with Yervoy®, 4G12-H1K1-IgG1 and 4G12-H2K1-IgG1 (FIG. 14). As shown in FIG. 14, 4G12-H1K1-IgG1 (P=0.002) and 4G12-H2K1-IgG1 (P=0.002) inhibited the tumor growth as compared to the control group, and had better results as compared to Yervoy® (P=0.007). The TGI % at day 21 for each treatment group was shown below.

TABLE 4

| Group | Antibodies | TGI % |
|---|---|---|
| G4 | Yervoy ® | 82.20% |
| G10 | 4G12-H1K1-IgG1 | 90.50% |
| G11 | 4G12-H2K1-IgG1 | 90.50% |

In Vivo Results for 13A4-H1K2-IgG1, 13A4-H2K2-IgG1, 13A4-H1K2-IgG4 and 13A4-H1K2-IgG1-N297A The mice were placed into 6 groups: 1) In G1, human IgG was used as the control group; 2) In G4, Yervoy® was administered to the mice for comparison purpose; 3) In G6, 13A4-H1K2-IgG1 was administered to the mice; 4) In G7, 13A4-H2K2-IgG1 was administered to the mice; 5) In G8, 13A4-H1K2-IgG4 was administered to the mice; and 6) In G9, 13A4-H1K2-IgG1-N297A was administered to the mice.

Figure 15:
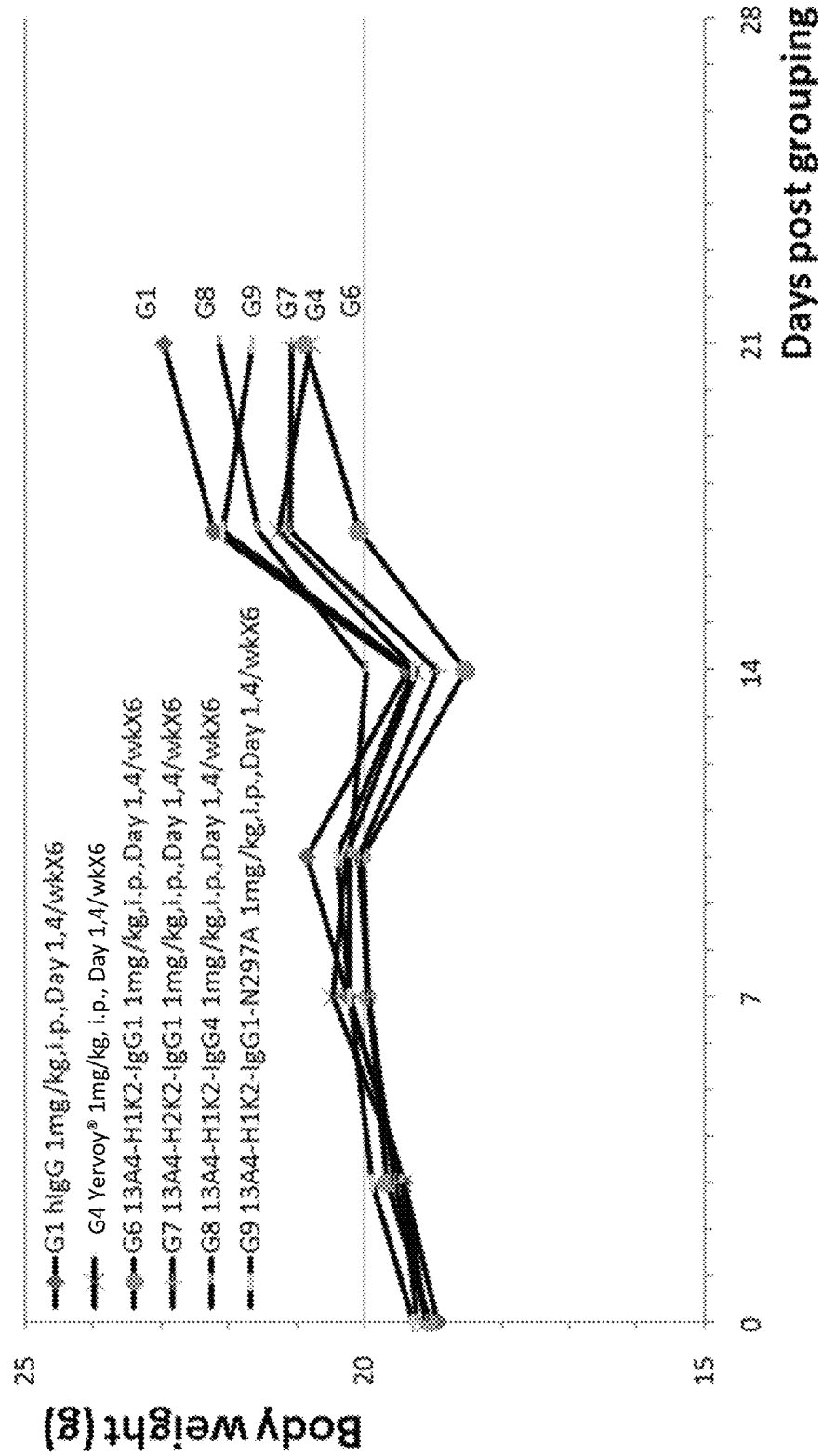
FIG. 15 is a graph showing body weight over time of B-hCTLA-4 humanized mice with MC-38 tumor treated with Yervoy®, humanized anti-hCTLA4 antibodies 13A4-H1K2-IgG1, 13A4-H2K2-IgG1, 13A4-H1K2-IgG4, and 13A4-H1K2-IgG1-N297A.
Figure 16:
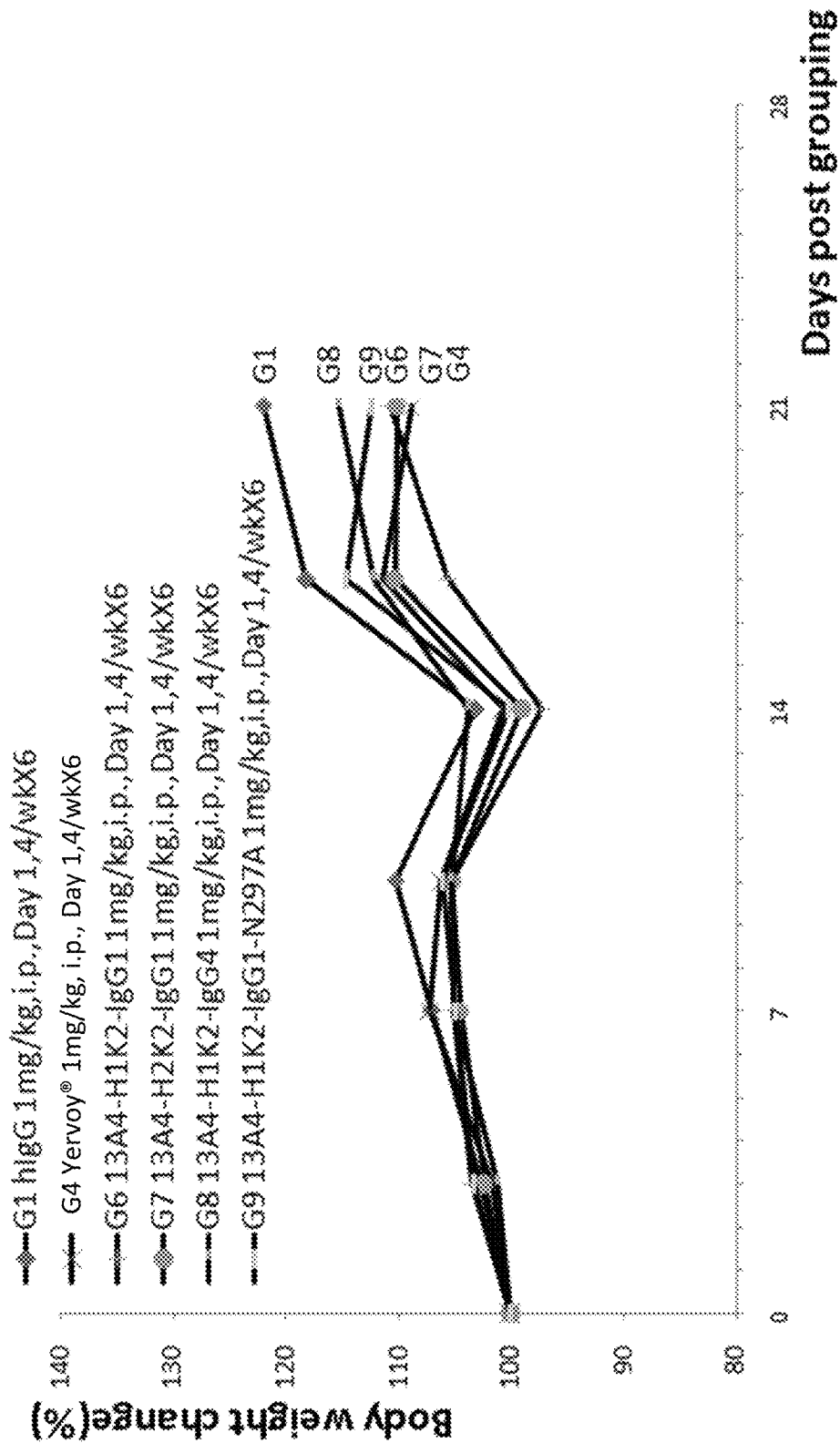
FIG. 16 is a graph showing percentage change of body weight over time of B-hCTLA-4 humanized mice with MC-38 tumor treated with Yervoy®, humanized anti-hCTLA4 antibodies 13A4-H1K2-IgG1, 13A4-H2K2-IgG1, 13A4-H1K2-IgG4, and 13A4-H1K2-IgG1-N297A.
Figure 17:
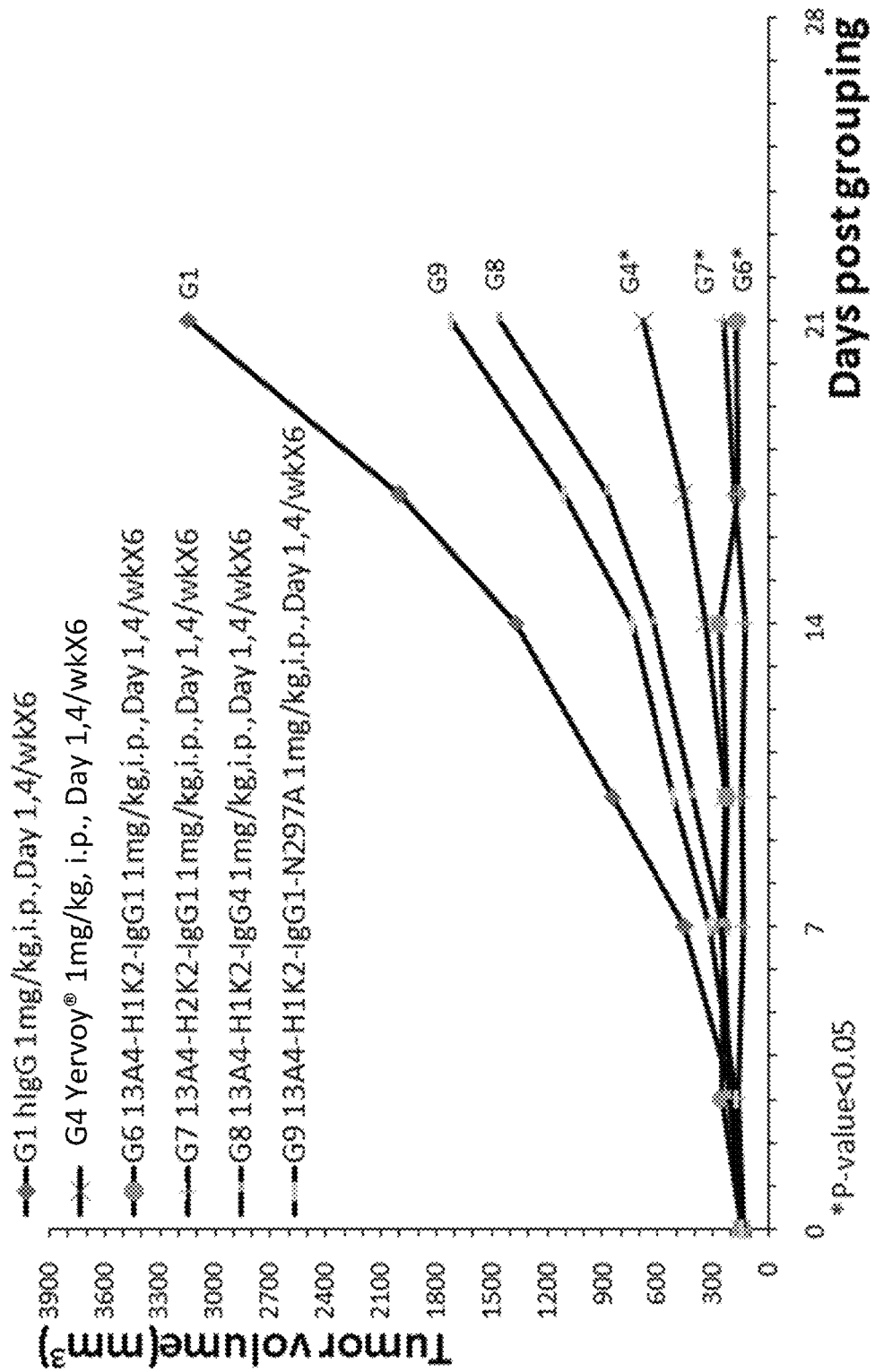
FIG. 17 is a graph showing tumor size over time in B-hCTLA-4 humanized mice with MC-38 tumor treated with Yervoy®, humanized anti-hCTLA4 antibodies 13A4-H1K2-IgG1, 13A4-H2K2-IgG1, 13A4-H1K2-IgG4, and 13A4-H1K2-IgG1-N297A.

The weight of the mice in the six groups was monitored during the entire treatment period (FIG. 15 and FIG. 16). The results showed that the mice in each group were healthy, and anti-CTLA4 antibodies were not toxic to the mice.

The tumor sizes, however, were different in each group. As shown in FIG. 17, all anti-CTLA4 antibodies can inhibit tumor growth as compared to the control group. Particularly, 13A4-H1K2-IgG1 and 13A4-H2K2-IgG1 had better results as compared to Yervoy®.

The TGI % at day 21 for each treatment group was shown below.

TABLE 5

| Group | Antibodies | TGI % |
|---|---|---|
| G4 | Yervoy ® | 82.20% |
| G6 | 13A4-H1K2-IgG1 | 99.00% |
| G7 | 13A4-H2K2-IgG1 | 96.60% |
| G8 | 13A4-H1K2-IgG4 | 56.10% |
| G9 | 13A4-H1K2-IgG1-N297A | 47.30% |

Example 7. In Vitro Testing of the Mouse Anti-hCTLA4 Antibodies: CT4-20-6D2 ("6D2") and CT4-20-7E12 ("7E12")

Anti-CTLA4 antibodies were collected from mouse ascites fluid, and were purified by chromatography. 25 ul CHO cells transiently transfected with human CTLA4 were added to each well in a plate. The purified antibodies were titrated to final concentrations of 50, 5, 0.5, 0.05, 0.005 ug/ml. The titrated antibodies were added to each well at 25 ul per well at 4° C. and incubated for 30 minutes. Biotin-hCD86 was titrated to 0.4 ug/ml. 50 ul of the ligand solution was added to each well, making the final concentration of Biotin-hCD86 0.2 ug/ml. The cells with Biotin-hCD86 were incubated at 4° C. for 15 minutes. After being washed with phosphate-buffered saline (PBS), 50 ul of anti-mouse IgG Fc antibody fluorescein isothiocyanate conjugate (IgG Fc-FITC) and streptavidin-Phycoerythrin (streptavidin-PE) were added at 1:100 dilution into each well at 4° C. and incubated for 15 minutes, followed by PBS wash. The signals for FITC and PE were determined by flow cytometry.

Figure 18:
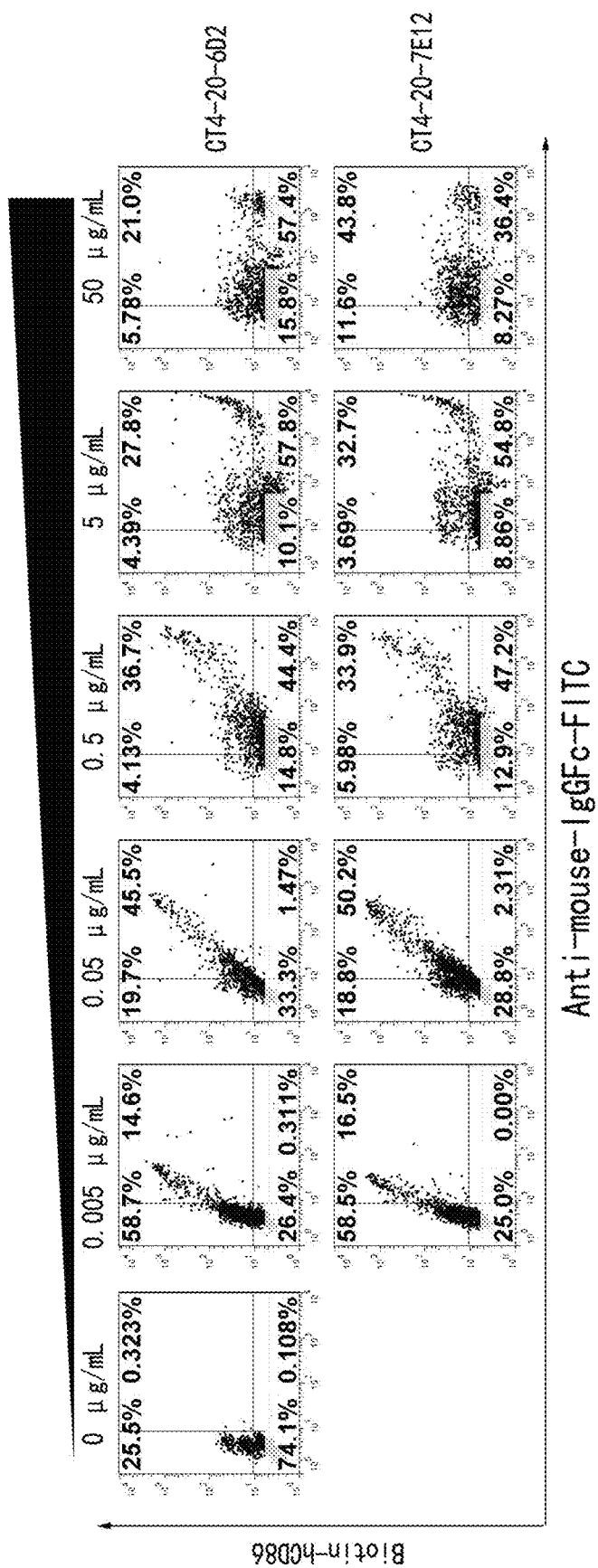
FIG. 18 is a set of flow cytometry graphs showing the anti-CTLA4 antibodies block the binding between CTLA4 and human CD86.

As shown in FIG. 18, when the concentration of the anti-hCTLA4 antibody (CT4-20-6D2 and CT4-20-7E12) increased, the signal for PE decreased, suggesting that the binding between human CTLA4 and Biotin-hCD86 was blocked by CT4-20-6D2 and CT4-20-7E12 antibodies.

Example 8. Cross-Reactivity of Anti-hCTLA Antibodies Against Monkey, Mouse, and Human-Mouse Chimeric CTLA4

CHO cells were transfected with rhesus macaque CTLA4 (rmCTLA4, SEQ ID NO: 43), mouse CTLA4 (mCTLA4, SEQ ID NO: 42), and chimeric (mouse and human) CTLA4 (chiCTLA4, SEQ ID NO: 44).

25 ul CHO cells were added to each well. 25 ul purified mouse anti-hCTLA antibodies (1 ug/ml) (CT4-20-6D2 and CT4-20-7E12) were added to each well and were incubated at 4° C. for 30 minutes.

After being washed with PBS (1200 rmp, 5 min) twice, 50 ul of anti-human IgG Fc antibody fluorescein isothiocyanate conjugate (IgG Fc-FITC) was added at 1:100 dilution into each well and was incubated at 4° C. for 30 minutes, followed by PBS wash. The signals for FITC were determined by flow cytometry.

Figure 19:
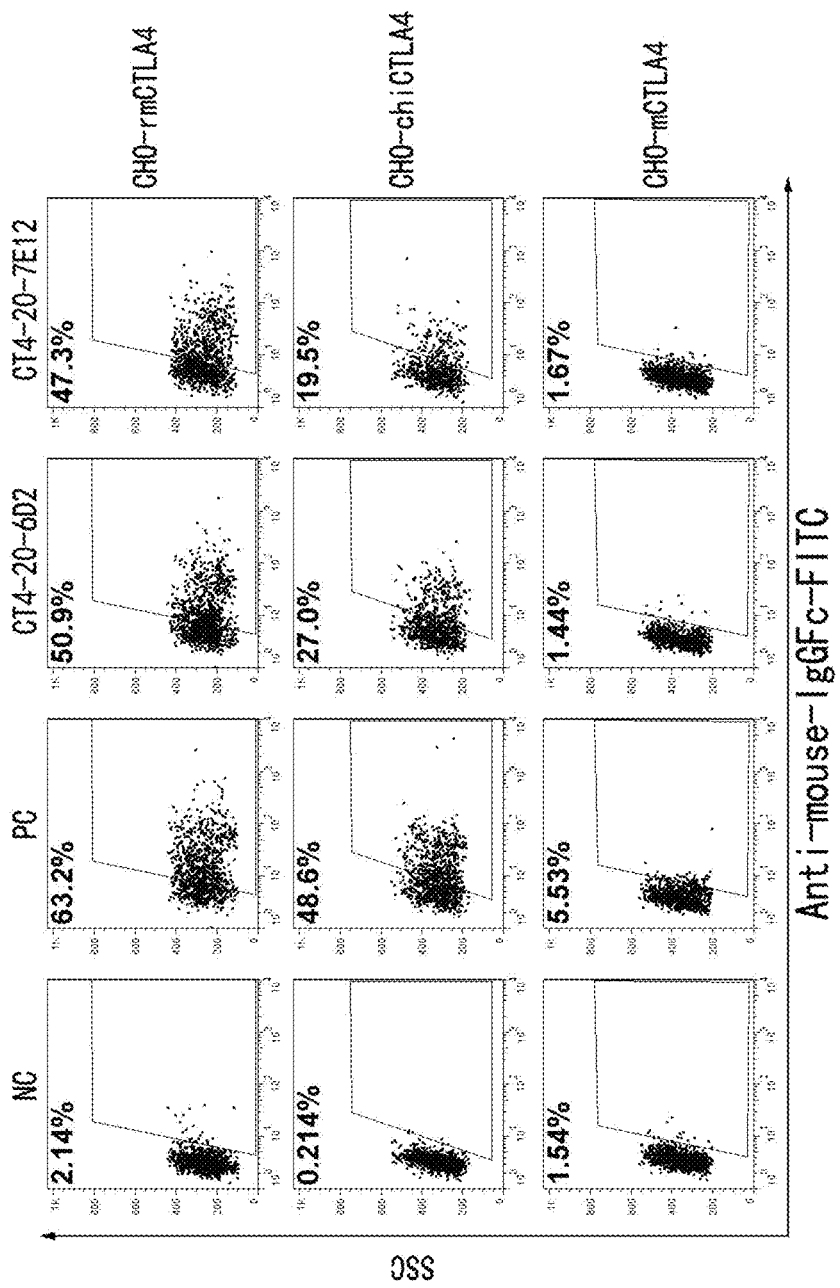
FIG. 19 is a set of graphs showing flow cytometry results of anti-CTLA4 antibodies' cross-reactivity against monkey, mouse, and human-mouse chimeric CTLA4

As shown in FIG. 19, CT4-20-6D2 and CT4-20-7E12 did not cross react with mouse CTLA4, had weak cross reactivity with chimeric CTLA4 and relatively strong cross reactivity with rmCTLA4.

Example 9. In Vivo Testing of Mouse Anti-hCTLA4 Antibodies

The anti-hCTLA4 antibodies were tested to demonstrate their effect on tumor growth in vivo in a model of colon carcinoma. MC-38 cancer tumor cells (colon adenocarcinoma cell) were injected subcutaneously in B-hCTLA-4 humanized mice. When the tumors in the mice reached a volume of 150±50 mm$^3$, the mice were randomly placed into different groups based on the volume of the tumor. The mice were then injected intravenously with PBS and anti-hCTLA4 antibodies. The antibody was given twice a week (6 injections in total). In the control group, saline was administered to the mice. The injected volume was calculated based on the weight of the mouse at 10 ul/g. The length of the long axis and short axis of the tumor was measured twice every week, and the volume of the tumor was calculated as 0.5×(long axis)×(short axis)$^2$. The weight of the mice was also measured before the injection, when the mice were placed into different groups (before the first antibody injection), twice a week during the antibody injection period, and before euthanization.

T-test was performed for statistical analysis. A TGI % higher than 60% indicates significant suppression of tumor growth. $P<0.05$ is deemed to indicate significant difference.

Figure 20:
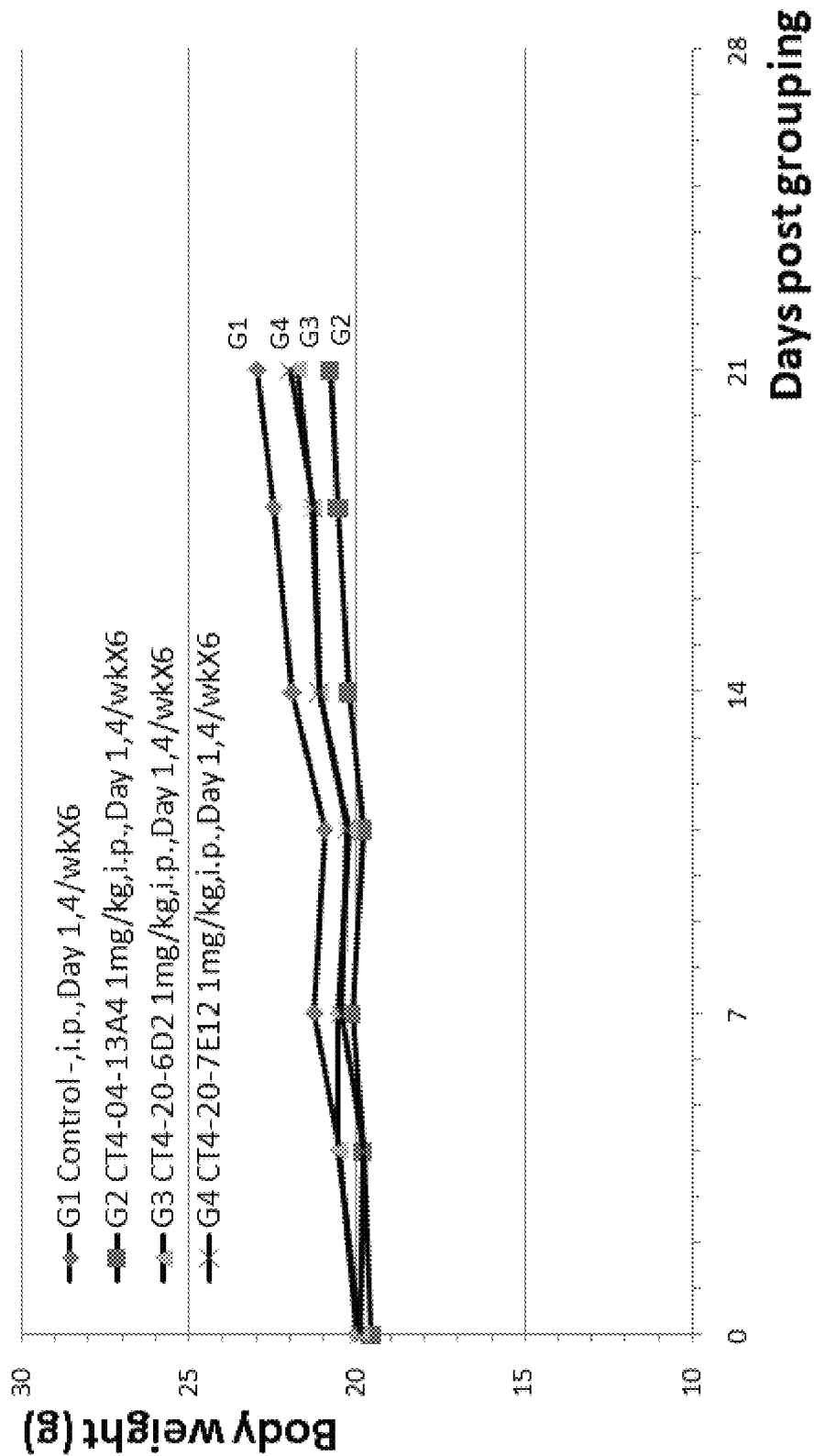
FIG. 20 is a graph showing body weight over time of B-hCTLA-4 humanized mice with MC-38 tumor treated with CT4-04-13A4, CT4-20-6D2, and CT4-20-7E12.
Figure 21:
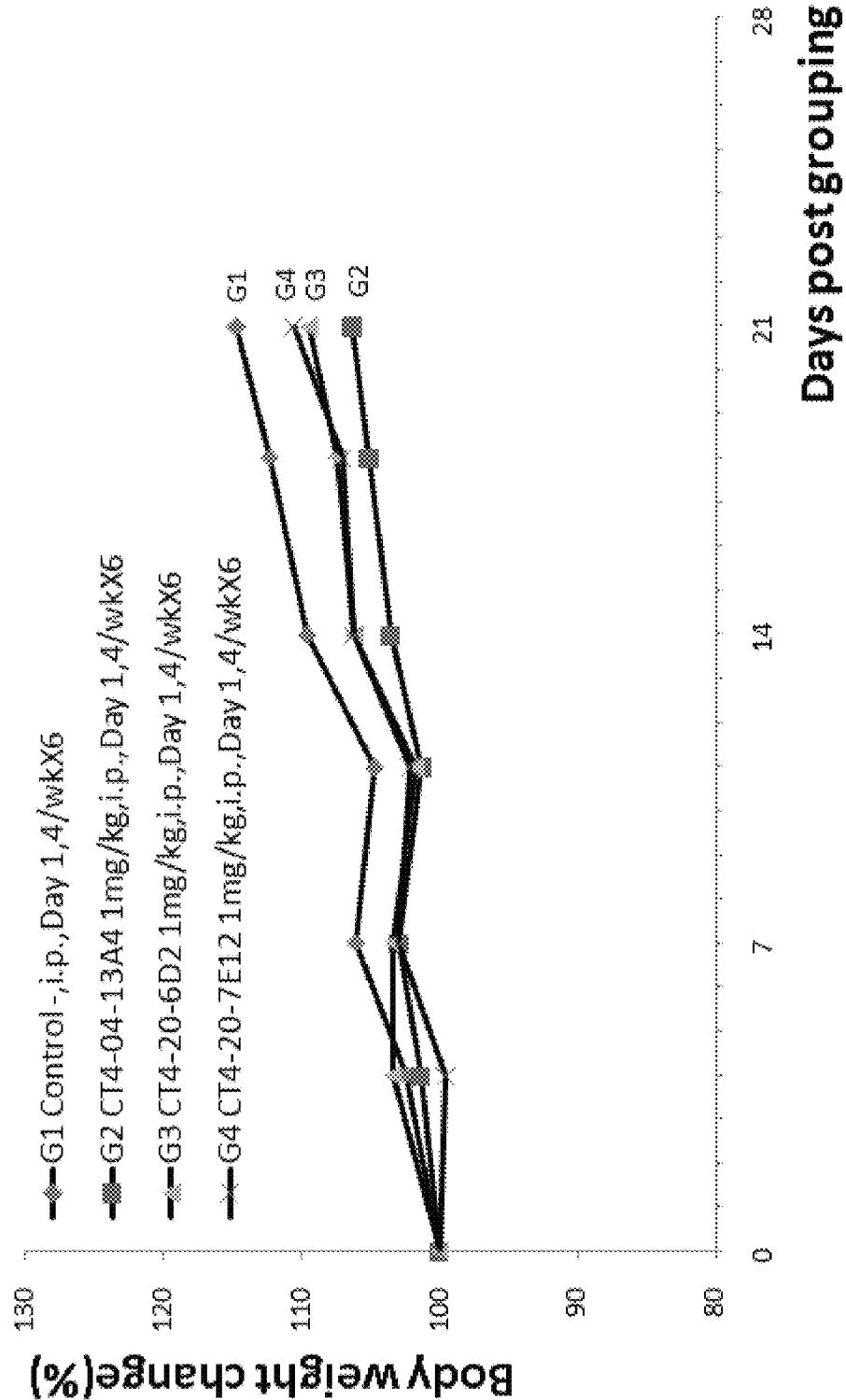
FIG. 21 is a graph showing percentage change of body weight over time of B-hCTLA-4 humanized mice with MC-38 tumor treated with CT4-04-13A4, CT4-20-6D2, and CT4-20-7E12.

The weight of the mice was monitored during the entire treatment period. The weight of mice in different groups all increased (FIG. 20, and FIG. 21). No significant difference in weight was observed between the control group and the anti-hCTLA4 treatment groups. The results showed that anti-hCTLA4 antibodies were not toxic to the mice.

Figure 22:
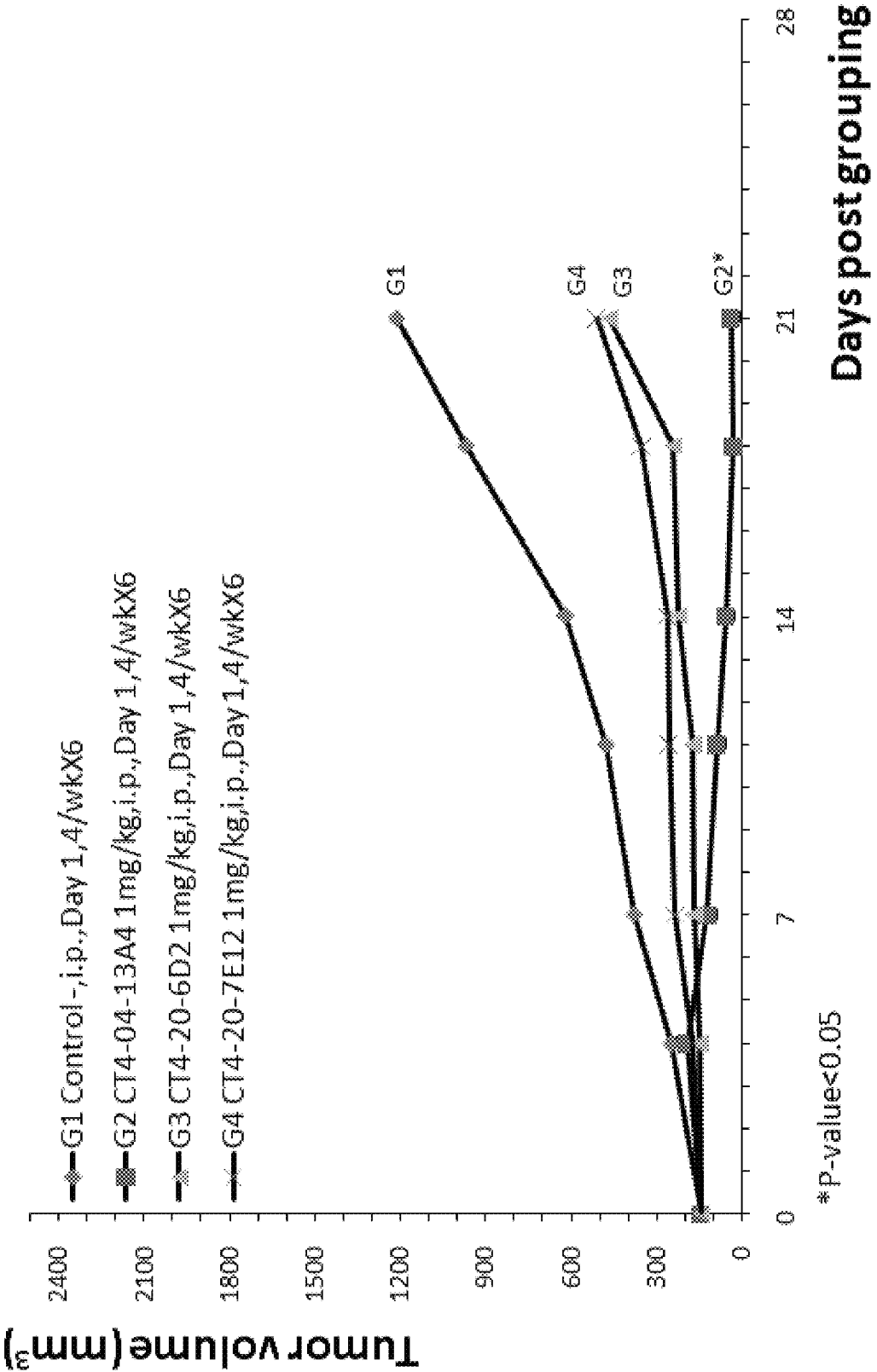
FIG. 22 is a graph showing tumor size over time in B-hCTLA-4 humanized mice with MC-38 tumor treated with CT4-04-13A4, CT4-20-6D2, and CT4-20-7E12.

The tumor size, however, showed significant difference in groups treated with antibodies 13A4, 6D2 and 7E12 (FIG. 22). As shown in FIG. 22, 13A4, 6D2, and 7E12 all inhibited the tumor growth in the mice.

The TGI % at day 21 for each treatment group was shown below.

TABLE 6

| Group | Antibodies | TGI % |
|---|---|---|
| G2 | 13A4 | 109.70% |
| G3 | 6D2 | 69.80% |
| G4 | 7E12 | 65.60% |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that binds to cytotoxic T-lymphocyte-associated protein 4 (CTLA4) comprising:
   a heavy chain variable region (VH) comprising complementarity determining regions (CDRs) 1, 2, and 3, wherein the VH CDR1 region comprises an amino acid sequence that is identical to a reference VH CDR1 amino acid sequence, the VH CDR2 region comprises an amino acid sequence that is identical to a reference VH CDR2 amino acid sequence, and the VH CDR3 region comprises an amino acid sequence that is identical to a reference VH CDR3 amino acid sequence; and
   a light chain variable region (VL) comprising CDRs 1, 2, and 3, wherein the VL CDR1 region comprises an amino acid sequence that is identical to a reference VL CDR1 amino acid sequence, the VL CDR2 region comprises an amino acid sequence that is identical to a reference VL CDR2 amino acid sequence, and the VL CDR3 region comprises an amino acid sequence that is identical to a reference VL CDR3 amino acid sequence,
   wherein the reference VH CDRs 1, 2, and 3 amino acid sequences and the reference VL CDRs, 1, 2, and 3 amino acid sequences are one of the following:
   (1) the reference VH CDRs 1, 2, 3 amino acid sequences are set forth in SEQ ID NOs: 1, 2, 3, respectively, and the reference VL CDRs 1, 2, 3 amino acid sequences are set forth in SEQ ID NOs: 4, 5, 6, respectively;
   (2) the reference VH CDRs 1, 2, 3 amino acid sequences are set forth in SEQ ID NOs: 7, 8, 9, respectively, and the reference VL CDRs 1, 2, 3 amino acid sequences are set forth in SEQ ID NOs: 10, 11, 12, respectively;
   (3) the reference VH CDRs 1, 2, 3 amino acid sequences are set forth in SEQ ID NOs: 45, 46, 47, respectively, and the reference VL CDRs 1, 2, 3 amino acid sequences are set forth in SEQ ID NOs: 48, 49, 50, respectively;
   (4) the reference VH CDRs 1, 2, 3 amino acid sequences are set forth in SEQ ID NOs: 51, 52, 53, respectively, and the reference VL CDRs 1, 2, 3 amino acid sequences are set forth in SEQ ID NOs: 54, 55, 56, respectively;
   (5) the reference VH CDRs 1, 2, 3 amino acid sequences are set forth in SEQ ID NOs: 29, 30, 31, respectively, and the reference VL CDRs 1, 2, 3 amino acid sequences are set forth in SEQ ID NOs: 32, 33, 34, respectively;
   (6) the reference VH CDRs 1, 2, 3 amino acid sequences are set forth in SEQ ID NOs: 35, 36, 37, respectively, and the reference VL CDRs 1, 2, 3 amino acid sequences are set forth in SEQ ID NOs: 38, 39, 40, respectively;
   (7) the reference VH CDRs 1, 2, 3 amino acid sequences are set forth in SEQ ID NOs: 57, 58, 59, respectively, and the reference VL CDRs 1, 2, 3 amino acid sequences are set forth in SEQ ID NOs: 60, 61, 62, respectively; and
   (8) the reference VH CDRs 1, 2, 3 amino acid sequences are set forth in SEQ ID NOs: 63, 64, 65, respectively, and the reference VL CDRs 1, 2, 3 amino acid sequences are set forth in SEQ ID NOs: 66, 67, 68, respectively.

2. The antibody or antigen-binding fragment thereof of claim 1, wherein the VH comprises CDRs 1, 2, 3 with the amino acid sequences set forth in SEQ ID NOs: 35, 36, and 37, respectively, and the VL comprises CDRs 1, 2, 3 with the amino acid sequences set forth in SEQ ID NOs: 38, 39, and 40, respectively, according to Chothia definition.

3. The antibody or antigen-binding fragment thereof of claim 1, wherein the VH comprises CDRs 1, 2, 3 with the amino acid sequences set forth in SEQ ID NOs: 7, 8, and 9 respectively, and the VL comprises CDRs 1, 2, 3 with the amino acid sequences set forth in SEQ ID NOs: 10, 11, and 12, respectively, according to Kabat definition.

4. The antibody or antigen-binding fragment thereof of claim 1, wherein the antibody or antigen-binding fragment thereof specifically binds to human CTLA4.

5. The antibody or antigen-binding fragment thereof of claim 1, wherein the antibody or antigen-binding fragment thereof is a humanized antibody or antigen-binding fragment thereof.

6. The antibody or antigen-binding fragment thereof of claim 1, wherein the antibody or antigen-binding fragment thereof is a single-chain variable fragment (scFV) or a multi-specific antibody.

7. A nucleic acid comprising a polynucleotide encoding a polypeptide comprising:
  (1) a heavy chain variable region (VH) comprising complementarity determining regions (CDRs) 1, 2, and 3 comprising the amino acid sequences set forth in SEQ ID NOs: 1, 2, and 3, respectively;
  (2) a light chain variable region (VL) comprising CDRs 1, 2, and 3 comprising the amino acid sequences set forth in SEQ ID NOs: 4, 5, and 6, respectively;
  (3) a VH comprising CDRs 1, 2, and 3 comprising the amino acid sequences set forth in SEQ ID NOs: 7, 8, and 9, respectively;
  (4) a VL comprising CDRs 1, 2, and 3 comprising the amino acid sequences set forth in SEQ ID NOs: 10, 11, and 12, respectively;
  (5) a VH comprising CDRs 1, 2, and 3 comprising the amino acid sequences set forth in SEQ ID NOs: 45, 46, and 47, respectively;
  (6) a VL comprising CDRs 1, 2, and 3 comprising the amino acid sequences set forth in SEQ ID NOs: 48, 49, and 50, respectively;
  (7) a VH comprising CDRs 1, 2, and 3 comprising the amino acid sequences set forth in SEQ ID NOs: 51, 52, and 53, respectively; or
  (8) a VL comprising CDRs 1, 2, and 3 comprising the amino acid sequences set forth in SEQ ID NOs: 54, 55, and 56, respectively.

8. A vector comprising the nucleic acid of claim 7.

9. A cell comprising the nucleic acid of claim 7.

10. A method of producing an antibody or an antigen-binding fragment thereof, the method comprising
  culturing the cell of claim 9 under conditions sufficient for the cell to produce the antibody or the antigen-binding fragment thereof.

11. An antibody-drug conjugate comprising the antibody or antigen-binding fragment thereof of claim 1 covalently bound to a therapeutic agent.

12. A pharmaceutical composition comprising the antibody or antigen-binding fragment thereof of claim 1, and a pharmaceutically acceptable carrier.

13. The antibody or antigen-binding fragment thereof of claim 1, wherein the VH comprises CDRs 1, 2, 3 with the amino acid sequences set forth in SEQ ID NOs: 1, 2, and 3, respectively, and the VL comprises CDRs 1, 2, 3 with the amino acid sequences set forth in SEQ ID NOs: 4, 5, and 6, respectively, according to Kabat definition.

14. The antibody or antigen-binding fragment thereof of claim 1, wherein the VH comprises CDRs 1, 2, 3 with the amino acid sequences set forth in SEQ ID NOs: 29, 30, and 31, respectively, and the VL comprises CDRs 1, 2, 3 with the amino acid sequences set forth in SEQ ID NOs: 32, 33, and 34, respectively, according to Chothia definition.

15. The antibody or antigen-binding fragment thereof of claim 1, wherein the VH comprises CDRs 1, 2, 3 with the amino acid sequences set forth in SEQ ID NOs: 45, 46, and 47, respectively, and the VL comprises CDRs 1, 2, 3 with the amino acid sequences set forth in SEQ ID NOs: 48, 49, and 50, respectively, according to Kabat definition.

16. The antibody or antigen-binding fragment thereof of claim 1, wherein the VH comprises CDRs 1, 2, 3 with the amino acid sequences set forth in SEQ ID NOs: 57, 58, and 59, respectively, and the VL comprises CDRs 1, 2, 3 with the amino acid sequences set forth in SEQ ID NOs: 60, 61, and 62, respectively, according to Chothia definition.

17. The antibody or antigen-binding fragment thereof of claim 1, wherein the VH comprises CDRs 1, 2, 3 with the amino acid sequences set forth in SEQ ID NOs: 51, 52, and 53, respectively, and the VL comprises CDRs 1, 2, 3 with the amino acid sequences set forth in SEQ ID NOs: 54, 55, and 56, respectively, according to Kabat definition.

18. The antibody or antigen-binding fragment thereof of claim 1, wherein the VH comprises CDRs 1, 2, 3 with the amino acid sequences set forth in SEQ ID NOs: 63, 64, and 65, respectively, and the VL comprises CDRs 1, 2, 3 with the amino acid sequences set forth in SEQ ID NOs: 66, 67, and 68, respectively, according to Chothia definition.

* * * * *